United States Patent
Kunita

(10) Patent No.: US 7,041,711 B2
(45) Date of Patent: May 9, 2006

(54) POLYMERIZABLE COMPOSITION AND COMPOUND THEREFOR

(75) Inventor: Kazuto Kunita, Shizuoka (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 41 days.

(21) Appl. No.: 10/793,212

(22) Filed: Mar. 5, 2004

(65) Prior Publication Data

US 2005/0008967 A1    Jan. 13, 2005

(30) Foreign Application Priority Data

Mar. 5, 2003    (JP)    .......................... P.2003-058582

(51) Int. Cl.
- C08G 18/04    (2006.01)
- C08G 18/06    (2006.01)
- C08J 3/28    (2006.01)
- C02F 2/46    (2006.01)
- G03C 1/73    (2006.01)

(52) U.S. Cl. .................... 522/100; 522/96; 522/109; 522/110; 522/113; 522/114; 522/116; 522/117; 430/269; 430/270.1; 430/270.11; 430/280.1; 430/281.1; 430/287.1; 430/288.1; 528/44; 528/48; 528/49; 528/66; 528/67; 528/75; 528/80; 528/81

(58) Field of Classification Search .................. 522/96, 522/113, 114, 116, 117, 150, 152, 173, 174; 528/44, 48, 49, 66, 67, 75, 80, 81; 430/269, 430/270.1, 270.11, 280.1, 281.1, 287.1, 288.1

See application file for complete search history.

(56) References Cited

U.S. PATENT DOCUMENTS

| 2,850,445 | A |   | 9/1958 | Oster |   |
|---|---|---|---|---|---|
| 4,708,925 | A |   | 11/1987 | Newman |   |
| 2002/0016383 | A1 | * | 2/2002 | Iwata et al. | ................. 523/106 |

FOREIGN PATENT DOCUMENTS

| EP | 1 243 906 A1 |   | 9/2002 |
|---|---|---|---|
| JP | 44-20189 B |   | 8/1969 |
| JP | 8-276558 A |   | 10/1996 |
| JP | 2003-221420 | * | 8/2003 |

OTHER PUBLICATIONS

Nakabayashi, Norio, et al., Database Chemabs Online! Chemical Abstracts Service, Columbus, OH, US "Photocurable acrylic dental resin compositions" XP002292101 retrieved from STN Database accession No. 124:299008 see RN 117804-97-4 (abstract) JP 08 034707 A2 (TOA Gosei KK, Japan; Nakabayashi Norio) Feb. 6, 1996.

Nakamura, Shinya et al., Database Chemabs Online! Chemical Abstracts Serivce, Columbus, OH, US "Actinic ray-curable coating compositions with good curability" XP002292102 retrieved from STN Database accession No. 134:164565 see RN 325147-27-1 (abstract) & JP 2001 040039 A2 (Dainippon Ink and Chemicals, Inc., Japan) Feb 13, 2001.

Assumption, Heidi J. et al., Database Chemabs Online! Chemical Abstracts Service, Columbus, OH, US "Photopolymerization of urethane dimethacrylates synthesized via a non-isocycanate route" XP002292103 retrieved from STN Database accession No. 138:402115 see RN 528819-25-2 (abstract) & Polymer Preprints (American Chemical Society, Division of Polymer Chemistry), 44(1), 136-137 Coden: ACPPAY; ISSN 0032-3934, 2003.

Fujimoto, Toshikazu, Database Chemabs Online! Chemical Abstracts Service, Columbus, OH, US; "Radiation-curable composition and its cured film for manufacture of shadow mask or aperture grille" XP002292104 retrieved from STN Database accession No. 139:157382 see RN 325147-27-1 (abstract) & JP 2003 221420 A2 (Mitsubishi Rayon Co., Ltd., Japan) Aug. 5, 2003.

* cited by examiner

Primary Examiner—James J. Seidleck
Assistant Examiner—Sanza L. McClendon
(74) Attorney, Agent, or Firm—Sughrue Mion, PLLC

(57) ABSTRACT

To provide a polymerizable composition suitable for a lithographic printing plate precursor which can satisfy the requirements of high sensitivity, excellent storage stability and long press life and enables direct plate making from digital data from computer, etc. when recording is conducted a solid laser or semiconductor laser emitting ultraviolet ray, visible light or infrared ray and a compound therefore, the present invention relates to a photoradical polymerizable composition comprising a polyfunctional crosslinking agent having a specific structure represented by formula (I) or (II) defined in the specification.

32 Claims, No Drawings

POLYMERIZABLE COMPOSITION AND COMPOUND THEREFOR

BACKGROUND OF THE INVENTION

1. Field of the Invention

The present invention relates to a polymerizable composition which can be used for image-forming materials such as three-dimensional phototyping material, holographic material, lithographic printing plate precursor, color proof, photoresist and color filter and photo-setting resin materials such as ink, coating compound and adhesive and a polymerizable compound therefor. More particularly, the present invention relates to a polymerizable composition suitable for a so-called direct plate-making lithographic printing plate precursor which enables direct plate making from digital signal from computer, etc. using various lasers and a polymerizable compound therefor.

2. Related Art

Small-sized high output solid lasers, semiconductor lasers and gas lasers emitting ultraviolet rays, visible light or infrared rays at a wavelength of from 300 nm to 1,200 nm are easily available at present. These lasers are very useful as recording light sources in direct plate making from digital data from computer, etc.

Various recording materials sensitive to these lasers have been studied.

Firstly, examples of materials sensitive to a wavelength of not lower than 760 nm which enable recording using an infrared laser include positive-working recording materials disclosed in U.S. Pat. No. 4,708,925, and acidic catalyst-crosslinkable negative-working recording materials disclosed in JP-A-8-276558.

Secondly, examples of recording materials adapted for ultraviolet rays having a wavelength of from 300 nm to 700 nm or visible light lasers include radical polymerizable negative-working recording materials disclosed in U.S. Pat. No. 2,850,445 and JP-B-44-20189.

On the other hand, shortwave light having a wavelength of not higher than 300 nm and electron ray are important for photoresist materials. In recent years, integrated circuits have gained higher integration degree. In the production of semiconductor substrates for ULSI, it has been necessary to form ultrafine patterns having a line width of not greater than halfmicron. To this end, the recent trend is for more exposing devices for photolithrograpy to be designed to have a shorter wavelength. Thus, far ultraviolet rays and excima laser beam (XeCl, KrF, ArF, etc.) have been studied. Eventually, the formation of ultrafine patterns using electron ray has been studied. In particular, electron ray has been regarded as a promising light source for next-generation pattern formation technique.

The subject common to all these image-forming materials is how much ON-OFF of image can be expanded in the areas irradiated and unirradiated with the aforementioned various energies, that is, accomplishment of high sensitivity and storage stability of image-forming material.

There are many examples of use of high sensitivity photoradical polymerizable composition for the purpose of accomplishing the aforementioned subject. As the main components of the photoradical polymerizable composition there are used a radical polymerizable crosslinking agent and a polymer binder. As such a radical polymerizable crosslinking agent there is normally used a polyfunctional crosslinking agent which has two or more polymerizable groups per molecule to enhance its crosslinking efficiency. It is certain that such a photoradical polymerizable composition has a high sensitivity. However, when allowed to stand at high temperature and humidity, such a photoradical polymerizable composition undergoes crystallization if the crosslinking agent is solid or becomes sticky or surfaces if the crosslinking agent is liquid. It has thus been desired to develop a technique for enhancing further the storage stability of such a photoradical polymerizable composition.

On the other hand, in the case where the aforementioned photoradical polymerizable composition is applied to printing plate precursor, it is necessary that the polymerization-cured material which has been exposed to light have a high strength (long press life). A hydrogen bond interaction as attained by urethane resin has heretofore been employed for the purpose of enhancing strength. However, the use of such a hydrogen bond interaction is disadvantageous in that it reduces the flexibility of the resulting film and inhibits the migration of radicals during polymerization to reduce the sensitivity of the photoradical polymerizable composition.

SUMMARY OF THE INVENTION

It is therefore an aim of the invention to provide a polymerizable composition which can satisfy the requirements of high sensitivity, excellent storage stability and long press life as provided as a photoradical polymerization composition, which has the highest sensitivity and thus is considered promising in the art of image formation, and a compound therefor. It is another aim of the invention to provide a polymerizable composition suitable for a lithographic printing plate precursor which enables direct plate making from digital data from computer, etc. when recording is conducted a solid laser or semiconductor laser emitting ultraviolet ray, visible light or infrared ray and a compound therefor.

The inventors made extensive studies of solution to the aforementioned problems. As a result, it was found that a photoradical polymerizable composition comprising a polyfunctional crosslinking agent having a specific structure can satisfy all the requirements for high sensitivity, high storage stability and prolonged press life.

In some detail, the invention has the following constitutions.

(1) A polymerizable composition comprising at least one of compounds represented by the following general formulae (I) and (II):

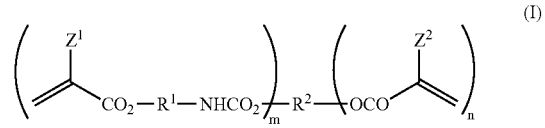

-continued

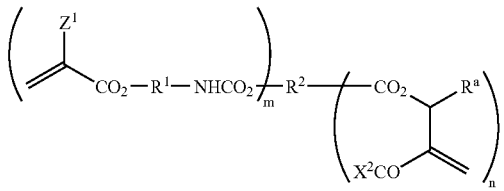
(II)

wherein $Z^1$ represents a hydrogen atom or $CH_3$; $Z^2$ represents H, $CH_3$ or $CHRbX^1$; $X^1$ and $X^2$ each independently represent a substituted oxy, amino or thio group; Ra and Rb each independently represent a hydrogen atom or hydrocarbon group; $R^1$ represents an aliphatic hydrocarbon connecting group which may have moieties connected to each other via divalent oxygen; $R^2$ represents an aliphatic hydrocarbon connecting group which may have moieties connected to each other via oxygen having a valence of (m+n); and m and n each independently represent an integer of from 1 to 5.

(2) The polymerizable composition as defined in Clause (1), comprising an alkali-soluble urethane resin incorporated therein.

(3) A compound represented by the following general formula (I) or (II):

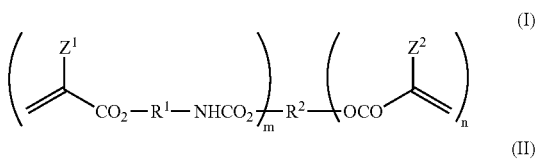
(I)

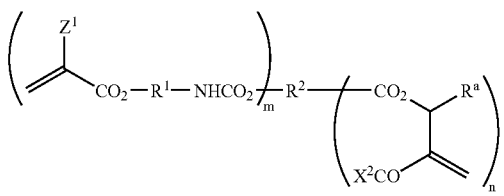
(II)

wherein $Z^1$ represents a hydrogen atom or $CH_3$; $Z^2$ represents H, $CH_3$ or $CHRbX^1$; $X^1$ and $X^2$ each independently represent a substituted oxy, amino or thio group; Ra and Rb each independently represent a hydrogen atom or hydrocarbon group; $R^1$ represents an aliphatic hydrocarbon connecting group which may have moieties connected to each other via divalent oxygen; $R^2$ represents an aliphatic hydrocarbon connecting group which may have moieties connected to each other via oxygen having a valence of (m+n); and m and n each independently represent an integer of from 1 to 5.

The mechanism by which a polymerizable composition comprising as a crosslinking agent at least one of compounds represented by the aforementioned general formulae (I) and (II) of the invention can satisfy all the requirements for high sensitivity, high storage stability and prolonged press life is unknown. However, it is thought that a high compatibility with resin attributed to the specific structure of the molecule of the crosslinking agent and the self-cohesiveness of the crosslinking agent itself act on the mechanism. In some detail, it is presumed that the high compatibility with resin and the high self-cohesiveness cause the crosslinking agent to form ultrafinely divided domains that are compatible with the resin. As a result, the storage stability is enhanced. Further, the spatial distance between the polymerizable groups is reduced, causing the disadvantage of migration of radicals due to interaction of hydrogen bond with the urethane resin to turn to an advantage. Thus, the trade-off between enhancement of sensitivity and prolongation of press life can be eliminated.

The polymerizable composition of the invention also has an unprecedentedly great advantage of enhancement of sensitivity that it has not only an enhanced exposure sensitivity but also has little temperature dependence that makes it possible to drastically raise the hardness of the product without effecting any treatment such as heating after expopsure (in normal polymerization reactions, when the reaction temperature is raised, the polymerization reaction proceeds further, raising the hardness of the product).

In particular, a polymerizable composition can be provided which can be used as a lithographic printing plate precursor on which digital data from computer or the like can be directly recorded using a solid laser or semiconductor laser emitting ultraviolet rays, visible light or infrared rays to make a printing plate.

The polymerizable composition of the invention will be further described hereinafter.

<Crosslinking Agents Represented By the General Formulae (I) and (II) of the Invention>

The polymerizable composition of the invention comprises a polyfunctional crosslinking agent incorporated therein having a plurality of ethylenically polymerizable groups having a structure represented by the following general formula (I) or (II) per molecule:

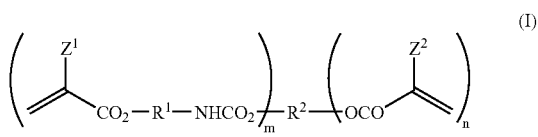
(I)

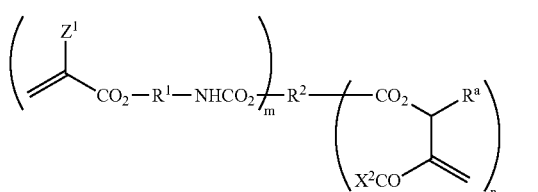
(II)

wherein $Z^1$ represents a hydrogen atom or $CH_3$; $Z^2$ represents H, $CH_3$ or $CHRbX^1$; $X^1$ and $X^2$ each independently represent a substituted oxy, amino or thio group; Ra and Rb each independently represent a hydrogen atom or hydrocarbon group; $R^1$ represents a divalent aliphatic hydrocarbon connecting group, which may include at least one —O— connecting group; $R^2$ represents an aliphatic hydrocarbon connecting group having a valence of (m+n), which may include at least one —O— connecting group; and m and n each independently represent an integer of from 1 to 5.

Examples of the various substituents in the aliphatic hydrocarbon connecting groups of $X^1$, $X^2$, $R^1$ and $R^2$ and the hydrocarbon groups of $R^a$ and $R^b$ in the general formulae (I) and (II) will be given below.

$X^1$ and $X^2$ each represent a substituted oxy, amino or thio group.

The aliphatic hydrocarbon connecting group of $R^1$ is a divalent connecting group obtained by removing one hydrogen atom each from a substituted or unsubstituted alkyl group, a substituted or unsubstituted alkenyl group, or a substituted or unsubstituted alkenyl group, preferably from a substituted or unsubstituted alkyl group.

The aliphatic hydrocarbon connecting group of $R^2$ is a connecting group having a valence of (m+n), obtained by removing a number of (m+n−1) of hydrogen atom(s) each from a substituted or unsubstituted alkyl group, a substituted or unsubstituted alkenyl group, or a substituted or unsubstituted alkenyl group, preferably from a substituted or unsubstituted alkyl group.

The hydrocarbon groups of $R^a$ and $R^b$ each are a hydrocarbon group which may have substituents or may contain an unsaturated bond(s).

Examples of the aforementioned hydrocarbon group which may have substituents and may contain unsaturated bonds include alkyl groups, substituted alkyl groups, aryl groups, substituted aryl groups, alkenyl groups, substituted alkenyl groups, alkynyl groups, and substituted alkynyl groups.

The substituents that can be used as $X^1$, $X^2$, $R^a$ and $R^b$ mentioned above or that can be used as substituents for $X^1$, $X^2$, $R^a$ and $R^b$ are generally explained in detail below.

Examples of the alkyl groups include straight-chain, branched and cyclic alkyl groups each having from 1 to 20 carbon atoms. Specific examples of these alkyl groups include methyl group, ethyl group, propyl group, butyl group, pentyl group, hexyl group, heptyl group, octyl group, nonyl group, decyl group, undecyl group, dodecyl group, tridecyl group, hexadecyl group, octadecyl group, eicosyl group, isopropyl group, isobutyl group, s-butyl group, t-butyl group, isopentyl group, neopentyl group, 1-methylbutyl group, isohexyl group, 2-ethylhexyl group, 2-methylhexyl group, cyclohexyl group, cyclopentyl group, and 2-norbornyl group. Preferred among these alkyl groups are straight-chain alkyl groups each having from 1 to 12 carbon atoms, branched alkyl groups each having from 3 to 12 carbon atoms and cyclic alkyl groups each having from 5 to 10 carbon atoms.

The substituted alkyl groups are each formed by substituents and an alkylene group. As the substituents there are monovalent non-metallic atomic groups except hydrogen. Preferred examples of these monovalent non-metallic atomic groups include halogen atoms (e.g., —F, —Br, —Cl, —I), hydroxyl groups, alkoxy groups, aryloxy groups, mercapto groups, alkylthio groups, arylthio groups, alkyldithio groups, aryldithio groups, amino groups, N-alkylamino groups, N,N-dialkylamino groups, N-arylamino groups, N,N-diarylamino groups, N-alkyl-N-arylamino groups, acyloxy groups, carbamoyloxy groups, N-alkylcarbamoyloxy groups, N-arylcarbamoyloxy groups, N,N-dialkylcarbamoyloxy groups, N,N-diarylcarbamoyloxy groups, N-alkyl-N-arylcarbamoyloxy groups, alkylsulfoxy groups, arylsulfoxy groups, acylthio groups, acylamino groups, N-alkylacylamino groups, N-arylacrylamino groups, ureido groups, N'-alkylureido groups, N',N'-dialkylureido groups, N'-arylureido groups, N',N'-diarylureido groups, N'-alkyl-N'-arylureido groups, N-alkylureido groups, N-arylureido groups, N'-alkyl-N-alkylureido groups, N'-alkyl-N-arylureido groups, N',N'-dialkyl-N-alkylureuido groups, N',N'-dialkyl-N-arylureido groups, N'-aryl-N-alkylureido groups, N'-aryl-N-arylureido groups, N',N'-diaryl-N-alkylureido groups, N',N'-diaryl-N-arylureido groups, N'-alkyl-N'-aryl-N-alkylureido groups, N'-alkyl-N'-aryl-N-arylureido groups, alkoxycarbonylamino groups, aryloxycarbonylamino groups, N-alkyl-N-alkoxycarbonylamino groups, N-alkyl-N-aryloxycarbonylamino groups, N-aryl-N-alkoxycarbonylamino groups, N-aryl-N-aryloxycarbonylamino groups, formyl groups, acyl groups, carboxyl groups and conjugated bases thereof (hereinafter referred to as "carboxylate"), alkoxycarbonyl groups, aryloxycarbonyl groups, carbamoyl groups, N-alkylcarbamoyl groups, N,N-dialkylcarbamoyl groups, N-arylcarbamoyl groups, N,N-diarylcarbamoyl groups, N-alkyl-N-arylcarbamoyl groups, alkylsulfinyl groups, arylsulfinyl groups, alkylsulfonyl groups, arylsulfonyl groups, sulfo group (—$SO_3H$) and conjugated bases thereof (hereinafter referred to as "sulfonato group"), alkoxysulfonyl groups, aryloxysulfonyl groups, sulfinamoyl groups, N-alkylsulfinamoyl groups, N,N-dialkylsulfinamoyl groups, N-arylsulfinamoyl groups, N,N-diarylsulfinamoyl groups, N-alkyl-N-arylsulfinamoyl groups, sulfamoyl groups, N-alkylsulfamoyl groups, N,N-dialkylsulfamoyl groups, N-arylsulfamoyl groups, N,N-diarylsulfamoyl groups, N-alkyl-N-arylsulfamoyl groups, N-acylsulfamoyl groups and conjugated bases thereof, N-alkylsulfonylsulfamoyl groups (—$SO_2NHSO_2$) (alkyl)) and conjugated bases thereof, N-arylsulfonylsulfamoyl groups (—$SO_2NHSO_2$ (allyl)) and conjugated bases thereof, N-alkylsulfonylcarbamoyl groups (—$CONHSO_2$ (alkyl)) and conjugated bases thereof, N-arylsulfonylcarbamonyl groups (—$CONHSO_2$ (allyl)) and conjugated bases thereof, alkoxysilyl groups (—$Si(Oalkyl)_3$), aryloxysilyl groups (—$SiOalkyl)_3$), hydroxyl groups (—$Si(OH)_3$) and conjugated bases thereof, hydroxysilyl groups (—$Si(OH)_3$) and conjugated bases thereof, phosphono groups (—$PO_3H_2$) and conjugated bases thereof (hereinafter referred to as "phosphonato group"), dialkylphosphono groups (—$PO_3(alkyl)_2$), diarylphosphono groups (—$PO_3(aryl)_2$), alkylarylphosphono groups (—$PO_3$ (alkyl)(aryl)), monoalkylphosphono groups (—$PO_3H$ (alkyl)) and conjugated bases thereof (hereinafter referred to as "alkylphosphonato group"), monoarylphosphono groups (—$PO_3H$ (aryl)) and conjugated bases thereof (hereinafter referred to as "arylphosphonato group"), phosphonoxy groups (—$OPO_3H_2$) and conjugated bases thereof (hereinafter referred to as "phosphonatoxy group"), dialkylphosphonooxy groups (—$OPO_3(alkyl)_2$), diarylphosphonoxy groups (—$OPO_3(aryl)_2$), alkylarylphosphonoxy (—$OPO_3(alkyl)(aryl)$), monoalkylphosphonoxy groups (—$OPO_3H(alkyl)$) and conjugated bases thereof (hereinafter referred to as "alkylphosphonatoxy group"), monoarylphosphonoxy groups (—$OPO_3H(aryl)$) and conjugated bases thereof (hereinafter referred to as "arylphosphonatoxy group"), cyano groups, nitro groups, aryl groups, alkenyl groups, and alkynyl groups.

Specific examples of the alkyl groups as substituents include those described above. Specific examples of the aryl groups as substituents include phenyl group, biphenyl group, naphthyl group, tolyl group, xylyl group, mesityl group, cumenyl group, fluorophenyl group, chlorophenyl group, bromophenyl group, chloromethylphenyl group, hydroxyphenyl group, methoxyphenyl group, ethoxyphenyl group, phenoxyphenyl group, acetoxyphenyl group, benzoyloxyphenyl group, methylthiophenyl group, phenylthiophenyl group, methylaminophenyl group, dimethylaminophenyl group, acetylaminophenyl group, carboxyphenyl group, methoxycarbonylphenyl group, ethoxycarbonylphenyl group, phenoxycarbonylphenyl group, N-phenylcarbamoylphenyl group, phenyl group, nitrophenyl group, cyanophenyl group, sulfophenyl group, sulfonatophenyl group, phosphonophenyl group, and phosphonatophenyl group. Examples of the alkenyl groups as substituents include vinyl group, 1-propenyl group, 1-butenyl group, cinnamyl group, and 2-chloro-1-ethenyl group. Examples of the alkynyl groups as substituents include ethinyl group, 1-propinyl group, 1-butinyl group, trimethylsilylethinyl group, and phenylethinyl group.

Examples of the aforementioned acyl group (R₄CO—) include those wherein R4 is a hydrogen atom or the aforementioned alkyl, aryl, alkenyl or alkynyl group.

On the other hand, as the alkylene group in the substituted alkyl group there may be used a divalent organic residue obtained by removing any one of the hydrogen atoms on the aforementioned alkyl group having from 1 to 20 carbon atoms, preferably a straight-chain alkylene group having from 1 to 12 carbon atoms, branched alkylene group having from 3 to 12 carbon atoms or cyclic alkylene group having from 5 to 10 carbon atoms. Specific preferred examples of the substituted alkyl group include chloromethyl group, bromomethyl group, 2-chloroethyl group, trifluoromethyl group, methoxymethyl group, methoxyethoxyethyl group, allyloxymethyl group, phenoxymethyl group, methylthiomethyl group, tolylthiomethyl group, ethylaminoethyl group, diethylaminopropyl group, morpholinoopropyl group, acetyloxymethyl group, benzoyloxymethyl group, N-cyclohexylcarbamoyloxyethyl group, N-phenylcarbamoyloxyethyl group, acetylaminoethyl group, N-methylbenzoylaminopropyl group, 2-oxoethyl group, 2-oxopropyl group, carboxypropyl group, methoxycarbonylethyl group, methoxycarbonylmethyl group, methoxycarbonylbutyl group, ethoxycarbonylmethyl group, butoxycarbonylmethyl group, allyloxycarbonylmethyl group, benzyloxycarbonylmethyl group, methoxycarbonylphenylmethyl group, trichloromethylcarbonylmethyl group, allyloxycarbonylbutyl group, chlorophenoxycarbonylmethyl group, carbamoylmethyl group, N-methylcarbamoylethyl group, N,N-dipropylcarbamoylmethyl group, N-(methoxyphenyl)carbamoylethyl group, N-methyl-N-(sulfophenyl)carbamoylmethyl group, sulfopropyl group, sulfobutyl group, sulfonatobutyl group, sulfamoylbutyl group, N-ethylsulfamoylmethyl group, N,N-dipropylsulfamoylpropyl group, N-tolylsulfamoylpropyl group, N-methyl-N-(phosphonophenyl)sulfamoyloctyl group,

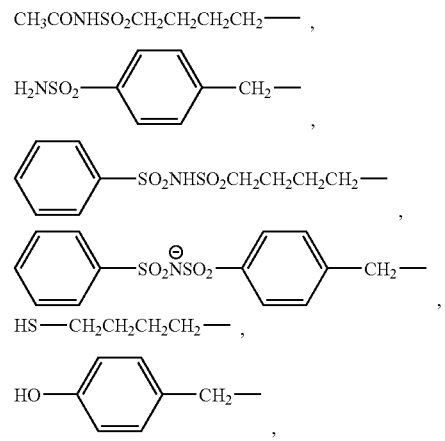

phosphonobutyl group, phosphonatohexyl group, diethylphosphonobutyl group, diphenylphosphonopropyl group, methylphosphonobutyl group, methylphosphonatobutyl group, tolylphosphonohexyl group, tolylphosphonatohexyl group, phosphonoxypropyl group, phosphonatoxybutyl group, benzyl group, phenetyl group, α-methylbenzyl group, 1-methyl-1-phenylethyl group, p-methylbenzyl group, cinnamyl group, allyl group, 1-propenylmethyl group, 2-butenyl group, 2-methylallyl group, 2-methylpropenylmethyl group, 2-propinyl group, 2-butinyl group, and 3-butinyl group.

Examples of the aryl group include condensed ring formed by 1 to 3 benzene rings, and condensed ring formed by a benzene ring and a 5-membered unsaturated ring. Specific examples of these condensed rings include phenyl group, naphthyl group, anthryl group, phenanthryl group, indenyl group, acetobutenyl group, and fluorenyl group. Preferred among these condensed rings are phenyl group and naphthyl group.

The substituted aryl group is an aryl group having substituents bonded thereto. As such a substituted aryl group there may be used one having a monovalent non-metallic atomic group except hydrogen on the ring-forming carbon atoms in the aforementioned aryl group as a substituent. Preferred examples of such a substituent include the aforementioned alkyl groups and substituted alkyl groups, and those described above as substituents on the substituted alkyl groups. Specific preferred examples of these substituted aryl groups include biphenyl group, tolyl group, xylyl group, mesityl group, cumenyl group, chlorophenyl group, bromophenyl group, fluorophenyl group, chloromethylphenyl group, trifluoromethylphenyl group, hydroxyphenyl group, methoxyphenyl group, methoxyethoxyphenyl group, allyloxyphenyl group, phenoxyphenyl group, methylthiophenyl group, tolylthiophenyl group, phenylthiophenyl group, ethylaminophenyl group, diethylaminophenyl group, morpholinophenyl group, acetyloxyphenyl group, benzoyloxyphenyl group, N-cyclohexylcarbamoyloxyphenyl group, N-phenylcarbamoyloxyphenyl group, acetylaminophenyl group, N-methylbenzoylaminophenyl group, carboxyphenyl group, methoxycarbonylphenyl group, allyloxycarbonylphenyl group, chlorophenoxycarbonylphenyl group, carbamoylphenyl group, N-methylcarbamoylphenyl group, N,N-dipropylcarbamoylphenyl group, N-(methoxyphenyl)carbamoylphenyl group, N-methyl-N-(sulfonylphenyl)carbamoylphenyl group, sulfophenyl group, sulfonatophenyl group, sulfamoylphenyl group, N-ethylsulfamoylphenyl group, N,N-dipropylsulfamoyl phenyl group, N-tolylsulfamoylphenyl group, N-methyl-N-(phosphonophenyl)sulfamoylphenyl group, phosphonophenyl group, phosphonatophenyl group, diethylphosphonophenyl group, diphenylphosphonophenyl group, methylphosphonophenyl group, methylphosphonatophenyl group, tolylphosphonatophenyl group, tolylphosphonatophenyl group, allyl group, 1-propenylmethyl group, 2-butenyl group, 2-methylallylphenyl group, 2-methylpropenylphenyl group, 2-propinylphenyl group, 2-butinylphenyl group, and 3-butinylphenyl group.

Examples of the alkenyl group include those described above. The substituted alkenyl group is obtained by substituting hydrogen atoms on an alkenyl group by substituents. As these substituents there may be used those described above with reference to the substituted alkyl group. On the other hand, as the alkenyl group there may be used the aforementioned alkenyl group. Preferred examples of the substituted alkenyl group include the following compounds:

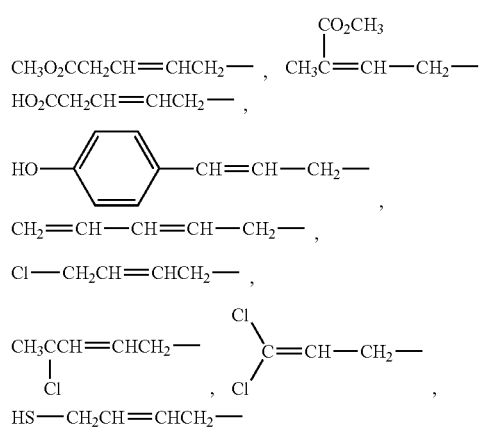

Examples of the alkynyl group include those described above. The substituted alkynyl group is obtained by substituting hydrogen atoms on an alkynyl group by substitutents. As these substituents there may be used those described above with reference to the substituted alkyl group. On the other hand, as the alkynyl group there may be used the aforementioned alkynyl group.

The heterocyclic group is a monovalent group obtained by removing one hydrogen atom from a heterocycle or a monovalent group (substituted heterocyclic group) obtained by removing another hydrogen atom from the monovalent group and bonding a substituent described above with reference to the substituted alkyl group to the monovalent group in the position of the hydrogen position. Preferred examples of the heterocycle include the following compounds:

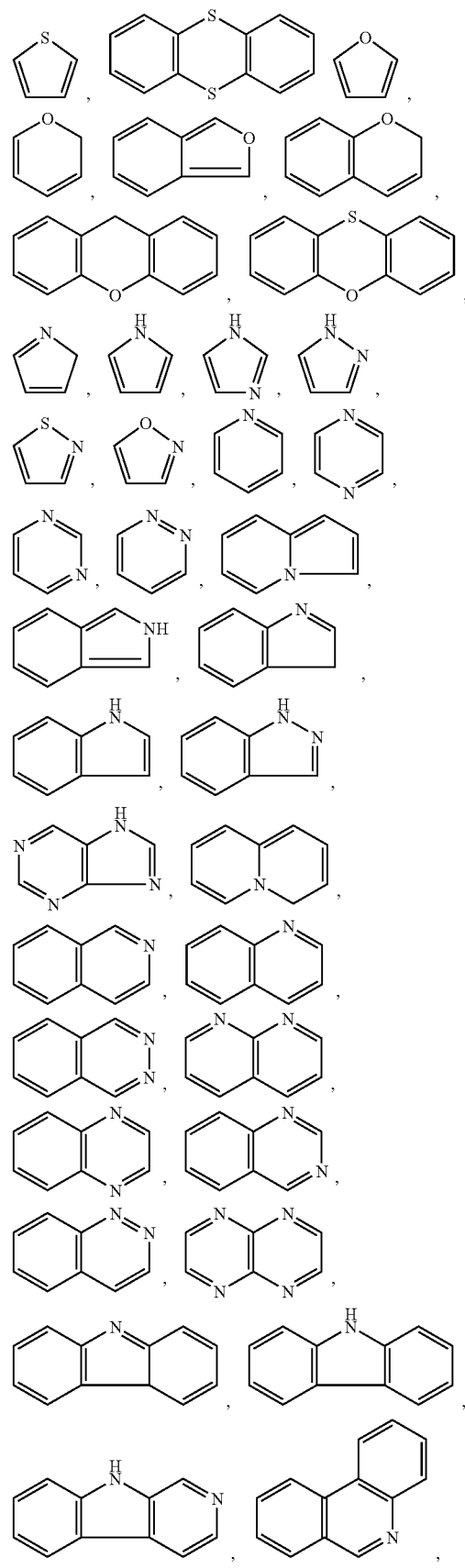

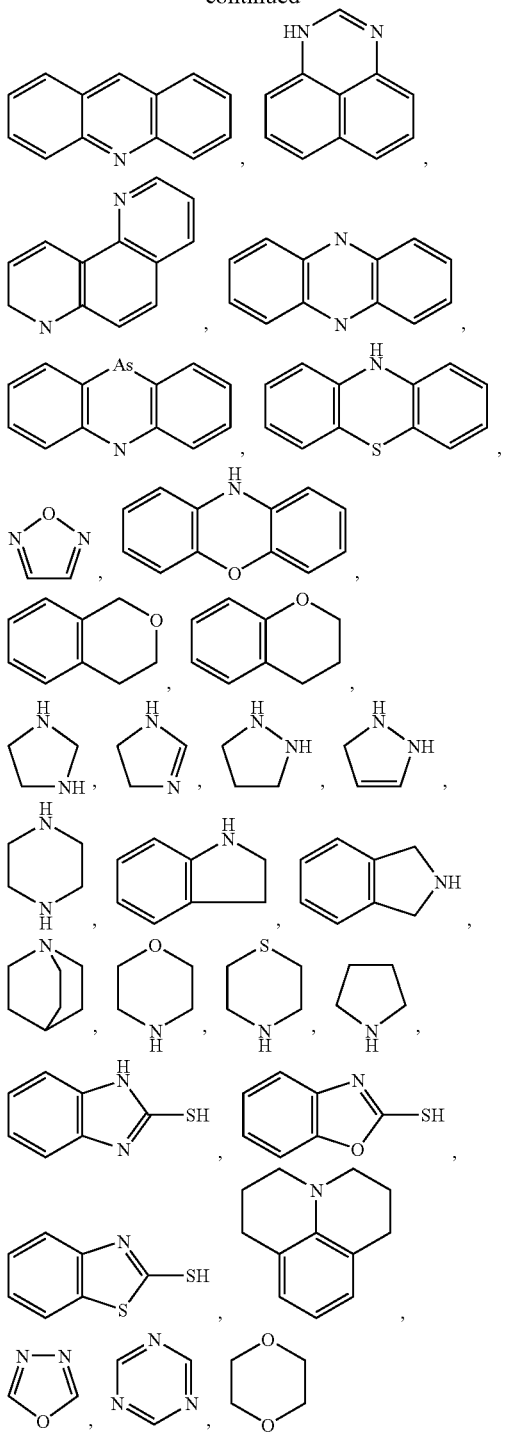

of the alkyl group and aryl group in these substituted oxy groups include those exemplified above as alkyl groups, substituted alkyl groups, alkyl groups and substituted aryl groups. Examples of the acyl group ($R_6CO—$) in the acyloxy group include those wherein $R_6$ is the aforementioned alkyl group, substituted alkyl group, aryl group or substituted aryl group. Preferred among these substitutents are alkoxy group, aryloxy group, acyloxy group, and arylsulfoxy group. Specific preferred examples of the substituted oxy groups include methoxy group, ethoxy group, propyloxy group, isopropyloxy group, butyloxy group, pentyloxy group, hexyloxy group, dodecyloxy group, benzyloxy group, allyloxy group, phenethyloxy group, carboxyethyl group, methoxycarbonylethyloxy group, ethoxycarbonylethyl oxy group, methoxyethoxy group, phenoxyethoxy group, methoxyethoxyethoxy group, ethoxyethoxyethoxy group, morpholinoethoxy group, morpholinopropyloxy group, aryloxyethoxyethoxy group, phenoxy group, tolyloxy group, xylyloxy group, mesityloxy group, cumenyloxy group, methoxyphenyloxy group, ethoxyphenyloxy group, chlorophenyloxy group, bromophenyloxy group, acetyloxy group, benzoyloxy group, naphthyloxy group, phenylsulfonyloxy group, phosphonoxy group, and phosphonoxy group.

As the substituted thio group ($R_7S—$) there may be used one wherein $R_7$ is a monovalent non-metallic atomic group except hydrogen atom. Preferred examples of the substituted thio group include alkylthio group, arylthio group, alkyldithio group, aryldithio group, and acylthio group. Examples of the alkyl group and aryl group in these substituted thio groups include those exemplified above as alkyl groups, substituted alkyl groups, alkyl groups and substituted aryl groups. $R_6$ in the acyl group ($R_6CO—$) in the acylthio group is as defined above. Preferred among these substituted thio groups are alkylthio group and arylthio group. Preferred examples of the substituted thio group include methylthio group, ethylthio group, phenylthio group, ethoxyethylthio group, carboxyethylthio group, and methoxycarbonylthio group.

As the substituted amino group ($R_8NH—$, $(R_9)(R_{10})N—$) there may be used one where $R_8$, $R_9$ and $R_{10}$ each are a monovalent non-metallic atomic group except hydrogen atom. Preferred examples of the substituted amino group include N-alkylamino groups, N,N-dialkylamino groups, N-arylamino groups, N,N-diarylamino groups, N-alkyl-N-arylamino groups, acylamino groups, N-alkylacylamino groups, N-arylacylamino groups, ureido groups, N'-alkylyureido groups, N',N'-dialkylureido groups, N'-arylureido groups, N',N'-diarylureido groups, N'-alkyl-N'-arylureido groups, N-alkylureido groups, N-arylureido groups, N'-alkyl-N-alkylureido groups, N'-alkyl-N-arylureido groups, N',N'-dialkyl-N-alkylureuido groups, N',N'-dialkyl-N-arylureido groups, N'-aryl-N-alkylureido groups, N'-aryl-N-arylureido groups, N',N'-diaryl-N-alkylureido groups, N',N'-diaryl-N-arylureido groups, N'-alkyl-N'-aryl-N-alkylureido groups, N'-alkyl-N'-aryl-N-arylureido groups, alkoxycarbonylamino groups, aryloxycarbonylamino groups, N-alkyl-N-alkoxycarbonylamino groups, N-alkyl-N-aryloxycarbonylamino groups, N-aryl-N-alkoxycarbonylamino groups, N-aryl-N-aryloxycarbonylamino groups, and N-aryl-N-aryloxycarbonylamino groups.

As the substituted oxy group ($R_5O—$) there may be used one wherein $R_5$ is a monovalent non-metallic atomic group except hydrogen atom. Preferred examples of the substituted oxy group include alkoxy groups, aryloxy groups, acyloxy group, carbamoyloxy group, N-alkylcarbamoyloxy group, N-arylcarbamoyloxy group, N,N-dialkylcarbamoyloxy group, N,N-diarylcarbamoyloxy group, N-alkyl-N-arylcarbamoyloxy group, alkylsulfoxy group, arylsulfoxy group, phosphonoxy group, and phosphonatoxy group. Examples Examples of the alkyl group and aryl group in these substituted amino groups include those exemplified above as alkyl groups, substituted alkyl groups, alkyl groups and substituted aryl groups. $R_6$ in the acyl group ($R_6CO—$) in the acylamino group, N-alkylacylamino group and N-arylacylamino group is as defined above. Preferred among these substituted amino groups are N-alkylamino groups, N,N-dialkylamino groups, N-arylamino groups, and acylamino groups. Specific preferred examples of the substituted amino group include methylamino group, ethylamino group, diethylamino group, morpholino group, piperidino group, pyrrolidino group, phenylamino group, benzoylamino group, and acetylamino group.

Specific examples of the compounds (crosslinking agent) having structures represented by the general formulae (I) and (II) will be given below.

i) Compound Examples of Formula (I)

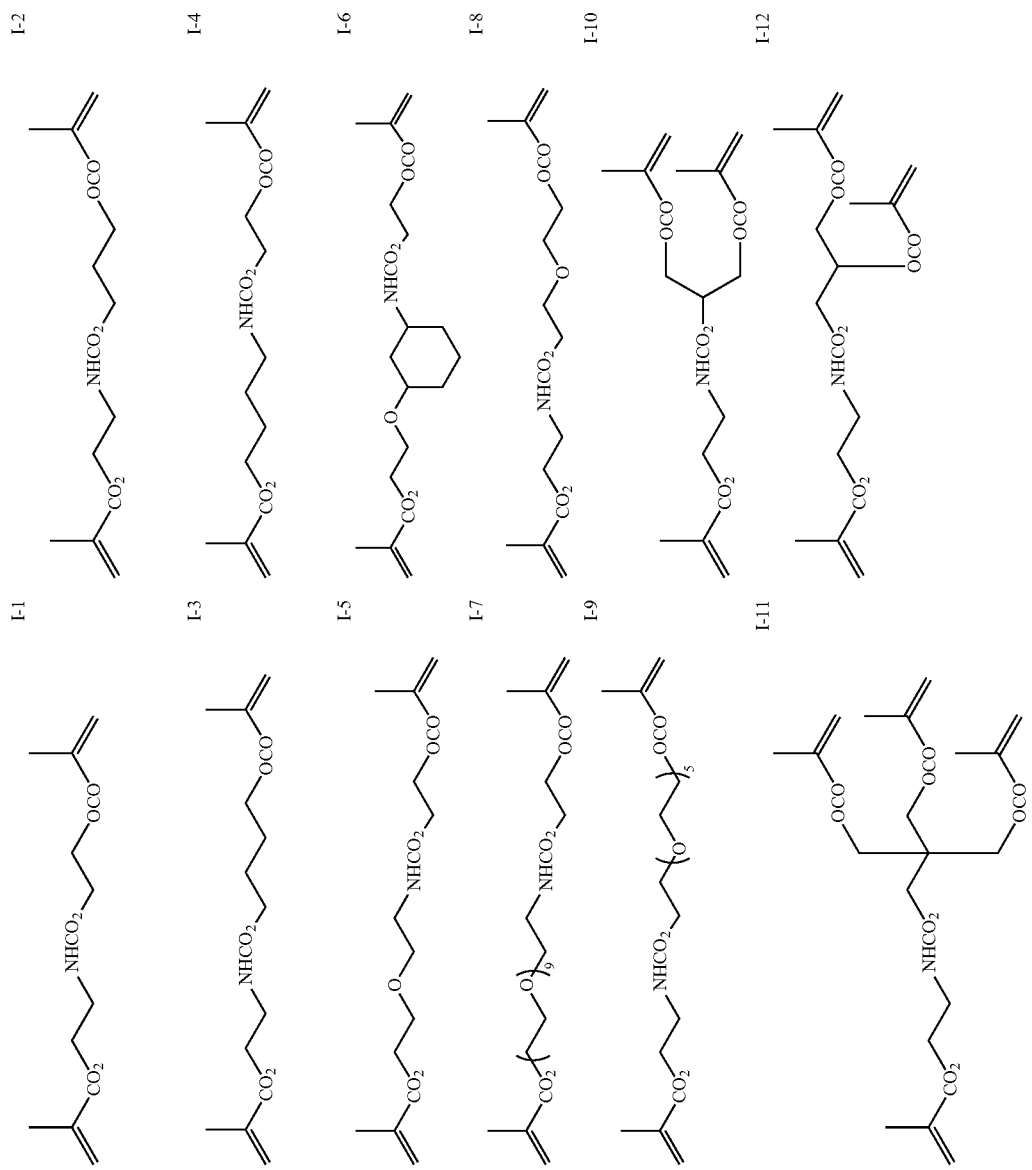

-continued
I-13
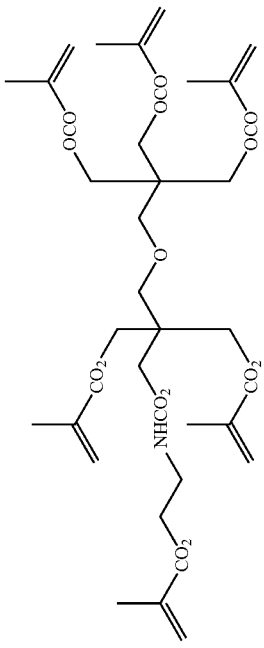
I-14
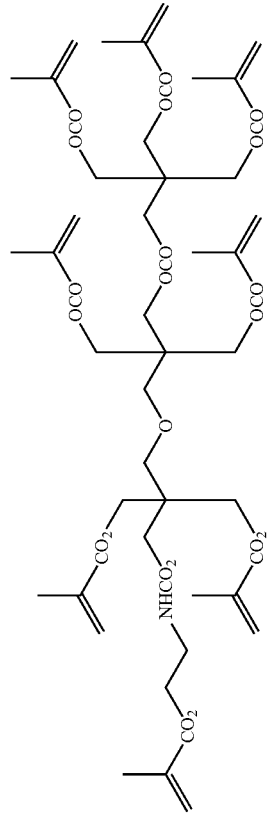
I-16
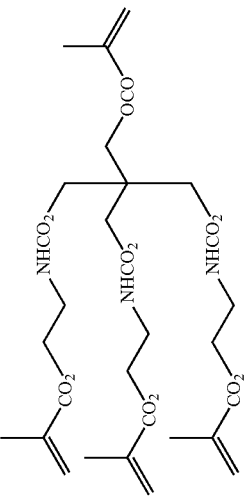
I-15
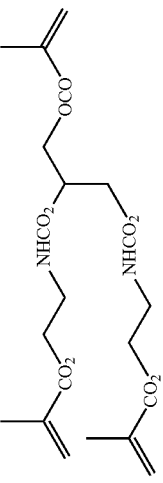

-continued
I-17
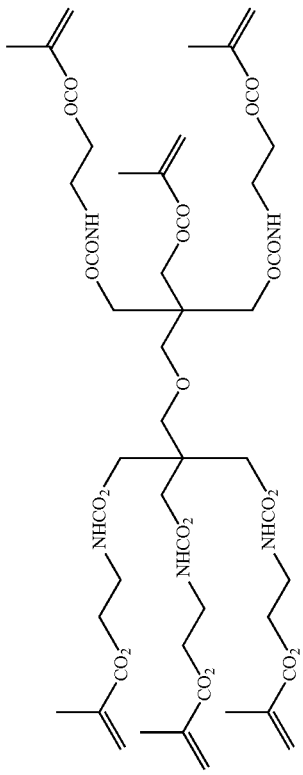
I-18
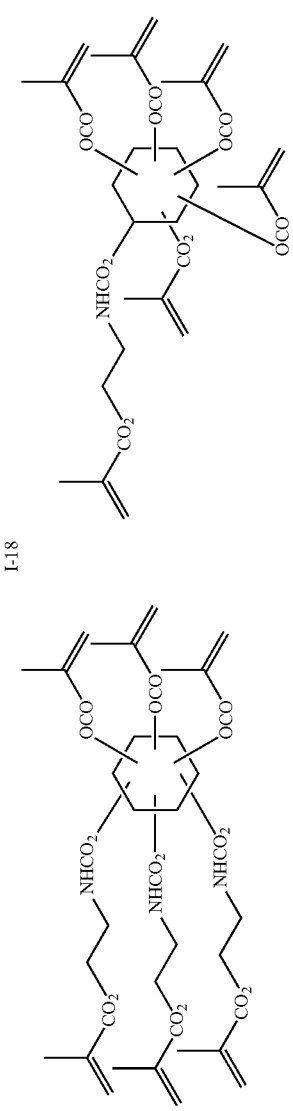
I-19
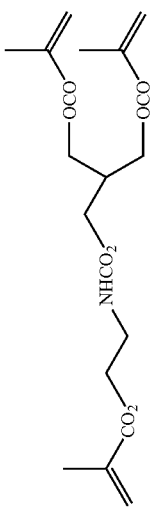
I-20
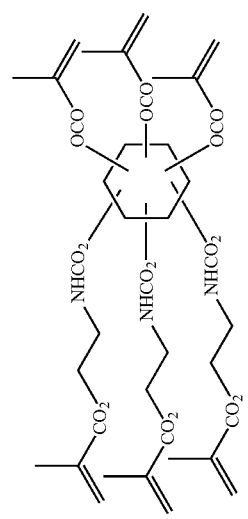
I-21
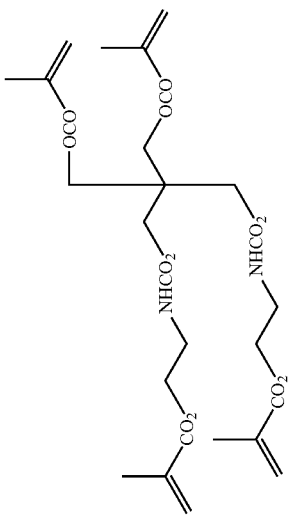

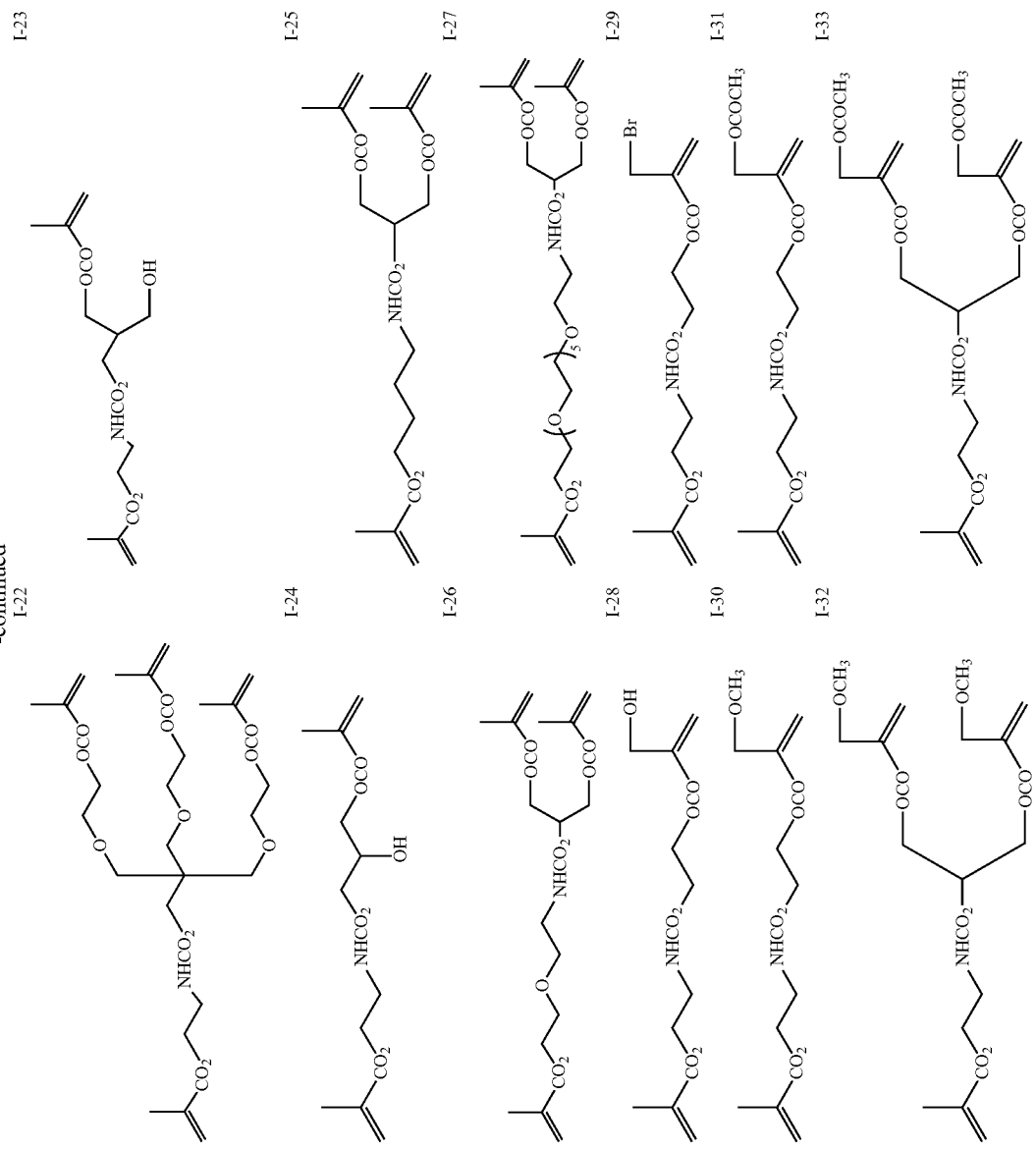

-continued
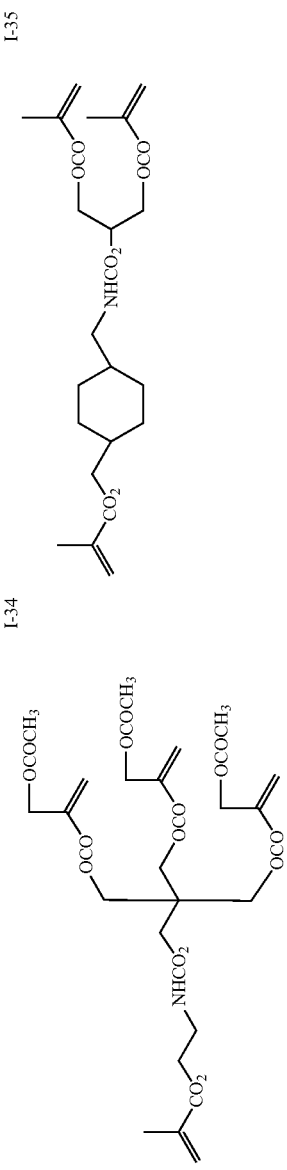
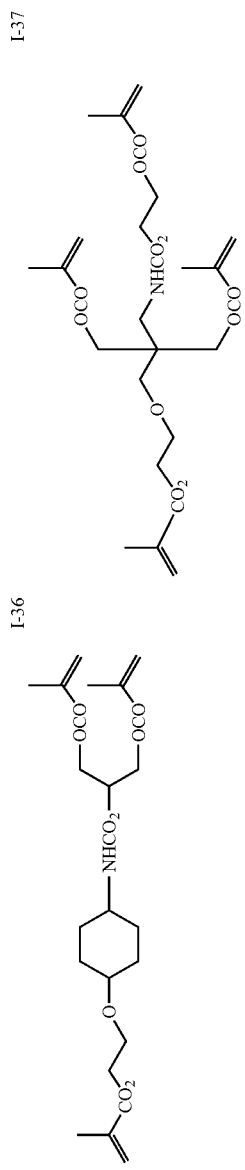
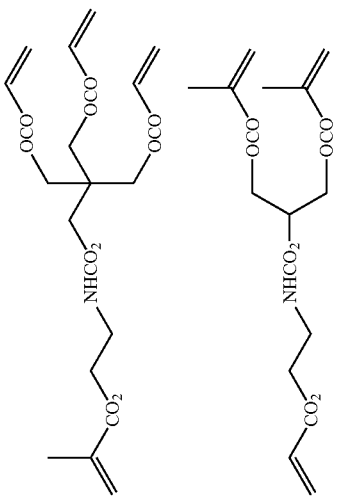
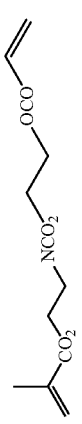

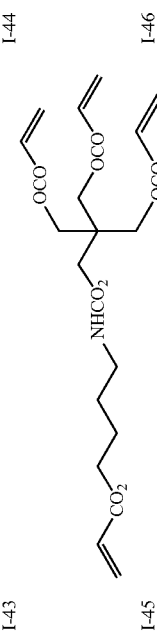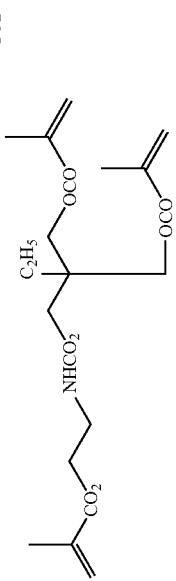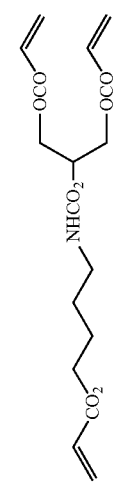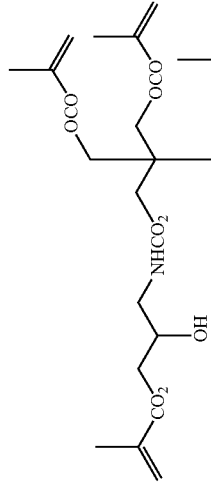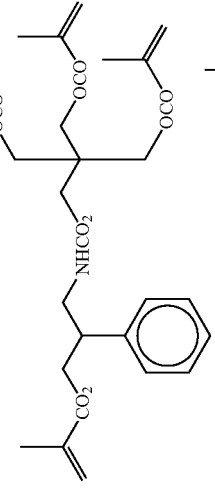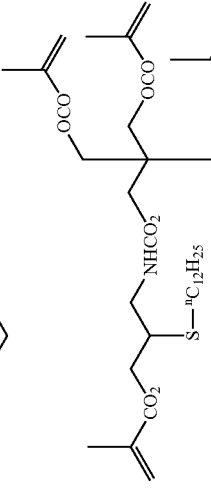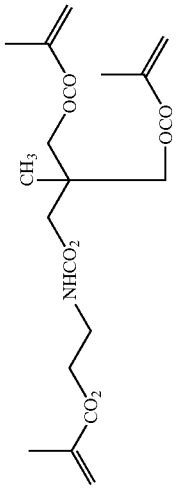

ii) Compound Examples of Formula (II)
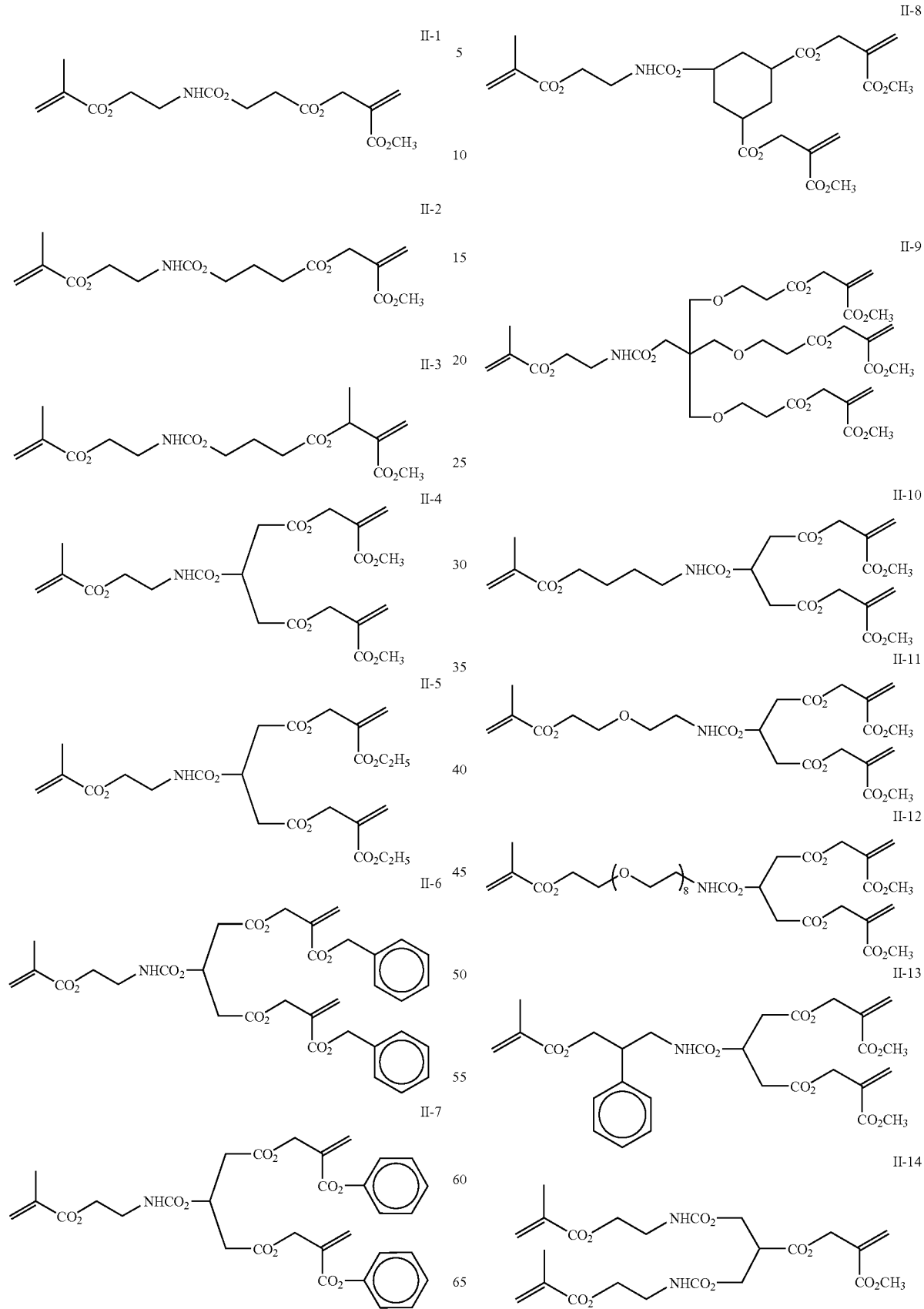

-continued
II-15
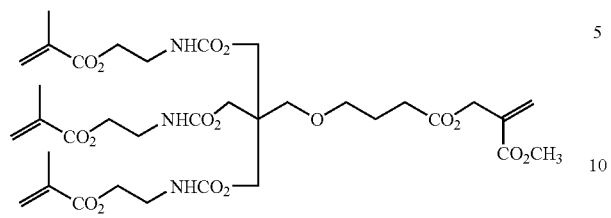
II-16
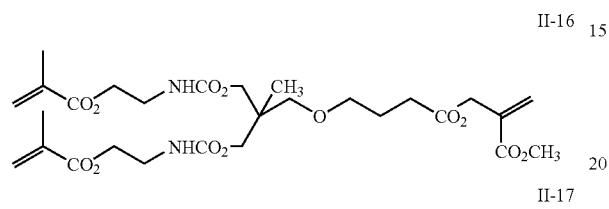
II-17
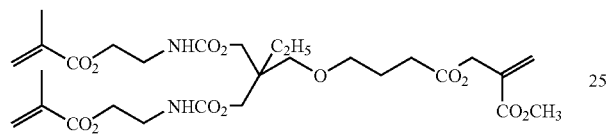
II-18
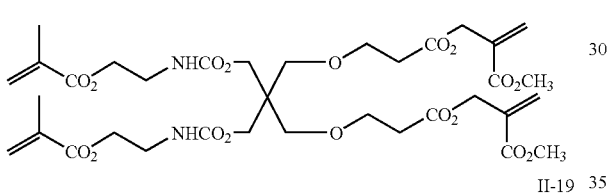
II-19
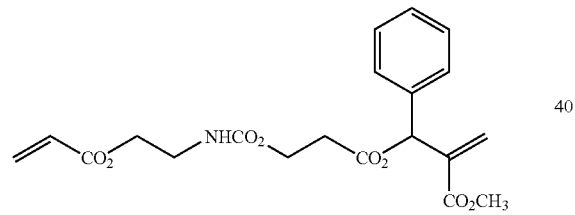
II-20
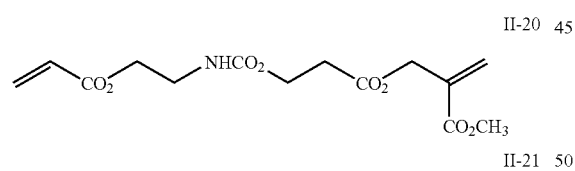
II-21
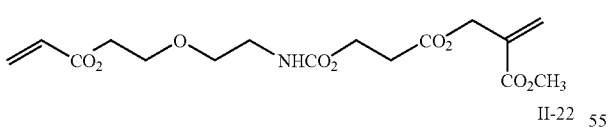
II-22
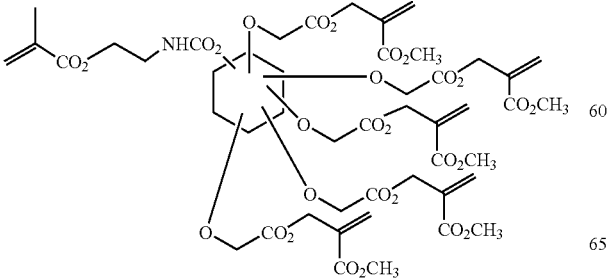
-continued
II-23
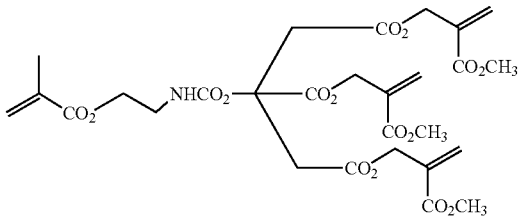
II-24
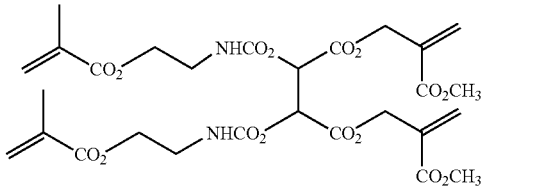
II-25
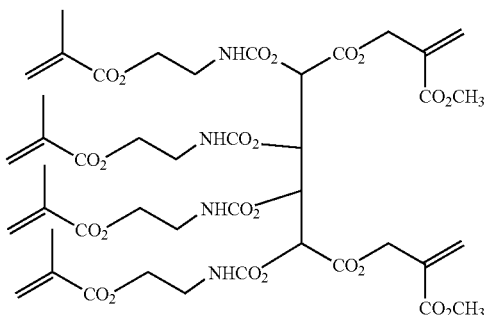
II-26
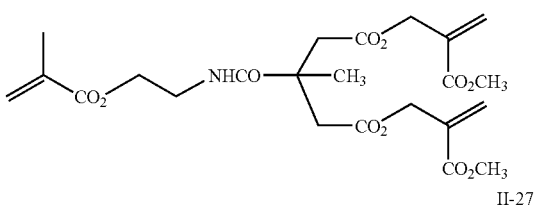
II-27
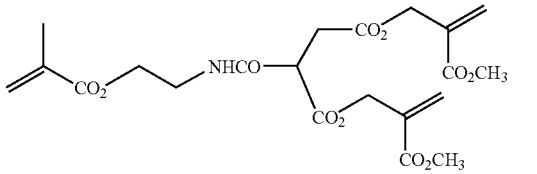
II-28
As the polyfunctional crosslinking agents represented by the general formulae (I) and (II) there may be used preferably those of the general formulae (I) and (II) wherein $R^2$ is a connecting group having a valence of from 3 to 6 ($3 \leq (m+n) \leq 6$), more preferably any selected from the group consisting of the following trivalent or tetravalent (m+n: 3 or 4) connecting groups of the general formula (III), and it is most desired that $Z^1$ and $Z^2$ are $CH_3$ at the same time.

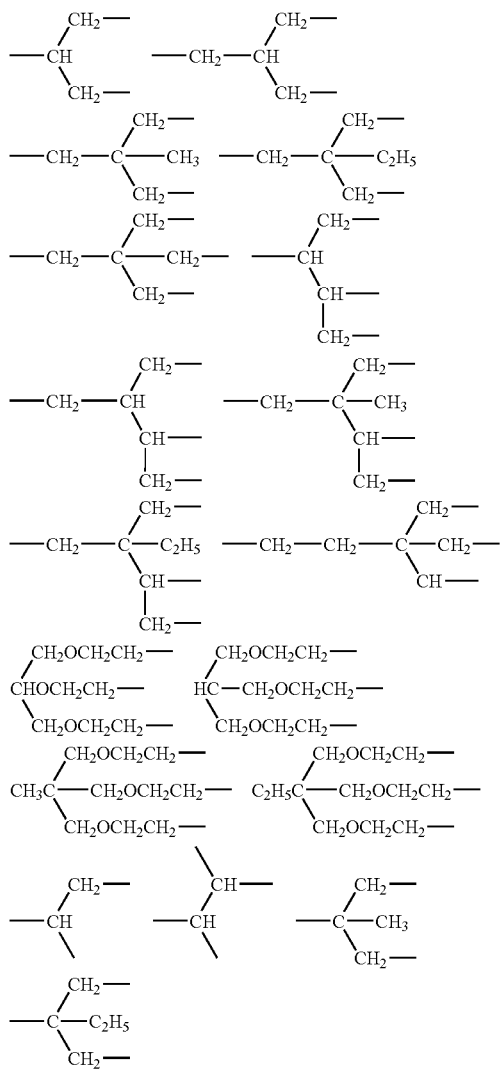

The polymerizable composition of the invention comprises as crosslinking agents having a plurality of addition-polymerizable ethylenically polymerizable groups crosslinking agents represented by the aforementioned general formulae (I) and (II), singly or in admixture of two or more thereof or with known compounds having addition-polymerizable ethylenically unsaturated bonds described below.

Examples of the known compounds having addition-polymerizable ethylenically unsaturated bonds include ester of unsaturated carboxylic acid (e.g., acrylic acid, methacrylic acid, itaconic acid, crotonic acid, isocrotonic acid, maleic acid) with aliphatic polyvalent alcohol compound, and amide of the aforementioned unsaturated carboxylic acid with aliphatic polyvalent amine compound.

Examples of the ester of aliphatic polyvalent alcohol compound with unsaturated carboxylic acid as a monomer include acrylic acid esters such as ethylene glycol diacrylate, triethylene glycol diacrylate, 1,3-butanediol diacrylate, tetramethylene glycol diacrylate, propylene glycol diacrylate, neopentyl glycol diacrylate, trimethylol propane triacrylate, trimethylolpropane tri(acryloyloxy propyl)ether, trimethylolethane triacrylate, hexanediol diacrylate, 1,4-cyclohexanediol diacrylate, tetraethylene glycol diacrylate, pentaerythritol diacrylate, pentaerythritol triacrylate, pentaerythritol tetraacrylate, dipentaerythritol diacrylate, dipentaerythritol hexaacrylate, sorbitol triacrylate, sorbitol tetraacrylate, sorbitol pentaacrylate, sorbitol hexaacrylate, tri(acryloyloxyethyl)isocyanurate and polyester acrylate oligomer.

Specific examples of methacrylic acid esters as esters of aliphatic polyvalent alcohol compound with unsaturated carboxylic acid include methacrylic acid esters such as tetramethylene glycol dimethacrylate, triethylene glycol dimethacrylate, neopentyl glycol dimethacrylate, trimethylolpropane trimethacrylate, trimethylolethane trimethacrylate, ethylene glycol dimethacrylate, 1,3-butanediol dimethacrylate, hexanediol dimethacrylate, pentaerythritol dimethacrylate, pentaerythritol trimethacrylate, pentaerythritol tetramethacrylate, dipentaerythritol dimethacrylate, dipentaerythritol hexamethacrylate, sorbitol trimethacrylate, sorbitol tetramethacrylate, bis[p-(3-methacryloxy-2-hydroxy propoxy)phenyl]dimethylmethane. Specicific examples of itaconic acid esters as esters of aliphatic polyvalent alcohol compound with unsaturated carboxylic acid include bis[p-(acryloxyethoxy)phenyl]dimethylmethane, itaconic acid esters such as ethylene glycol diitaconate, propylene glycol diitaconate, 1,3-butanediol diitaconate, 1,4-butanediol diitaconate, tetramethylene glycol diitaconate, pentaerythritol diitaconate and sorbitol tetraitaconate.

Examples of crotonic acid esters as esters of aliphatic polyvalent alcohol compound with unsaturated carboxylic acid include ethylene glycol dicrotonate, tetramethylene glycol dicrotonate, pentaerythritol dicrotonate, and sorbitol tetradicrotonate. Examples of isocrotonic acid esters as esters of aliphatic polyvalent alcohol compound with unsaturated carboxylic acid include ethylene glycol diisocrotonate, pentaerythritol diisocrotonate, and sorbitol tetraisocrotonate. Examples of maleic acid esters as esters of aliphatic polyvalent alcohol compound with unsaturated carboxylic acid include ethylene glycol dimalate, triethylene glycol dimalate, pentaerythritol dimalate, and sorbitol tetramalate. Further examples of the esters of aliphatic polyvalent alcohol compound with unsaturated carboxylic acid include mixtures of the aforementioned ester monomers. Specific examples of the amide of aliphatic polyvalent amine compound with unsaturated carboxylic acid as monomer include methylene bis-acrylamide, methylene bis-methacrylamide, 1,6-hexamethylene bis-acrylamide, 1,6-hexamethylene bis-methacrylamide, diethylene glycol triamine trisacrylamide, xylylene bisacrylamide, and xylylene bismethacrylamide.

Other examples of the monomer include vinylurethane compound containing two or more polymerizable vinyl groups per molecule obtained by adding a vinyl monomer containing a hydroxyl group represented by the following general formula (A) to a polyisocyanate compound having two or more isocyanate groups per molecule described in JP-B-48-41708.

CH2=C(R)COOCH2CH(R')OH(C)     5

(wherein R and R' each represent H or CH$_3$)

Further examples of the monomer employable herein include polyfunctional acrylates and methacrylates such as urethane acrylates as disclosed in JP-A-51-37193, polyester acrylates as disclosed in JP-A-48-64183, JP-B-49-43191 and JP-B-52-30490 and epoxy acrylates obtained by reacting epoxy resin with (meth)acrylic acid. Further, those described as photo-curable monomers and oligomers in "Nihon Secchaku Kyokaishi (Bulletin of Japan Adhesive Industry Association)", vol. 20, No. 7, pp. 300–308, 1984 may be used. In the invention, these monomers may be used in a chemical form such as prepolymer, i.e., dimer, trimer, oligomer, mixture and copolymer thereof.

The used amount of all the polymerizable group-containing crosslinking agents, including crosslinking agents represented by the general formulae (I) and (II) and other crosslinking agents, is normally from 1 to 99.99%, preferably from 5 to 90.0%, more preferably from 10 to 70% based on the total weight of the components of the polymerizable composition. (The term "%" as used herein is meant to indicate "% by weight".)

However, the content of the compound of the general formula (I) or (II) of the invention in all the polymerizable group-containing compounds is from 5 to 100% by weight, preferably from 10 to 90% by weight, more preferably from 30 to 70% by weight. When the content of the compound of the general formula (I) or (II) falls below 5%, the effect of the invention cannot be occasionally exerted.

The photopolymerization initiator to be incorporated in the polymerizable composition of the invention will be described hereinafter.

Preferred examples of the photopolymerization initiator include (a) aromatic ketones, (b) aromatic onium salt compounds, (c) organic peroxides, (d) thio compounds, (e) hexaaryl biimidazole compounds, (f) ketoxim ester compounds, (g) borate compounds, (h) azinium compounds, (i) metalocene compounds, (j) active ester compounds, and (k) compounds having carbon-halogen bond.

Preferred examples of (a) aromatic ketones include compounds having benzophenone skeleton or thioxanthone skeleton described in "RADIATION CURING IN POLYMER SCIENCE AND TECHNOLOGY", J. P. FOUASSIER J. F. RABEK, 1993, pp. 77–117. Examples of these compounds include the following compounds:

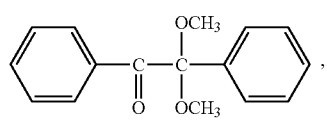

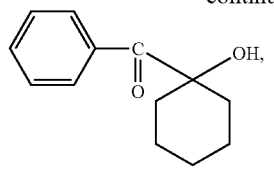

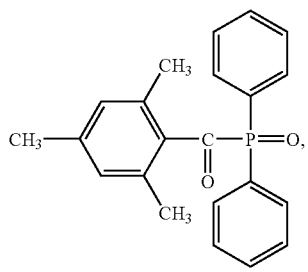

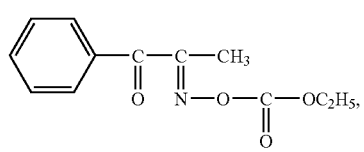

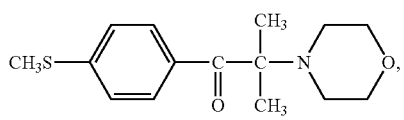

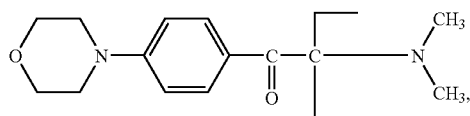

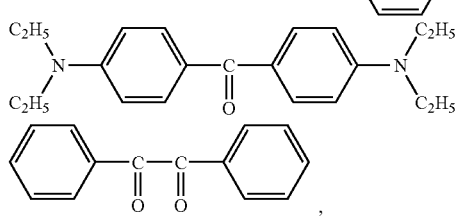

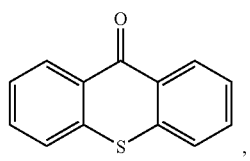

More desirable examples of (a) aromatic ketones include α-thiobenzopheone compounds disclosed in JP-B-47-6416, benzoin ether compounds disclosed in JP-B-47-3981, α-substituted benzoin compounds disclosed in JP-B-47-2232, benzoin derivatives disclosed in JP-B-47-23664, aroylphosphonic acid esters disclosed in JP-B-60-26483, benzoin ethers disclosed in JP-B-60-26403 and JP-A-62-81345, α-aminobenzophenones disclosed in JP-B-1-34242, U.S. Pat. No. 4,318,791 and EP028456A1 such as those represented by the following general formulae:

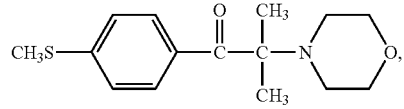

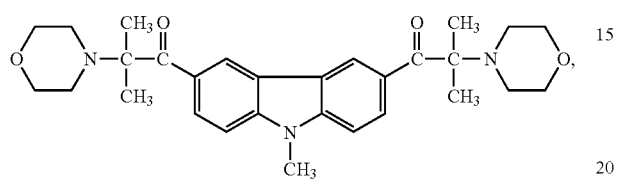

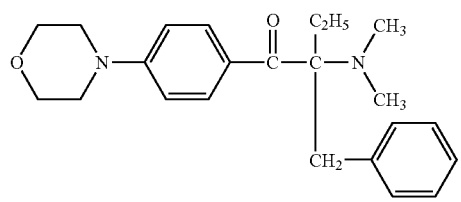

, etc.

p-di(dimethylaminobenzoyl)benzene disclosed in JP-A-2-211452, thio-substituted aromatic ketones disclosed in JP-A-61-194062, acylphosphine sulfide disclosed in JP-B-2-9597, acylphosphine disclosed in JP-B-2-9596 such as those represented by the following general formulae:

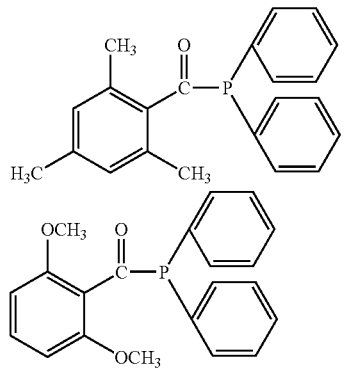

thioxanthones disclosed in JP-B-63-61950, and coumarines disclosed in JP-B-59-42864.

Examples of (b) aromatic onium salts as another photopolymerization initiator include aromatic onium salts of elements belonging to the groups V, VI and VII in the periodic table such as N, P, As, Sb, Bi, O, S, Se, Te and I. Examples of these aromatic onium salts include compounds disclosed in JP-B-52-14277, JP-B-52-14278, and JP-B-52-14279. Specific examples of these compounds include the following compounds:

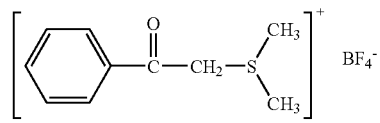

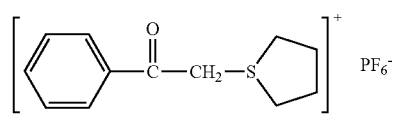

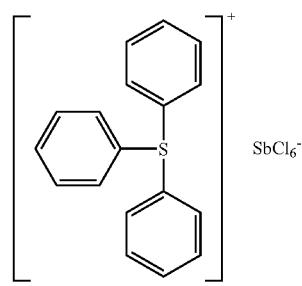

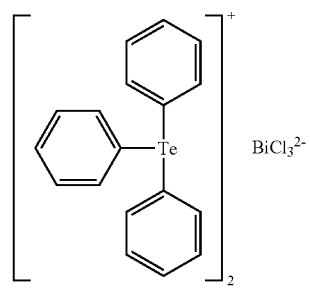

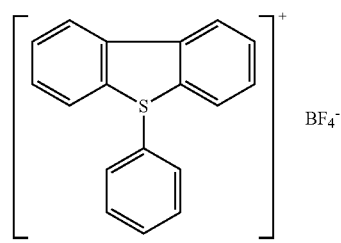

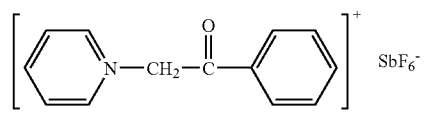

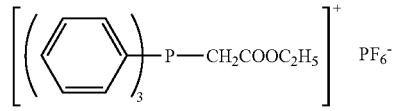

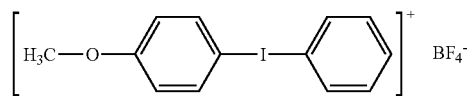

Further examples of (b) aromatic onium salts include the following diazonium salts.

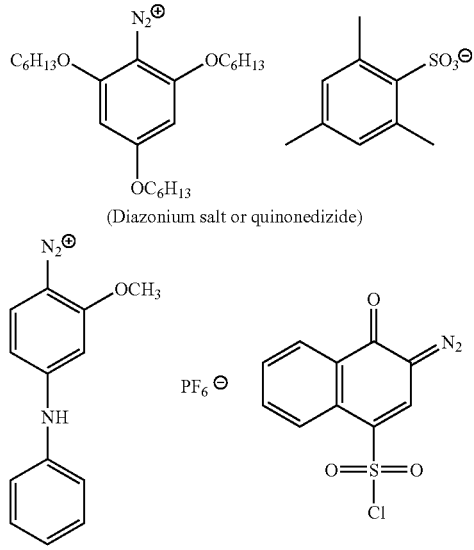

(Diazonium salt or quinonedizide)

The organic peroxides (c) as further examples of the photopolymerization initiator to be used in the invention include almost all of organic compounds having one or more oxygen-oxygen bonds per molecule. Preferred examples of these organic compounds include ester peroxides such as 3,3',4,4'-tetra-(t-butylperoxycarbonyl)benzophenone, 3,3',4,4'-tetra-(t-amylperoxycarbonyl)benzophenone, 3,3',4,4'-tetra-(t-hexylperoxycarbonyl)benzophenone, 3,3',4,4'-tetra-(t-octylperoxycarbonyl)benzophenone, 3,3',4,4'-tetra-(cumylperoxycarbonyl)benzophenone, 3,3',4,4'-tetra-(p-isopropylcumylperoxycarbonyl)benzophenone and di-t-butyldiperoxy isophthalate.

The thio compound (d) as photopolymerization initiator to be used in the invention is represented by the following general formula [II]

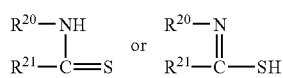

wherein $R^{20}$ represents an alkyl, aryl or substituted aryl group; $R^{21}$ represents a hydrogen atom or alkyl group; and $R^{20}$ and $R^{21}$ represent non-metallic atomic groups required to form a 5- to 7-membered ring which may contain hetero atoms selected from oxygen, sulfur and nitrogen when connected to each other.

The alkyl group in the aforementioned general formula [II] is preferably an alkyl group having from 1 to 4 carbon atoms. The aryl group in the aforementioned general formula [II] is preferably an aryl group having from 6 to 10 carbon atoms such as phenyl and naphthyl. Examples of the substituted aryl group include those obtained by substituting the aforementioned aryl group by a halogen atom such as chlorine, an alkyl group such as methyl or an alkoxy group such as methoxy and ethoxy. $R^{21}$ is preferably an alkyl group having from 1 to 4 carbon atoms.

Examples of (e) hexaaryl biimidazole which is a further example of the photopolymerization initiator to be used in the invention include lophine dimers disclosed in JP-B-45-37377 and JP-B-44-86516 such as 2,2'-bis(o-chlorophenyl)-4,4',5,5'-tetraphenylbiimidazole, 2,2'-bis(o-bromophenyl)-4,4',5,5'-tetraphenylbiimidazole, 2,2'-bis(o,p-dichlophenyl)-4,4',5,5'-tetraphenylbiimidazole, 2,2'-bis(o-chlorophenyl)-4,4',5,5'-tetra(m-methoxyphenyl)biimidazole, 2,2'-bis(o,o'-dichlorophenyl)-4,4',5,5'-tetraphenylbiimidazole, 2,2'-bis(o-nitrophenyl)-4,4',5,5'-tetraphenylbiimidazole, 2,2'-bis(o-methylphenyl)-4,4',5,5'-tetraphenylbiimidazole and 2,2'-bis(o-trifluorophenyl)-4,4',5,5'-tetraphenylbiimidazole.

Examples of (f) ketoxim ester which is a further example of the photopolymerization initiator to be used in the invention include 3-benzoyloxyiminobutane-2-one, 3-acetoxyiminobutane-2-one, 3-propionyloxyiminobutane-2-one, 2-acetoxyiminopentane-3-one, 2-acetoxyimino-1-phenyl-propane-1-one, 2-benzoyloxyimino-1-phenylpropane-1-one, 3-p-toluenesulfonyloxyiminobutane-2-one, and 2-ethoxycarbonyloxyimino-1-phenylpropane-1-one.

Examples of (g) borate which is a further example of the photopolymerization initiator to be used in the invention include compounds represented by the following general formula [III]:

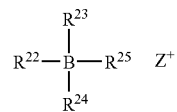

wherein $R^{22}$, $R^{23}$, $R^{24}$ and $R^{25}$ may be the same or different and each represent a substituted or unsubstituted alkyl group, substituted or unsubstituted aryl group, substituted or unsubstituted alkenyl group, substituted or unsubstituted alkynyl group or substituted or unsubstituted heterocyclic group; two or more of $R^{22}$, $R^{23}$, $R^{24}$ and $R^{25}$ may be connected to each other to form a cyclic structure, with the proviso that at least one of $R^{22}$, $R^{23}$, $R^{24}$ and $R^{25}$ is a substituted or unsubstituted alkyl group; $Z^+$ represents an alkaline metal cation or quaternary ammonium cation.

Examples of the alkyl groups represented by $R^{22}$, $R^{23}$, $R^{24}$ and $R^{25}$ include straight-chain, branched and cyclic alkyl groups which each preferably have from 1 to 18 carbon atoms. Specific examples of these alkyl groups include methyl, ethyl, propyl, isopropyl, butyl, pentyl, hexyl, octyl, stearyl, cyclobutyl, cyclopentyl, and cyclohexyl. Examples of the substituted alkyl group include those obtained by substituting the aforementioned alkyl groups by substituents such as halogen atom (e.g., —Cl, —Br), cyano group, nitro group, aryl group (preferably phenyl group), hydroxyl group,

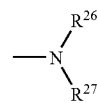

(wherein $R^{26}$ and $R^{27}$ each independently represent a hydrogen atom or a $C_1$–$C_{14}$ alkyl or aryl group), —COOR$^{28}$ (wherein $R^{28}$ represents a hydrogen atom or a $C_1$–$C_{14}$ alkyl or aryl group), —OCOR$^{29}$ and —OR$^{30}$ (wherein $R^{29}$ and $R^{30}$ each represent a $C_1$–$C_{14}$ alkyl or aryl group). Examples of the aryl groups represented by $R^{22}$ to $R^{25}$ include monocyclic to tricyclic aryl groups such as phenyl group and naphthyl group. Examples of the substituted aryl groups represented by $R^{22}$ to $R^{25}$ include those obtained by substituting the aforementioned aryl groups by the substituents on the aforementioned substituted alkyl groups or $C_1$–$C_{14}$ alkyl groups. Examples of the alkenyl groups represented by $R^{22}$ to $R^{25}$ include $C_2$–$C_{18}$ straight-chain, branched or cyclic alkenyl groups. Examples of the substituents on the substituted alkenyl groups include those listed above with reference to the substituted alkyl groups. Examples of the alkynyl groups represented by $R^{22}$ to $R^{25}$ include $C_2$–$C_{28}$ straight-chain or branched alkynyl groups. Examples of the substitutents on the substituted alkynyl groups include those listed above with reference to the substituted alkyl groups. Examples of the heterocyclic groups represented by $R^{22}$ to $R^{25}$ include 5-membered or higher, preferably 5-membered to 7-membered heterocyclic groups containing at least one of N, S and O which may contain condensed rings. Further examples of the substituents on the substituted alkynyl groups include those listed above with reference to the substituted alkyl groups. Specific examples of the compounds represented by the general formula [III] include those disclosed in U.S. Pat. Nos. 3,567,453 and 4,343,891, and EP 109,772 and 109,773, and the following compounds:

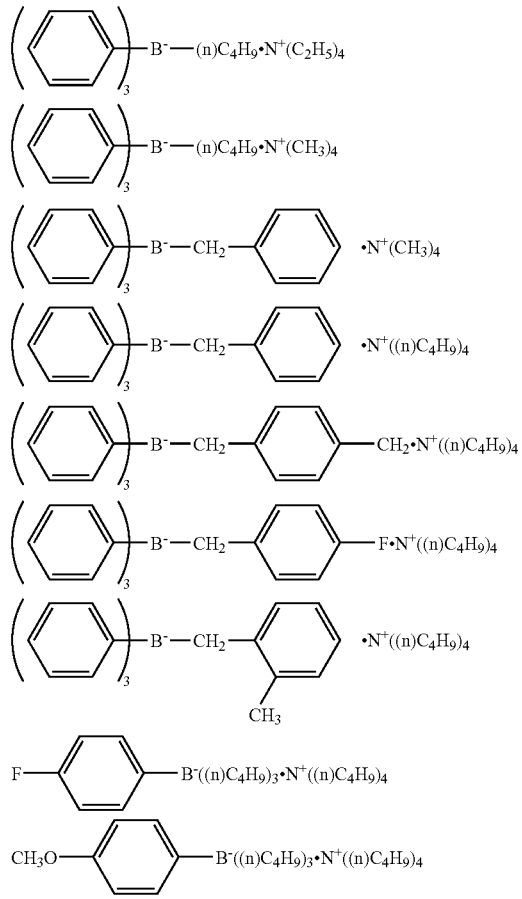

Examples of (h) azinium salt compound which is a further example of the photopolymerization initiator of the invention include compounds having N—O bond disclosed in JP-A-63-138345, JP-A-63-142345, JP-A-142346, JP-A-63-143537, and JP-B-46-42363.

Examples of (i) metalocene compound which is a further example of the photopolymerization initiator include titanocene compounds disclosed in JP-A-59-152396, JP-A-61-151197, JP-A-63-41484, JP-A-2-249 and JP-A-2-4705, and iron-arene complexes disclosed in JP-A-1-304453 and JP-A-1-152109.

Specific examples of the aforementioned titanocene compounds include di-cyclopentadienyl-titanium-di-chloride, di-cyclopentadienyl-titanium-bis-phenyl, di-cyclopentadienyl-titanium-bis-2,3,4,5,6-pentafluro pheny-1-il, di-cyclopentadienyl-titanium-bis-2,3,5,6-tetrafluoropheny-1-il, di-cyclopentadienyl-titanium-bis-2,4,6-trifluoropheny-1-il, di-cyclopentadienyl-titanium-2,6-difluoropheny-1-il, di-cyclopentadienyl-titanium-bis-2,4-difluoropheny-1-il, di-methylcyclopentadienyl-titanium-bis-2,3,4,5,6-pentafluoropheny-1-il, di-cyclopentadienyl-titanium-bis-2,3,5,6-tetrafluoropheny-1-il, di-cyclopentadienyl-titanium-bis-2,4-difluoropheny-1-il, bis(cyclopentadienyl-bis(2,6-difluoro-3-(pyry-1-il)phenyl)titanium, bis(cyclopentadienyl)bis[2,6-difluoro-3-(methylsulfonamide)phenyl]titanium, and bis(cyclopentadienyl)bis[2,6-difluoro-3-(N-butylbialloyl-amino)phenyl]titanium.

Examples of (j) active ester compound which is a further example of the photopolymerization initiator include imidosulfonate compounds disclosed in JP-B-62-6223, and active sulfonates disclosed in JP-B-63-1430 and JP-A-59-174831.

Examples of (k) compound having carbon-halogen bond which is a further example of the photopolymerization initiator include compounds represented by the following general formulae [IV] to [X]:

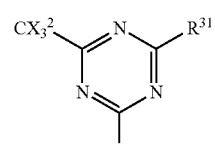

Formula [IV]

wherein $X^2$ represents a halogen atom; $Y^2$ represents —C($X^2$)$_3$, —NH$_2$, —NHR$^{32}$, —NR$^{32}$ or —OR$^{32}$ (in which $R^{32}$ represents an alkyl, substituted, aryl or substituted aryl group); and $R^{31}$ represents —C($X^2$)$_3$, alkyl group, substituted alkyl group, aryl group, substituted aryl group or substituted alkenyl group.

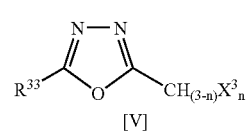

Formula [V]

wherein $R^{33}$ represents an alkyl group, substituted alkyl group, alkenyl group, substituted alkenyl group, aryl group, substituted aryl group, halogen atom, alkoxy group, substituted alkoxyl group, nitro group or cyano group; $X^3$ represents a halogen atom; and n represents an integer of from 1 to 3.

Formula [VI]

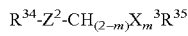

wherein $R^{34}$ represents an aryl group or substituted aryl group; $R^{35}$ represents:

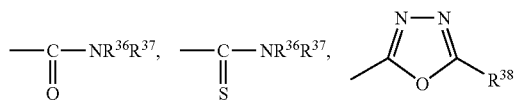

or halogen atom; $Z^2$ represents —C(=O)—, —C(=S) or —SO$_2$—; $R^{36}$ and $R^{37}$ each represent an alkyl group, substituted alkyl group, alkenyl group, substituted alkenyl group, aryl group or substituted aryl group; $R^{38}$ has the same meaning as $R^{32}$ in the general formula [IV]; $X^3$ represents a halogen atom; and m represents an integer of from 1 or 2.

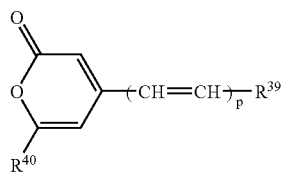

wherein $R^{39}$ represents an aryl group or heterocyclic group which may be substituted; $R^{40}$ represents a trihalokyl group or trihaloalkenyl group having from 1 to 3 carbon atoms; and p represents an integer of from 1 to 3.

Carbonylmethylene heterocyclic compound having trihalogenomethyl group represented by the following general formula [VIII]:

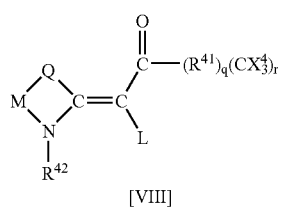

wherein L represents a hydrogen atom or a substituent represented by the general formula: CO—$(R^{41})$q$(C(X^4)_3)$r; Q represents a sulfur, selenium or oxygen atom, dialkylmethylene group, alkene-1,2-ilene group, 1,2-phenylene group or N—R group; M represents a substituted or unsubstituted alkylene or alkenylene group or 1,2-arylene group; $R^{42}$ represents an alkyl, aralkyl or alkoxyalkyl group; $R^{41}$ represents a divalent carbon ring or heterocyclic aromatic group; X4 represents a chlorine, bromine or iodine atom; and q represents 0 and r represents 1 or q represents 1 and r represents 1 or 2. 4-Halogeno-5-(halogenomethyl-phenyl)-oxazole derivative represented by the following general formula [IX]:

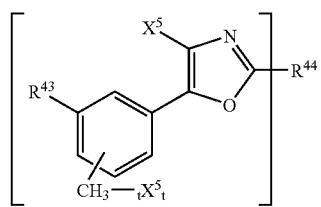

wherein $X^5$ represents a halogen atom; t represents an integer of from 1 to 3; s represents an integer of from 1 to 4; $R^{43}$ represents a hydrogen atom or CH$_{3-t}$X$^5_t$ group; and $R^{44}$ represents an unsaturated organic group having a valence of s which may be substituted.

2-(Halogenomethyl-phenyl)-4-halogeno-oxazole derivative represented by the following general formula [X]:

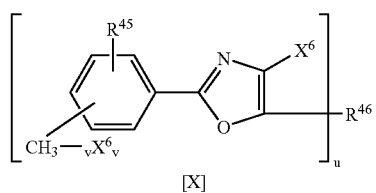

wherein $X^6$ represents a halogen atom; v represents an integer of from 1 to 3; u represents an integer of from 1 to 4; $R^{45}$ represents a hydrogen atom or CH$_{3-v}$X$^6_v$; and $R^{46}$ represents an unsaturated organic group having a valence of u which may be substituted.

Specific examples of such a compound having carbon-halogen bond include compounds disclosed in Wakabayashi et al., "Bull. Chem. Soc. Japan", 42, 2924, 1969, such as 2-phenyl-4,6-bis(trichloromethyl)-S-triazine, 2-(p-chlorophenyl)-4,6-bis(trichloromethyl)-S-triazine, 2-(p-tolyl)-4,6-bis(trichloromethyl)-S-triazine, 2-(p-methoxyphenyl)-4,6-bis(trichloromethyl)-S-triazine, 2-(2',4'-dichlorophenyl)-4,6-bis(trichloromethyl)-S-triazine, 2,4,6-tris(trichloromethyl)-S-triazine, 2-methyl-4,6-bis(trichloromethyl)-S-triazine, 2-n-nonyl-4,6-bis(trichloromethyl)-S-triazine, and 2-(α,α,β-trichloroethyl)-4,6-bis(trichloromethyl)-S-triazine. Other examples of such a compound having carbon-halogen bond include compounds disclosed in British Patent 1,388,492 such as 2-styryl-4,6-bis(trichloromethyl)-S-triazine, 2-(p-methylstyryl)-4,6-bis(trichloromethyl)-S-triazine, 2-(p-methoxystyryl)-4,6-bis(trichloromethyl)-S-triazine and 2-(p-methoxystyryl)-4-amino-6-trichloromethyl-S-triazine, compounds disclosed in JP-A-53-133428 such as 2-(4-methoxy-naphtho-1-il)-4,6-bis-trichloromethyl-S-triazine, 2-(4-ethoxy-naphtho-1-il)-4,6-bis-trichloromethyl-S-triazine, 2-[4-ethoxyethyl]-naphtho-1-il]-4,6-bis-trichloromethyl-S-triazine, 2-(4,7-dimethoxy-naphtho-1-il)-4,6-bis-trichloromethyl-S- triazine) and 2-(acetonaphtho-5-il)-4,6-bis-trichloromethyl-S-triazine, and compounds disclosed in German Patent 3,337,024.

Further examples of such a compound having carbon-halogen bond include compounds disclosed in F. C. Schaefer et al., "J. Org. Chem.", 29, 1527, 1964 such as 2-methyl-4, 6-bis(tribromomethyl)-S-triazine, 2,4,6-tris(tribromomethyl)-S-triazine, 2,4,6-tris(dibromomethyl)-S-triazine, 2-amino-4-methyl-6-tribromomethyl-S-triazine and 2-methoxy-4-methyl-6-trichloromethyl-S-triazine. Further examples of such a compound having carbon-halogen bond include compounds disclosed in JP-A-62-58241. Further examples of such a compound having carbon-halogen bond include compounds disclosed in JP-A-5-281728 such as compounds represented by the following general formulae:

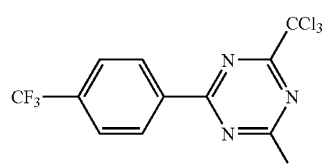

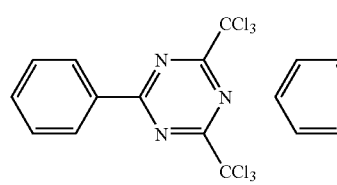

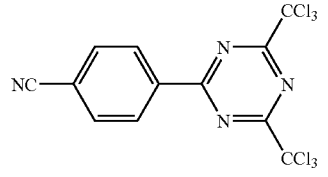

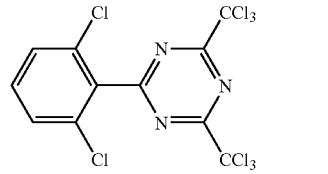

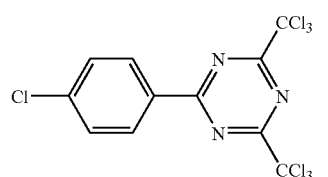

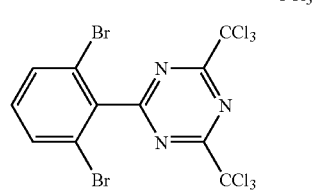

Further examples of such a compound having carbon-halogen bond include the following compounds which can be easily synthesized by those skilled in the art according to the method disclosed in M. P. Hutt, E. F. Elslager and L. M. Herber, "Journal of Heterocyclic Chemistry", vol. 7 (No. 3), pp. 511 and after, 1970:

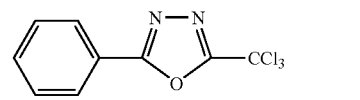

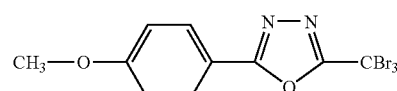

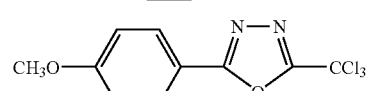

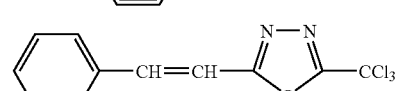

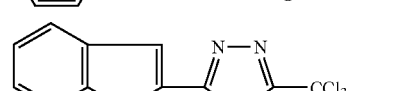

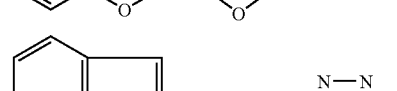

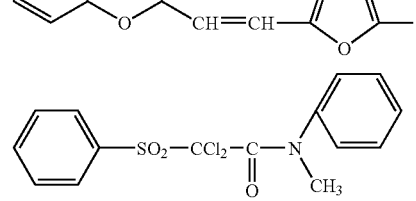

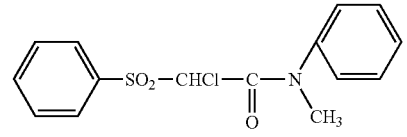

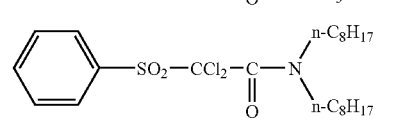

Further examples of such a compound having carbon-halogen bond include compounds disclosed in German Patent 2,641,100 such as 4-(4-methoxy-styryl)-6-(3,3,3-trichloropropenyl)-2-pyrone and 4-(3,4,5-trimethoxy-styryl-6-trichloromethyl-2-pyrone, compounds disclosed in German Patent 3,333,450, compounds disclosed in German Patent 3,021,590, and compounds disclosed in German Patent 3,021,599.

Even more desirable examples of the photopolymerization initiator of the invention include the aforementioned aromatic ketones (a), aromatic onium salts (b), organic peroxides (c), hexaaryl biimidazoles (e), metalocene compounds (i) and compounds having carbon-halogen bond. Preferred among these compounds are aromatic iodonium salts, aromatic diazonium salts, titanocene compounds, and trihalomethyl-S-triazine compounds represented by the general formula [IV].

The photopolymerization initiators of the invention are preferably used singly or in combination of two or more thereof.

As a sensitizing dye which can be a component of the polymerizable composition of the invention there may be used a spectral sensitizing dyestuff or a dye or pigment which absorbs light from a light source to interact with a photopolymerization initiator.

Preferred examples of the spectral sensitizing dyestuff or dye include polynucleus aromatic groups (e.g., pyrene, perylene, triphenylene), xanthenes (e.g., fluorescein, eosine, ertythrirosine, rhodamine B, rose bengal), cyanines (e.g., thiacarbocyanine, oxacarbocyanine), melocyaines (e.g., melocyanine, carbomelocyanine), thiazines (e.g., thione, methylene blue, toluidine blue), acridines (e.g., acridine orange, chloroflavin, acryflavin), phthalocyanines (e.g., phthalocyanine, metal phthalocyanine), porphyrins (e.g., tetraphenylporpyrin, centrally metal-substituted porphyrin), chlorophylls (e.g., chlorophyll, chlorophyllin, centrally metal-substituted chlorophyll), metal complexes such as one represented by the following general formula:

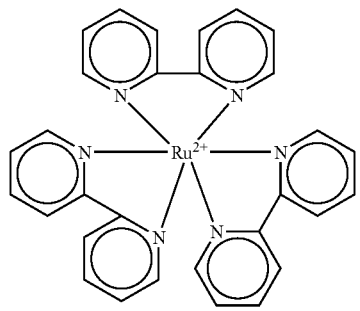

anthraquinones (e.g., anthraquinone), and squariliums (e.g., squarilium).

Preferred examples of the spectral sensitizing dyestuff or dye include styryl-based dyestuffs disclosed in JP-B-37-13034, cation dyes disclosed in JP-A-62-143044, quinoxalinium salts disclosed in JP-B-59-24147, novel methylene blue compounds disclosed in JP-A-64-33104, anthraquinones disclosed in JP-A-64-56767, benzoxanthenes disclosed in JP-A-2-1714, acridines disclosed in JP-A-2-226148 and JP-A-2-226149, pyrilium salts disclosed in JP-B-40-28499, cyanines disclosed in JP-B-46-42363, benzofurane dyestuffs disclosed in JP-A-2-63053, conjugated ketone dyestuffs disclosed in JP-A-2-85858 and JP-A-2-216154, dyestuffs disclosed in JP-A-57-10605, azocinnamylidene derivatives disclosed in JP-B-2-30321, cyanine-based dyes disclosed in JP-A-1-287105, xanthene-based dyes disclosed in JP-A-62-31844, JP-A-62-31848 and JP-A-62-143043, aminostyrylketones disclosed in JP-A-59-28325, melocyanine dyestuffs disclosed in JP-B-61-9621, dyestuffs disclosed in JP-A-2-179643, and melocyanine dyestuffs represented by the following general formula [1] disclosed in JP-A-2-244050:

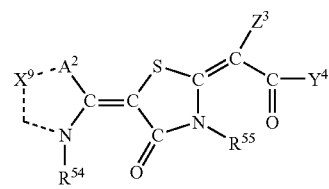

[1]

wherein $R^{54}$ and $R^{55}$ each independently represent a hydrogen atom, alkyl group, substituted alkyl group, alkoxycarbonyl group, aryl group, substituted aryl group or aralkyl group; A2 represents an oxygen atom, sulfur atom, selenium atom, tellurium atom, alkyl- or aryl-substituted nitrogen atom or dialkyl-substituted carbon atom; $X^9$ represents a non-metallic atomic group required to form a nitrogen-containing heterocyclic 5-membered ring; $Y^4$ represents a substituted phenyl group, substituted or unsubstituted polynucleus aromatic group or substituted or unsubstituted heterocyclic aromatic group; and $Z^3$ represents a hydrogen atom, alkyl group, substituted alkyl group, aryl group, substituted aryl group, aralkyl group, alkoxy group, alkylthio group, arylthio group, substituted amino group, acyl group or alkoxycarbonyl group and may be connected to $Y^4$ to form a ring. Specific preferred examples of the melocyanine dyestuffs include those represented by the following general formulae:

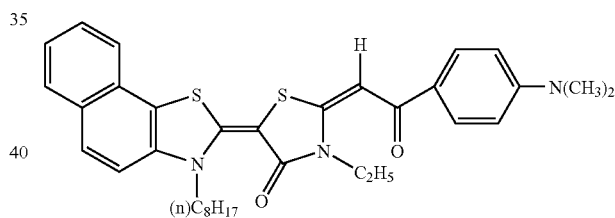

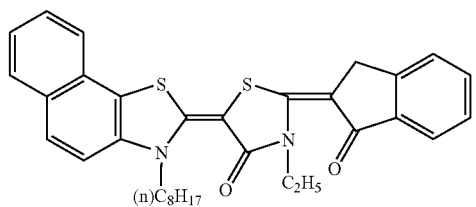

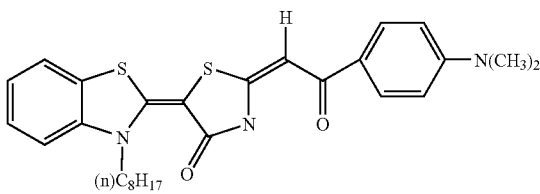

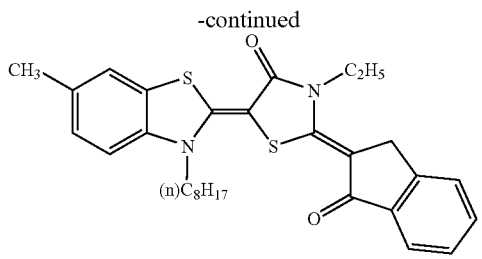

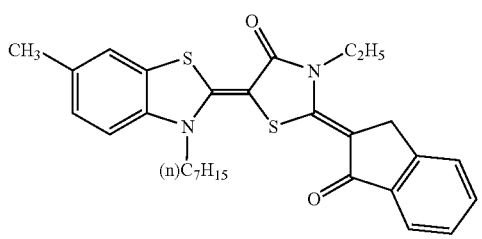

melocyanine dyestuffs represented by the following general formula [2] disclosed in JP-B-59-28326:

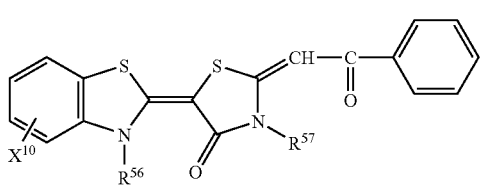

wherein $R^{56}$ and $R^{57}$ each represent a hydrogen atom, alkyl group, substituted alkyl group, aryl group, substituted aryl group or aralkyl group and may be the same or different; and $X^{10}$ represents a substituent having a Hammett's σ value of from −0.9 to +0.5. Further examples of these melocyanine dyestuffs include melocyanine dyestuffs represented by the following general formula [3] disclosed in JP-A-59-89303:

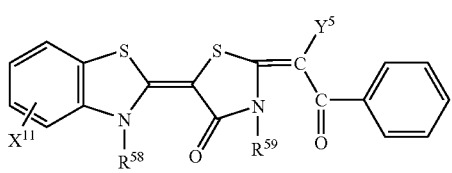

wherein $R^{58}$ and $R^{59}$ each independently represent a hydrogen atom, alkyl group, substituted alkyl group, aryl group, substituted aryl group or aralkyl group; $X^{11}$ represents a substituent having a Hammett's σ value of from −0.9 to +0.5; and Y5 represents a hydrogen atom, alkyl group, substituted alkyl group, aryl group, substituted aryl group, aralkyl group, acyl group or alkoxycarbonyl group. Specific preferred examples of these melocyanine dyestuffs include melocyanine dyestuffs represented by the following general formula [4] disclosed in JP-A-8-129257:

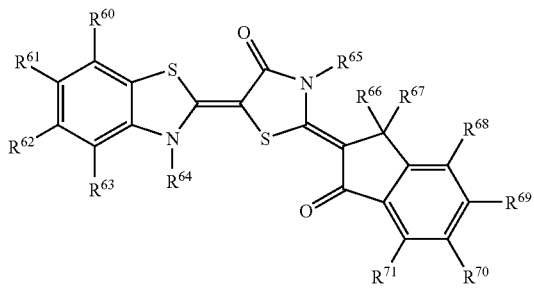

wherein $R^{60}$, $R^{61}$, $R^{62}$, $R^{63}$, $R^{68}$, $R^{69}$, $R^{70}$ and $R^{71}$ each independently represent a hydrogen atom, halogen atom, alkyl group, substituted alkyl group, aryl group, substituted aryl group, hydroxyl group, substituted oxy group, mercapto group, substituted thio group, amino group, substituted amino group, substituted carbonyl group, sulfo group, sulfonato group, substituted sulfinyl group, substituted sulfonyl group, phosphono group, substituted phosphono group, phosphonato group, substituted phosphonato group, cyano group or nitro group or $R^{60}$ and $R^{61}$, $R^{61}$ and $R^{62}$, $R^{62}$ and $R^{63}$, $R^{68}$ and $R^{69}$, $R^{69}$ and $R^{70}$ and $R^{70}$ and $R^{71}$ may be connected to each other to form an aliphatic or aromatic ring; $R^{64}$ represents a hydrogen atom, alkyl group, substituted alkyl group, aryl group or substituted aryl group; $R^{65}$ represents a substituted or unsubstituted alkenylalkyl group or substituted or unsubstituted alkynylalkyl group; and $R^{66}$ and $R^{67}$ each independently represent a hydrogen atom, halogen atom, alkyl group, substituted alkyl group, aryl group, substituted aryl group or substituted carbonyl group. Specific examples of these melocyanine dyestuffs include those represented by the following general formulae:

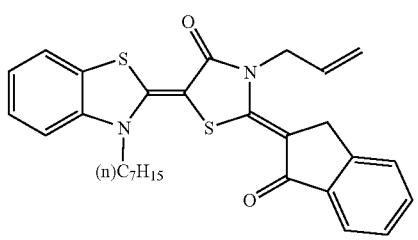

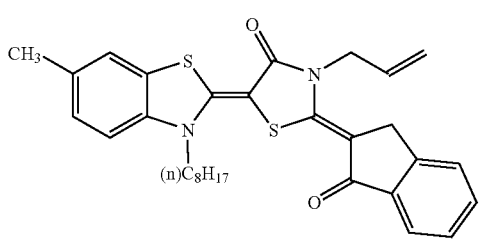

and benzopyrane-based dyestuffs represented by the following general formula [5] disclosed in JP-A-8-334897:

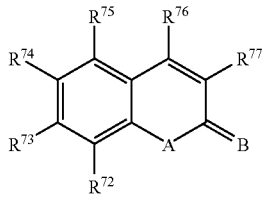

wherein $R^{72}$ to $R^{75}$ each independently represent a hydrogen atom, halogen atom, alkyl group, aryl group, hydroxyl group, alkoxy group or amino group and may form a ring comprising non-metallic atoms with carbon atoms which can be connected thereto; $R^{76}$ represents a hydrogen atom, alkyl group, aryl group, heterocyclic aromatic group, cyano group, alkoxy group, carboxyl group or alkenyl group; $R^{77}$ represents a group represented by $R^{76}$ or -Z-$R^{76}$ (in which Z represents a carbonyl group, sulfonyl group, sulfinyl group or arylene dicarbonyl group); $R^{76}$ and $R^{77}$ may together form a ring comprising non-metallic atoms; A represents an oxygen atom, sulfur atom, NH or nitrogen atom having substituents; and B represents an oxygen atom or =C(G1)(G2) (in which G1 and G2 may be the same or different and each represent a hydrogen atom, cyano group, alkoxycarbonyl group, aryloxycarbonyl group, acyl group, arylcarbonyl group, alkylthio group, arylthio group, alkylsulfonyl group, arylsulfonyl group or fluorosulfonyl group, with the proviso that G1 and G2 are not a hydrogen atom at the same time; and G1 and G2 each represent a short wave type ketone-based or styryl-based dyestuff disclosed in EP1048982A1 which may form a ring comprising non-metallic atoms with carbon atoms such as those represented by the following structural formulae:

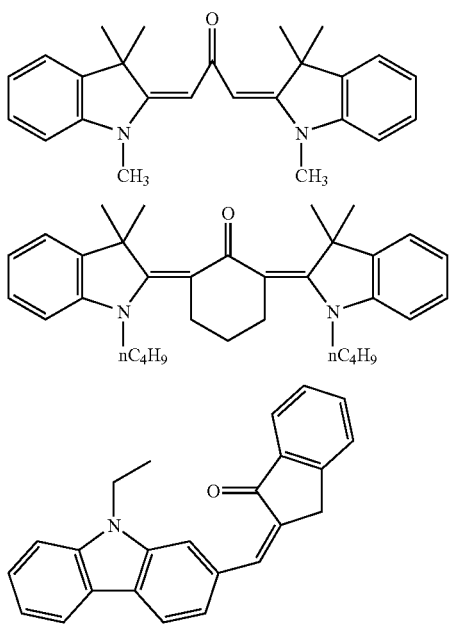

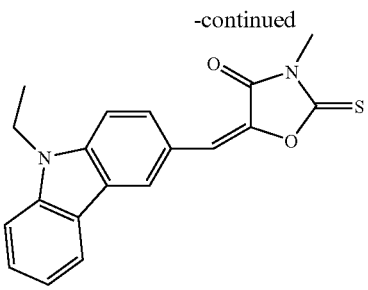

-continued

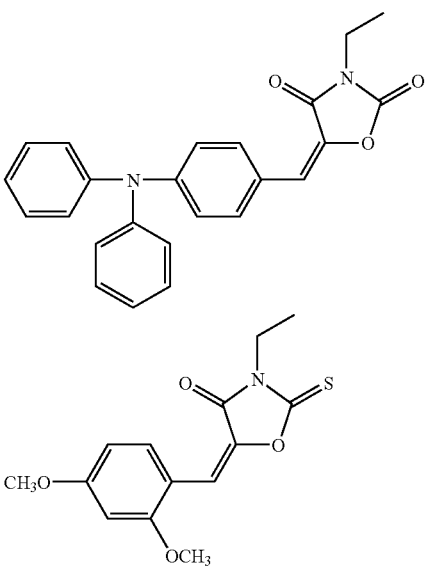

Further examples of the sensitizing dyes which can be preferably used include the following infrared absorbers (dyes or pigments).

Preferred examples of the aforementioned dyes include cyanine dyes disclosed in JP-A-58-125246, JP-A-59-84356, JP-A-59-202829 and JP-A-60-78787, and cyanine dyes disclosed in British Patent 434,875.

Alternatively, near infrared-absorbing sensitizers disclosed in U.S. Pat. No. 5,156,938 can be preferably used. Further, substituted arylbenzo(thio)pyrilium salts disclosed in U.S. Pat. No. 3,881,924, trimethine thiapyrilium salts disclosed in JP-A-57-142645 (U.S. Pat. No. 4,327,169), pyrilium-based compounds disclosed in JP-A-58-181051, JP-A-58-220143, JP-A-59-41363, JP-A-59-84248, JP-A-59-84249, JP-A-59-146063 and JP-A-59-146061, cyanine dyestuffs disclosed in JP-A-59-216146, pentamethine thiopyrilium salts disclosed in U.S. Pat. No. 4,283,475, and pyrilium compounds disclosed JP-B-5-13514 and JP-B-5-19702 can be preferably used.

Further preferred examples of the aforementioned dyes include near infrared-absorbing dyes represented by the general formulae (I) and (II) disclosed in U.S. Pat. No. 4,756,993, and phthalocyanine dyes disclosed in EP9165143A2.

Moreover, anionic infrared absorbers disclosed in Japanese Patent Application No. 10-79912 can be preferably used. An anionic infrared absorber substantially means an infrared-absorbing dyestuff the nucleus of which is free of cationic structure but has an anionic structure. Examples of such a anionic infrared absorber include (c1) anionic metal complexes, (c2) anionic carbon blacks, (c3) anionic phthalocyanines, and (c4) compounds represented by the following general formula (6). The counter cation of these anionic infrared absorbers are monovalent cations, including proton, or polyvalent cations.

$$[G_a\text{-}M\text{-}G_b]_m X^{m+} \quad \text{Formula 6}$$

The anionic metal complex (c1) substantially means a light-absorbing complex which forms an anion by its central metal or entirely by ligands.

Examples of (c2) anionic carbon blacks include carbon blacks having anionic groups such as sulfonic acid, carboxylic acid and phosphonic acid groups connected thereto as substituents. The incorporation of these groups in carbon blacks can be accomplished by oxidizing carbon blacks with a predetermined acid as disclosed in "Handbook of Carbon Black: 3rd Edition", Carbon Black Association Japan, Apr. 5, 1995, page 12.

The anionic phthalocyanine (c3) means a phthalocyanine skeleton which has an anionic group listed above with reference to (c2) anionic carbon blacks connected thereto as a substituent to form an anion as a whole.

The compounds represented by the general formula (6) (c4) will be further described hereinafter. In the general formula (6), $G_a^-$ represents an anionic substituent, and $G_b$ represents a neutral substituent. $X^{m+}$ represents a cation having a valence of from 1 to m, including proton. The suffix m represents an integer of from 1 to 6. M represents a conjugated chain which may have substituents or cyclic structures. The conjugated chain M can be represented by the following general formula:

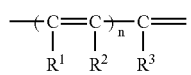

wherein $R^1$, $R^2$ and $R^3$ each independently represent a hydrogen atom, halogen atom, cyano group, alkyl group, aryl group, alkenyl group, alkynyl group, carbonyl group, thio group, sulfonyl group, sulfinyl group, oxy group or amino group and may be connected to each other to form a cyclic structure; and n represents an integer of from 1 to 8.

Among the anionic infrared absorbers represented by the general formula (6), those represented by the following general formulae A-1 to A-5 are preferably used.

A-1

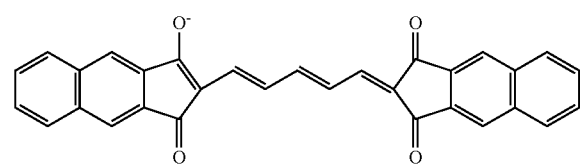

-continued $(^{(n)}C_4H_9)_4N^+$

A-2

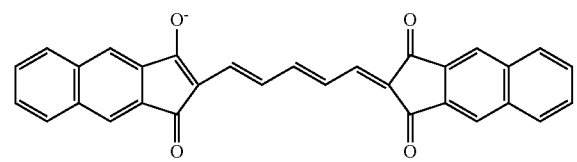

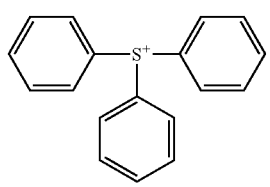

A-3

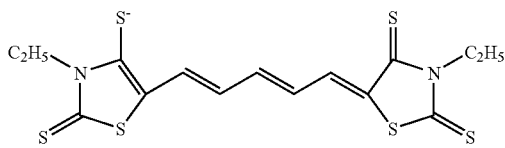

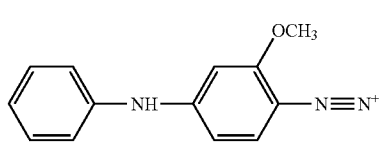

A-4 carbon-black—$CO_2^-$

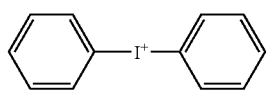

A-5

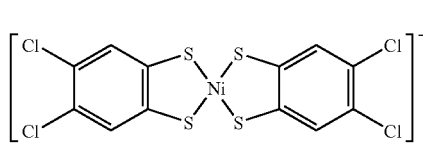

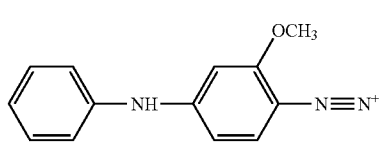

Further, cationic infrared absorbers represented by the following general formulae are preferably used.

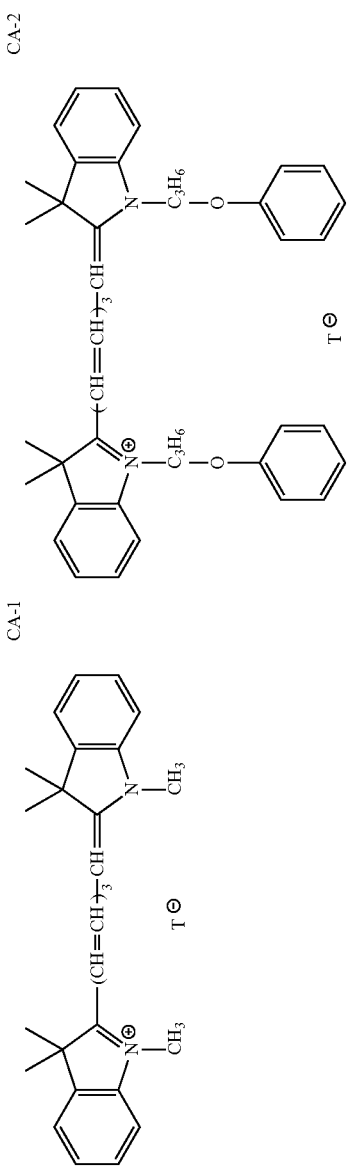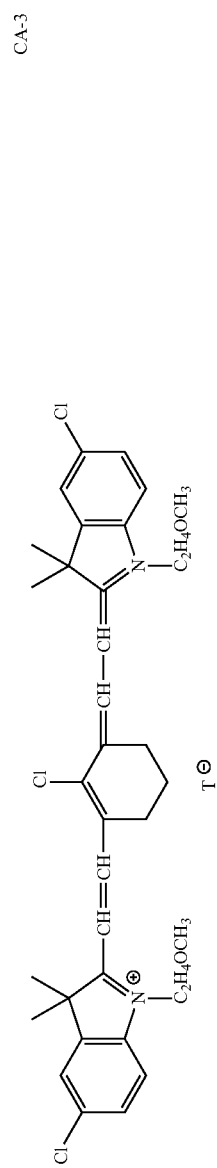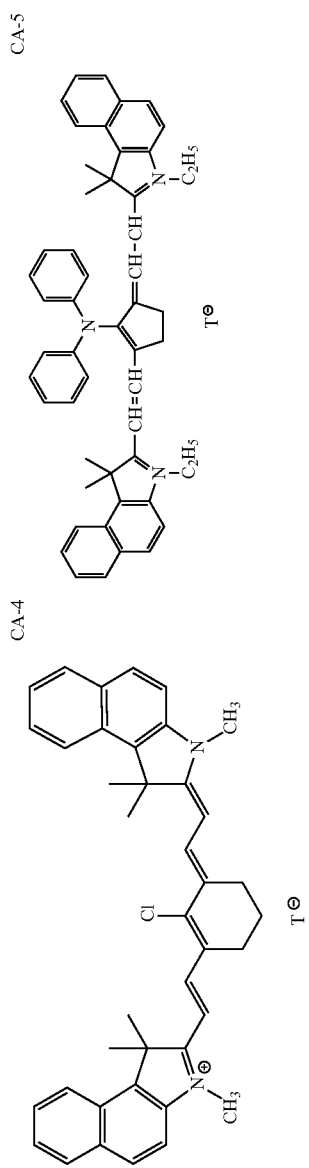

-continued
CA-6
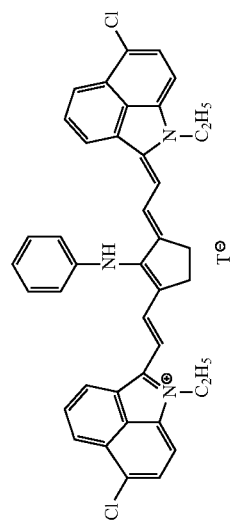
CA-7
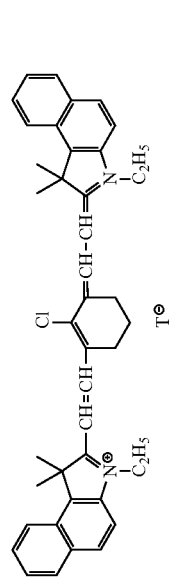
CA-8
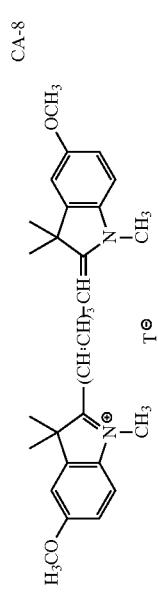
CA-9
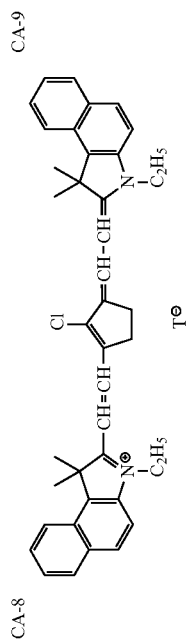
CA-10
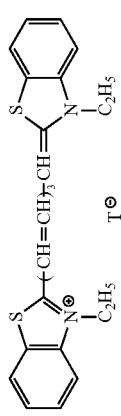
CA-11
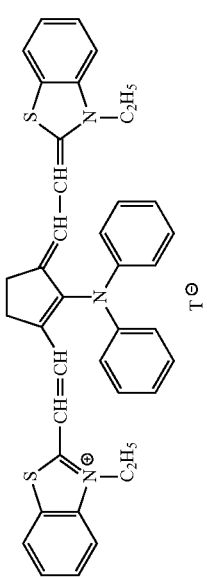
CA-12
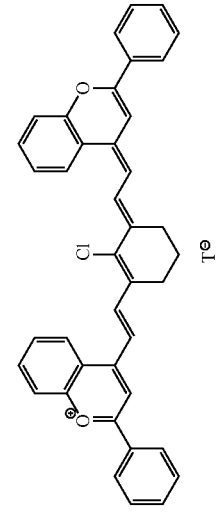
CA-13
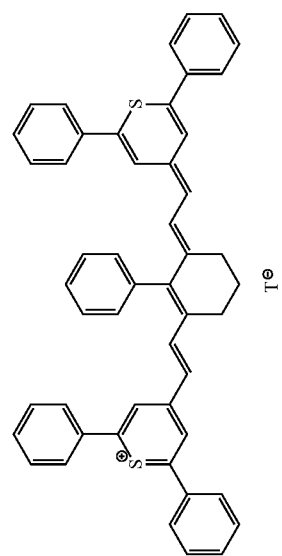

-continued
CA-14
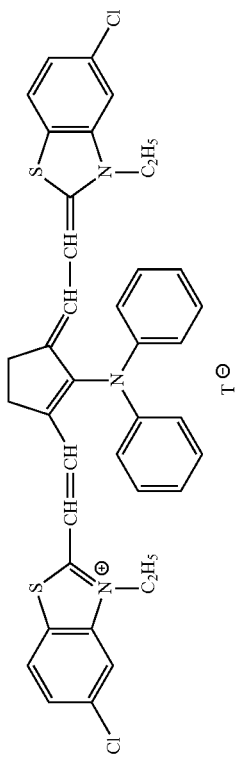
CA-15
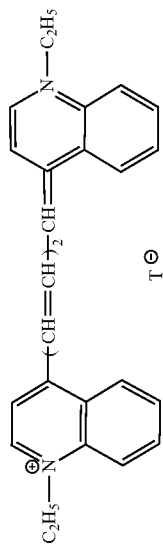
CA-16
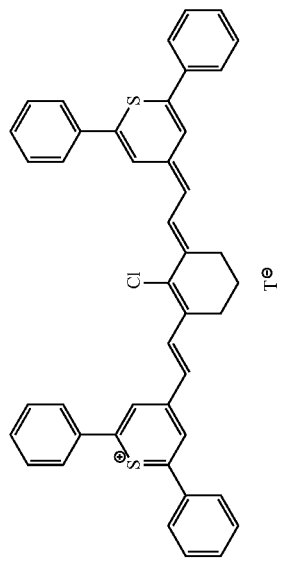
CA-17
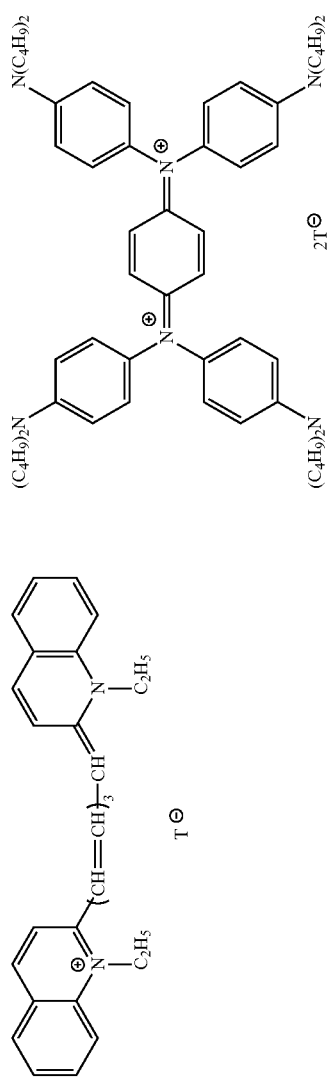
CA-18

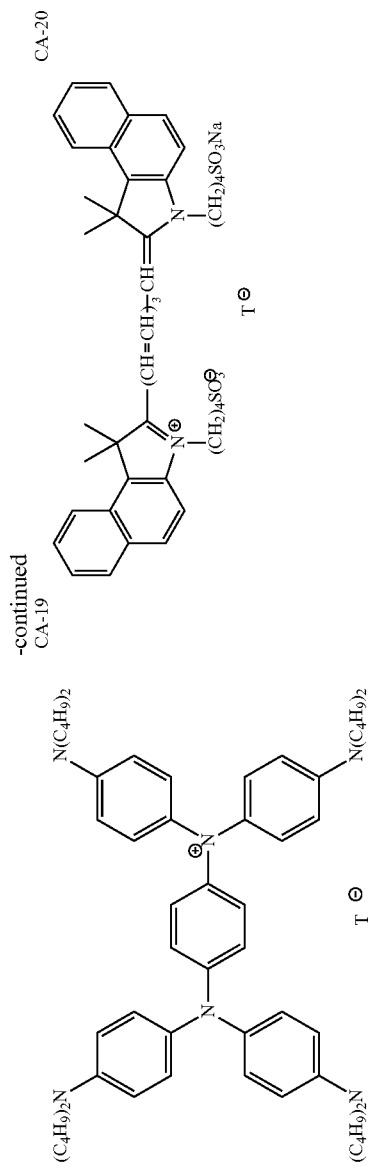
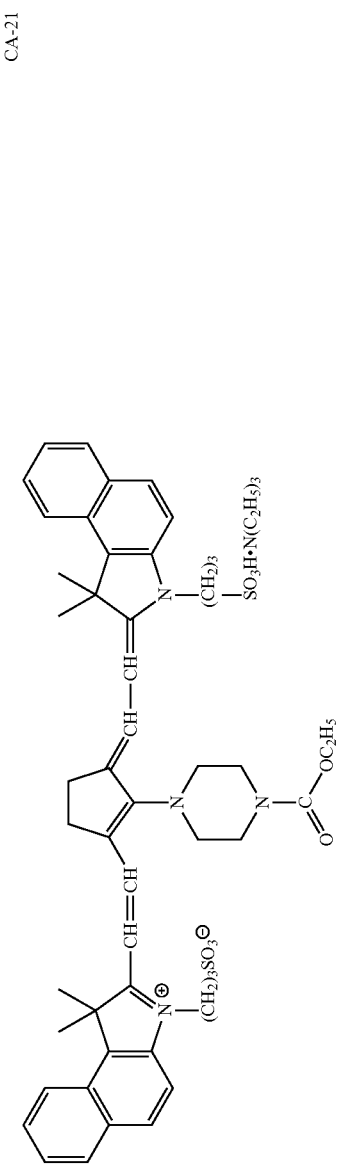
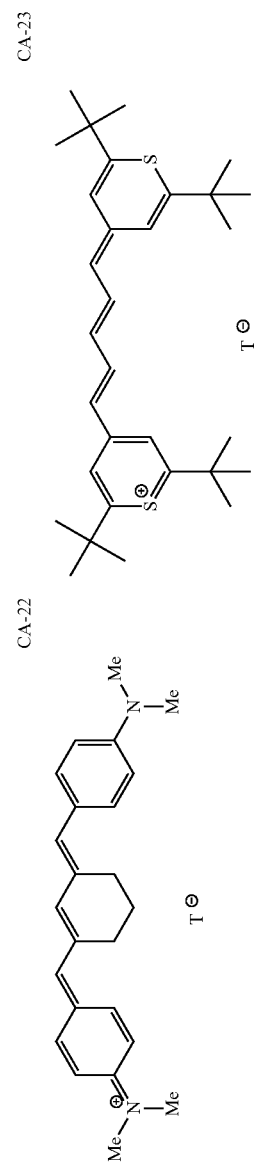

-continued
CA-24
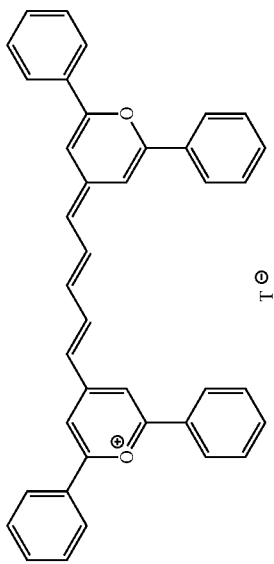
CA-25
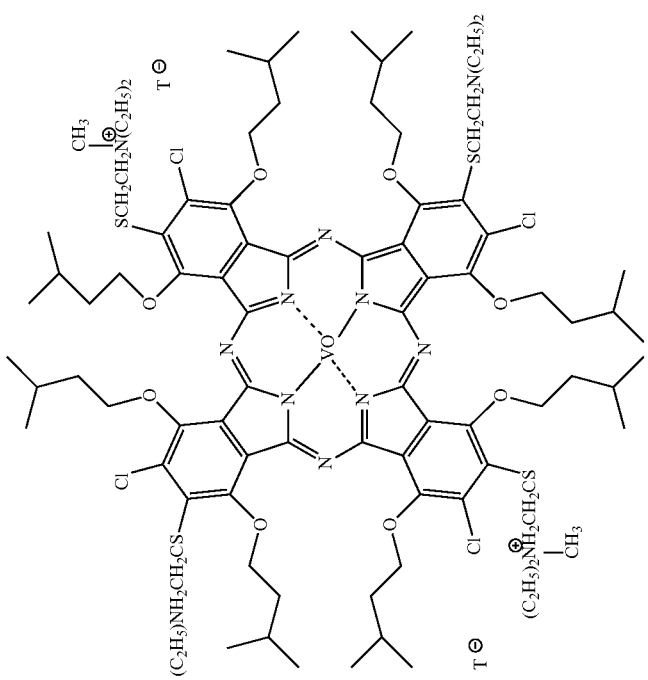

wherein $T^-$ represents a monovalent anion, preferably halogen anion ($F^-$, $Cl^-$, $Br^-$, $I^-$), Lewis acid anion ($BF_4^-$, $PF_6^-$, $SbCl_6^-$, $ClO_4^-$), alkylsulfonic acid anion or arylsulfonic acid anion.

The aforementioned alkylsulfonic acid means a straight-chain, branched or cyclic alkyl group having from 1 to 20 carbon atoms. Specific examples of such a straight-chain, branched or cyclic alkyl group include methyl group, ethyl group, propyl group, butyl group, pentyl group, hexyl group, heptyl group, octyl group, nonyl group, decyl group, undecyl group, dodecyl group, tridecyl group, hexadecyl group, octadecyl group, eicosil group, isopropyl group, isobutyl group, s-butyl group, t-butyl group, isopentyl group, neopentyl group, 1-methylbutyl group, isohexyl group, 2-ethylhexyl group, 2-methylhexyl group, cyclohexyl group, cyclopentyl group, and 2-norbornene group. Preferred among these compounds are straight-chain alkyl groups each having from 1 to 12 carbon atoms, branched alkyl groups each having from 3 to 12 carbon atoms and cyclic alkyl groups each having from 5 to 10 carbon atoms.

The aryl moiety in the aforementioned arylsulfonic acid represents one formed by one benzene ring, a condensed ring formed by two or three benzene rings or a condensed ring formed by a benzene ring and a 5-membered unsaturated ring. Specific examples of these aryl groups include phenyl group, naphthyl group, anthryl group, phenanthryl group, indenyl group, acenabutenyl group, and fluorenyl group. Preferred among these aryl groups are phenyl group and naphthyl group.

Further, non-ionic infrared absorbers represented by the following general formulae can be preferably used.

NA-1
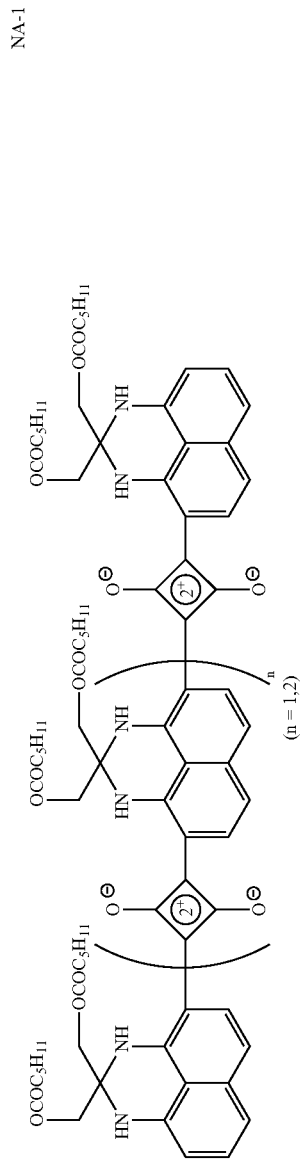
NA-3
NA-2
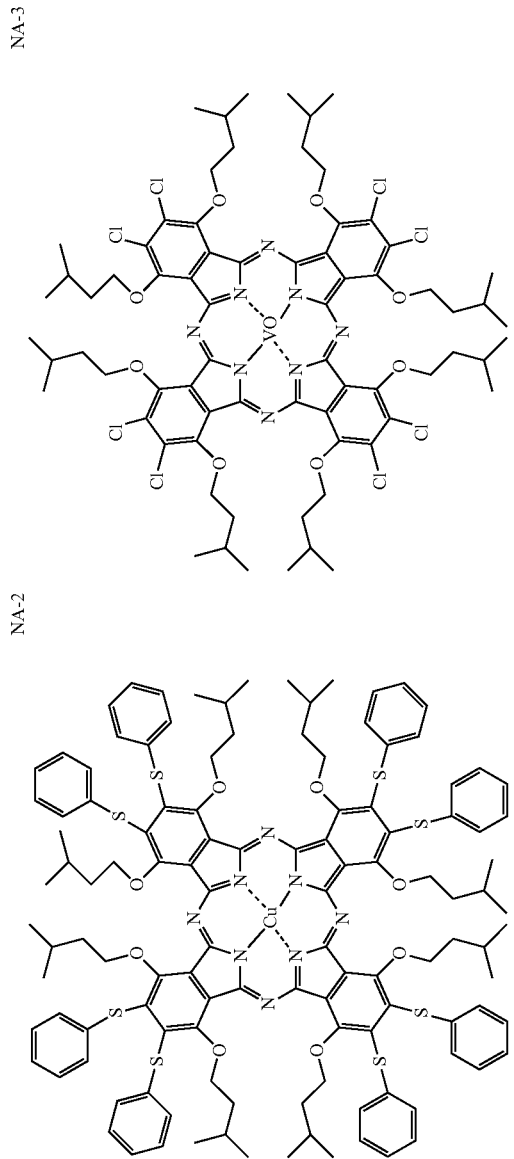

Particularly preferred among these exemplified anionic infrared absorbers is A-1. Particularly preferred among these exemplified cationic infrared absorbers are CA-7,CA-18, CA-22 and CA-23. Particularly preferred among these exemplified nonionic infrared absorbers is NA-2.

As other dyes there may be used commercially available dyes and known dyes described in references such as "Senryo Binran (Handbook of Dyes)", The Society of Synthetic Organic Chemistry, Japan, 1970. Specific examples of these dyes include azo dyes, metal complex-based azo dyes, pyrazolone azo dyes, naphthoquinone dyes, anthraquinone dyes, phthalocyanine dyes, carbonium dyes, quinoneimine dyes, methine dyes, diimmonium dyes, aminium dyes, squarilium dyestuffs, and metal thiolate complexes.

Other examples of pigments which can be used as sensitizing dyestuffs include commercially available pigments and pigments described in "Handbook of Color Index (C. I.)", "Saishin Ganryo Binran (Handbook of Modern Pigments)", Japan Association of Pigment Technology, 1977, "Saishin Ganryo Oyo Gijutsu (Modern Pigment Application Technology)", CMC, 1986, and "Insatsu Inki Gijutsu (Printing Ink Technology)", CMC, 1984. Examples of the pigments employable herein include black pigments, yellow pigments, orange pigments, brown pigments, red pigments, violet pigments, blue pigments, green pigments, fluorescent pigments, metal powder pigments, and polymer-bonded dyes. Specific examples of these pigments include insoluble azo pigments, azo lake pigments, condensed azo pigments, chelate azo pigments, phthalocyanine-based pigments, anthraquinone-based pigments, perylene-based pigments, perynone-based pigments, thioindigo-based pigments, quinacridone-based pigments, dioxazine-based pigments, isoindolinone-based pigments, quinophthalone-based pigments, dyed lake pigments, azine pigments, nitoso pigments, nitro pigments, natural pigments, fluorescent pigments, iorganic pigments, and carbon black. Preferred among these pigments is carbon black.

These pigments may or may not be subjected to surface treatment before use.

As the surface treatment method there may be proposed a method which comprises coating the surface of pigment with a resin or wax, a method which comprises attaching a surface active agent to pigment, a method which comprises bonding a reactive material (e.g., silane coupling agent, epoxy compound, polyisocyanate) to the surface of pigment or the like. For the details of these surface treatment methods, reference can be made to "Kinzoku Sekken no Seishitsu to Oyo (Properties and Application of Metal Soap)", Saiwai Shobo, "Insatsu Inki Gijtsu (Printing Ink Technology)", CMC, 1984, and "Saishin Ganryo Oyo Gijutsu (Modern Pigment Application Technology)", CMC, 1986.

The particle diameter of the pigment is preferably from 0.01 µm to 10 µm, more preferably from 0.05 µm to 1 µm, particularly from 0.1 µm to 1 µm. When the particle diameter of the pigment is not smaller than 0.01 µm, it is advantageous in that the resulting dispersion exhibits a good stability in the image-recording layer coating solution. When the particle diameter of the pigment is not greater than 10 µm, it is advantageous in the uniformity of the image-recording layer.

As a method for the dispersion of the pigment there may be used any known dispersion technique for use in the production of ink, toner, etc. Examples of dispersing machines employable herein include ultrasonic disperser, sand mill, attritor, pearl mill, supermill, ball mill, impellor, disperser, KD mill, colloid mill, dyantron, three-roll mill, and pressure kneader. For the details of these dispersing machines, reference can be made to "Saishin Ganryo Oyo Gijutsu (Modern Pigment Application Technology)", CMC, 1986.

Even more desirable examples of the sensitizing dye employable herein include melocyanine dyestuffs disclosed in the above cited JP-B-61-9621, melocyanine dyestuffs disclosed in JP-A-2-179643, melocyanine dyestuffs disclosed in JP-A-2-244050, melocyanine dyestuffs disclosed in JP-B-59-28326, melocyanine dyestuffs disclosed in JP-A-59-89303, melocyanine dyestuffs disclosed in JP-A-8-129257, benzopyrane-based dyestuffs disclosed in JP-A-8-334897, and short wave type ketone-based dyestuffs and styryl-based dyestuffs disclosed in EP1048982A1.

Further examples of the sensitizing dye employable herein include infrared absorbers disclosed in the above cited JP-A-11-209001.

The sensitizing dyes of the invention, too, may be used singly or in combination of two or more thereof to advantage. The polymerizable composition of the invention may further comprise a known compound having an effect of further enhancing sensitivity or inhibiting polymerization inhibition incorporated therein as a cosensitizer.

Examples of such a cosensitizer include amines as described in M. R. Sander et al., "Journal of Polymer Society", Vol. 10, page 3,173, 1972, JP-B-44-20189, JP-A-51-82102, JP-A-52-134692, JP-A-59-138205, JP-A-60-84305, JP-A-62-18537, JP-A-64-33104, and Research Disclosure No. 33825. Specific examples of these compounds include triethanolamine, p-dimethylaminobenzoic acid ethyl ester, p-formyldimetylaniline, and p-methylthiodimethylaniline.

Further examples of such a cosensitizer include thiols and sulfides such as thiol compounds disclosed in JPA-53-702, JP-B-55-500806 and JP-A-5-142772, and disulfide compounds disclosed in JP-A-56-75643. Specific examples of these compounds include 2-mercaptobenzothiazole, 2-mercaptobenzoxazole, 2-mercaptobenzoimidazole, 2-mercapto-4(3H)-quinazoline, and β-mercaptonaphthalene.

Still further examples of such a cosensitizer include amino acid compounds (e.g., N-phenylglycine), organic metal compounds disclosed in JP-B-48-42965 (e.g., tributyltin acetate), hydrogen donors disclosed in JP-B-55-34414, sulfur compounds disclosed in JP-A-6-308727 (e.g., triathine), phosphorus compounds disclosed in JP-A-6-250387 (diethyl phosphite), and Si—H and Ge—H compounds disclosed in Japanese Patent Application No. 6-191605.

The amount of the photopolymerization initiator to be incorporated in the composition of the invention is from 0.01 to 60% by weight, more preferably from 0.05 to 30% by weight based on the total weight of the components of the polymerizable composition.

In the case where a sensitizing dye is used in the invention, the molar ratio of the photopolymerization initiator to the sensitizing dye in the polymerizable composition is from 100:0 to 1:99, preferably from 90:10 to 10:90, most preferably from 80:20 to 20:80.

The aforementioned cosensitizer, if any, is preferably used in an amount of from 0.01 to 50 parts by weight based on 1 part by weight of the photopolymerization initiator.

[Linear Organic Polymer]

The polymerizable composition of the invention preferably comprises a linear organic polymer incorporated therein as a binder. As such a "linear organic polymer" there may be used any linear organic polymer compatible with photopolymerizable ethylenically unsaturated compounds. Preferably, a water- or weak aqueous alkali-soluble or swelling linear organic polymer enabling aqueous development or weak aqueous alkali development is selected. The linear organic polymer is not only used as a film-forming agent for the composition but also selected and used properly depending on which is used water, weak aqueous alkali or organic solvent as a developer. For example, a water-soluble organic polymer can be used to effect aqueous development. Examples of such a linear organic polymer include addition polymers having a carboxylic acid group in its side chains as disclosed in JP-A-59-44615, JP-B-54-34327, JP-B-58-12577, JP-B-54-25957, JP-A-54-92723, JP-A-59-53836 and JP-A-59-71048. Specific examples of these addition polymers include methacrylic acid copolymers, acrylic acid copolymers, itaconic acid copolymers, crotonic acid copolymers, maleic acid copolymers, and partially-esterified maleic acid copolymers. Other examples of these addition polymers include acidic cellulose derivatives having a carboxylic acid group in its side chains. Besides these linear organic polymers, those obtained by the addition of a cyclic acid anhydride to an addition polymer having a hydroxyl group are useful. Particularly preferred among these linear organic polymers are [benzyl (meth)acrylate/(meth)acrylic acid/optionally other addition-polymerizable vinyl monomers] copolymers and [allyl (meth)acrylate/(meth)acrylic acid/optionally other other addition-polymerizable vinyl monomers] copolymers. Besides these linear organic polymers, polyvinyl pyrrolidones and polyethylene oxides are useful as linear organic polymers. In order to enhance the strength of the cured film, an alcohol-soluble polyamide or a polyether such as 2,2-bis-(4-hydroxyphenyl)-propane and epichlorohydrin can be used.

In particular, the linear organic polymer to be used in the invention is preferably an alkali-soluble polyurethane resin disclosed in JP-A-11-352691 from the standpoint of reactivity and compatibility.

The molecular weight of the polyurethane resin to be used in the polymerizable composition of the invention is preferably not smaller than 1,000, more preferably from 5,000 to 500,000 as calculated in terms of weight-average molecular weight.

These polymer compounds may be used singly or in admixture.

Preferred examples of the polyurethane resin include the following compounds, but the invention is not limited thereto. Most of the specific examples are shown in the form of combination of diisocyanate compound and diol compound used. The carboxyl group content is given as acid value.

1~4 (1st)

Poly(urethane urea) resin Diisocyanate compound used (mol %)

(1) 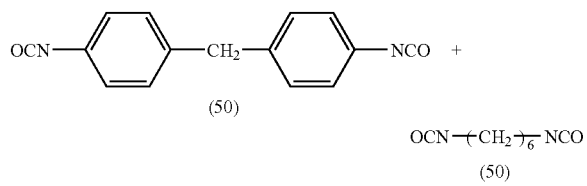

(2) 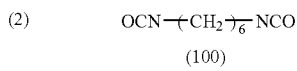

(3) 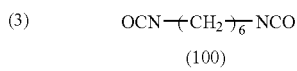

(4) 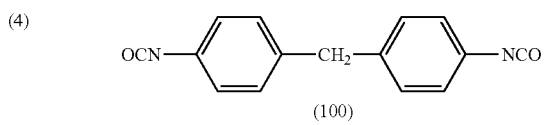

| | 1~4 (2nd) | | |
|---|---|---|---|
| Poly(urethane urea) resin | Diol compound and diamine, aminoalcohol or urea compound used (mol %) | | Acid value (meq/g) |
| (1) | 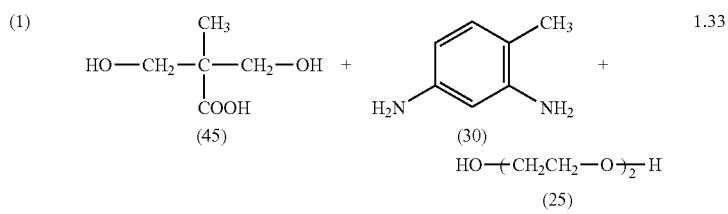 | | 1.33 |
| (2) | 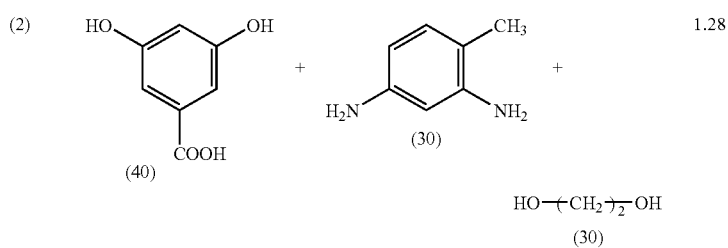 | | 1.28 |
| (3) | 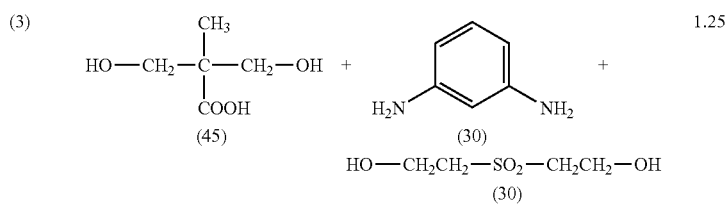 | | 1.25 |
| (4) | 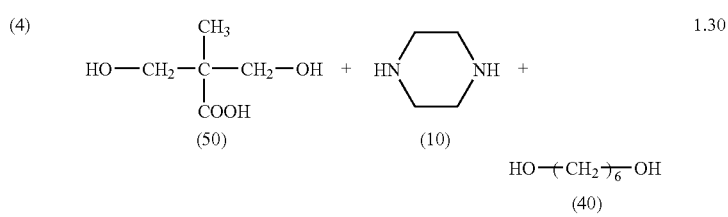 | | 1.30 |

5~7 (1st)
| Poly(urethane ester) resin | Diisocyanate compound used (mol %) |
|---|---|
| (5) | 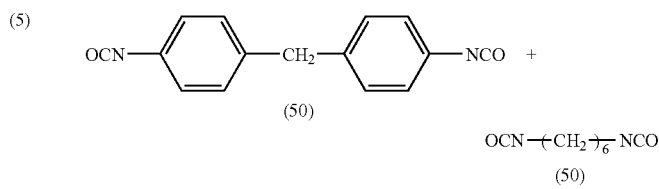 |
| (6) | 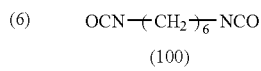 (100) |
| (7) | 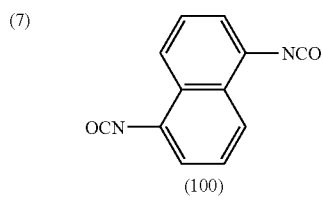 (100) |
5~7 (2nd)
| Poly(urethane ester) resin | Diol compound used (mol %) | Acid value (meq/g) |
|---|---|---|
| (5) | 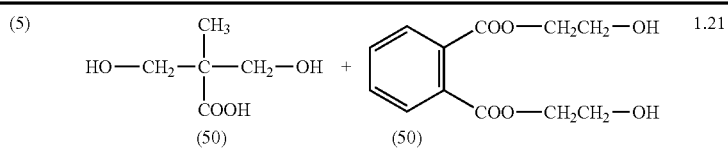 | 1.21 |
| (6) | 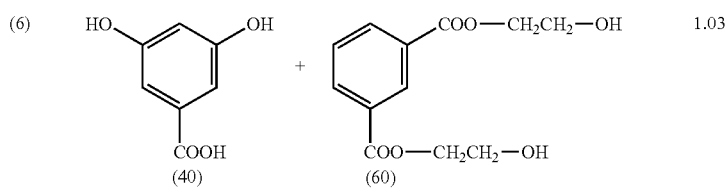 | 1.03 |
| (7) | 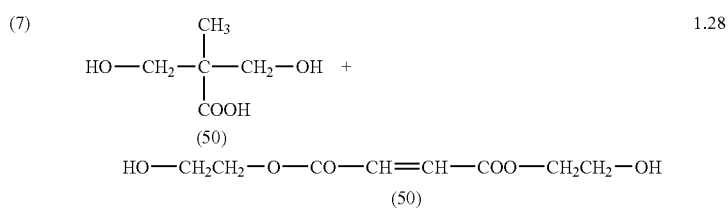 | 1.28 |

| Poly(urethane amide) resin | Diisocyanate compound used (mol %) | Diol compound used (mol %) | Add value (meq/g) |
|---|---|---|---|
| (8) | OCN—⟨C₆H₄⟩—CH₂—⟨C₆H₄⟩—NCO (50) + OCN—(CH₂)₆—NCO (50) | HO—CH₂—C(CH₃)(COOH)—CH₂—OH (50) + HO—CH₂CH₂—NH—OC—⟨C₆H₄⟩—CO—NH—CH₂CH₂—OH (50) | 1.22 |
| (9) | OCN—(CH₂)₆—NCO (100) | HO—⟨C₆H₃(OH)⟩—COOH (40) + HO—CH₂CH₂—NH—CO—CH=CH—CO—NH—CH₂CH₂—OH (60) | 1.12 |
| (10) | OCN—CH₂—⟨C₆H₄⟩—CH₂—NCO (100) | HO—CH₂CH₂—N(—CH₂CH₂—OH)—C(=O)—CH₂CH₂—COOH (50) + HO—CH₂CH₂—NH—CO—(CH₂)₂—CO—NH—CH₂CH₂—OH (50) | 1.25 |
| (11) | OCN—⟨naphthalene⟩—NCO (100) | HO—CH₂—C(CH₃)(COOH)—CH₂—OH (50) + HO—CH₂CH₂—NH—CO—(CH₂)₃—CO—NH—CH₂CH₂—OH (50) | 1.23 |

-continued

| Polyurethane resin | Diisocyanate compound used (mol %) | Diol compound used (mol %) | Add value (meq/g) |
|---|---|---|---|
| (12) | 4,4'-methylenebis(phenyl isocyanate) (100) | HO-CH₂-C(CH₃)(CH₂-OH)-COOH (50) + 5-methylbenzene-1,3-diol (20) + HO-(CH₂CH₂-O)₂-H (30) | 1.29 |
| (13) | 3,3'-dimethyl-4,4'-biphenyl diisocyanate (70) + OCN-(CH₂)₆-NCO (30) | HO-CH₂-C(CH₃)(CH₂-OH)-COOH (45) + 4,4'-(propane-2,2-diyl)diphenol (25) + HO-(CH₂CH₂-O)₂-H (30) | 1.15 |
| (14) | 4,4'-methylenebis(phenyl isocyanate) (60) + isophorone diisocyanate (40) | HO-CH₂-C(CH₃)(CH₂-OH)-COOH (50) + 4,4'-thiodiphenol (30) + HO-(CH₂)₆-OH (20) | 1.23 |

| Polyurethane resin | Structural formula (mol %) | Add value (meq/g) |
|---|---|---|

| Polyurethane resin | Structural formula (mol %) | Add value (meq/g) |
|---|---|---|
| (15) | -[CONH-C6H4-CH2-C6H4-NHCO]35-[C6H2(COOH)(COO-CH2CH2-O-)(HO-CO-)(-OCO-CH2CH2-O-)]25-[CONH-C6H4-CH2-NHCO]15-[O-CH2-C(CH3)2-CH2-O]15 | 2.18 |
| (16) | -[CONH-C6H4-CH2-C6H4-NHCO]35-[C6H2(COOR)(COO-CH2CH2-O-)(RO-CO-)(-OCO-CH2CH2-O-)]25-[CONH-C6H4-CH2-NHCO]15-[O-CH2-C(CH3)2-CH2-O]15 | 1.21 |
| (17) | -[CONH-C6H4-CH2-C6H4-NHCO]30-[C6H2(COOH)(COO-CH2CH2-O-)(HO-CO-)(-O-CH2CH2-OCO-)]25-[CONH-C6H10(CH3)2(CH2-NHCO-)]20-[O-(CH2)4-O]25 | 2.16 |

(18)
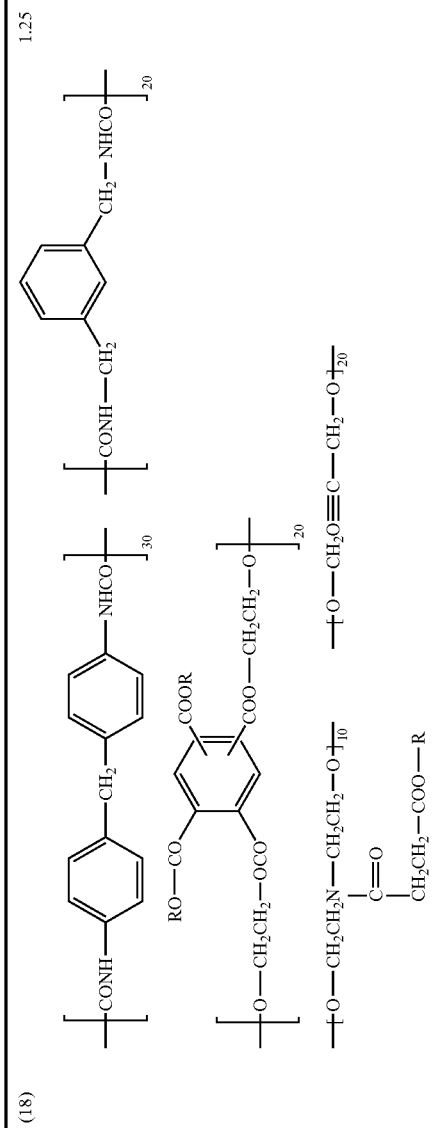
(19)
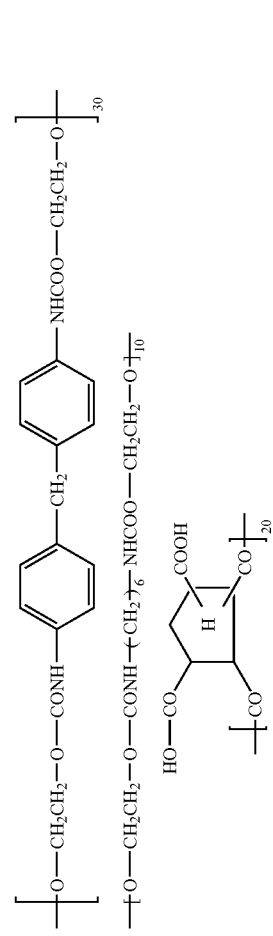
R = H

20~26 (1st)
| Polyurethane resin | Diisocyanate compound used (mol %) |
|---|---|
| (20) | 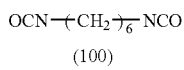<br>(100) |
| (21) | 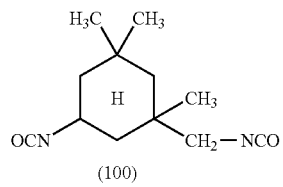<br>(100) |
| (22) | 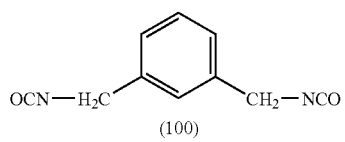<br>(100) |
| (23) | 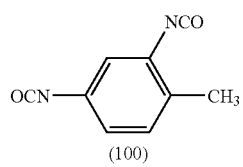<br>(100) |
| (24) | 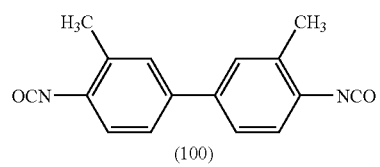<br>(100) |
| (25) | 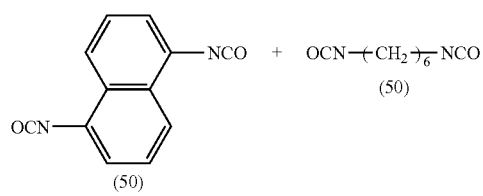<br>(50) (50) |
| (26) | 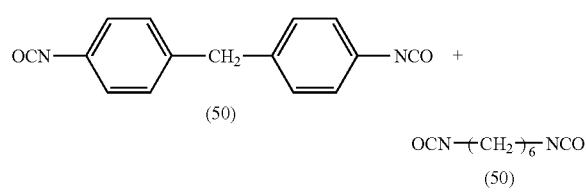<br>(50) (50) |
20~26 (2nd)
| Polyurethane resin | Diol compound used (mol %) | Residual carboxyl group content (meq/g) |
|---|---|---|

-continued
(20) 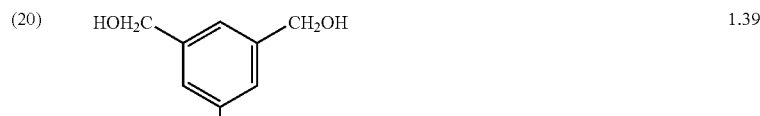 1.39
(21) 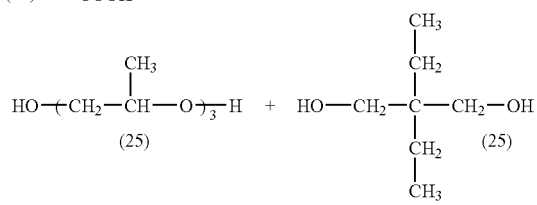 1.33
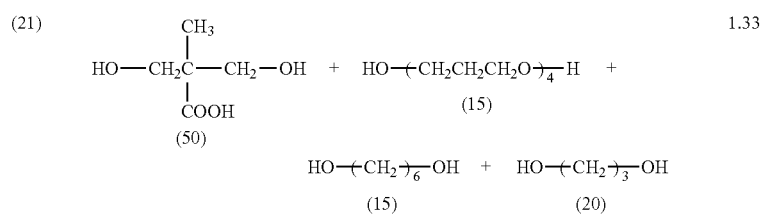
(22) 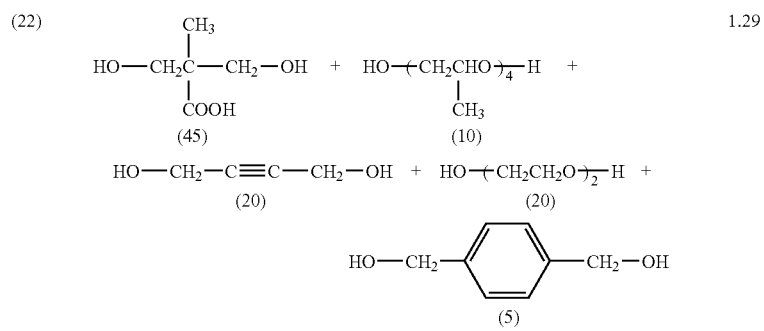 1.29
(23) 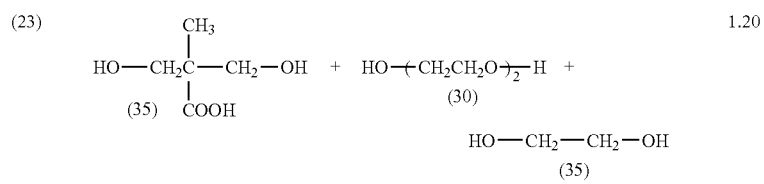 1.20
(24) 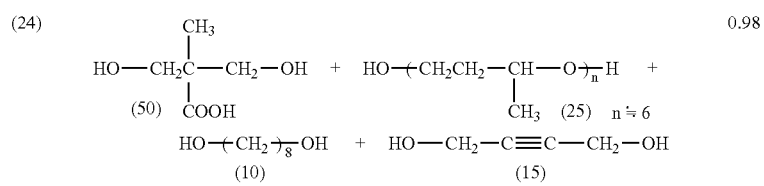 0.98
(25) 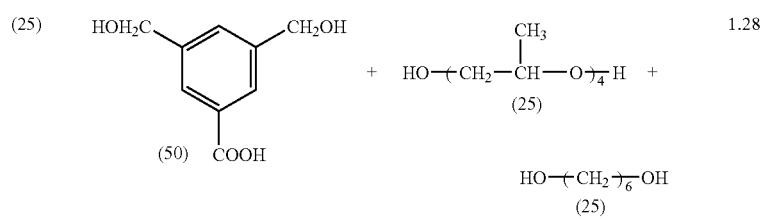 1.28

-continued
| | | |
|---|---|---|
| (26) | 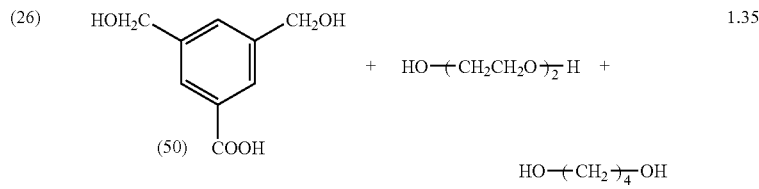 + HO—(CH₂CH₂O)₂—H + <br><br> HO—(CH₂)₄—OH | 1.35 |
27~32 (1st)
| Polyurethane resin | Diisocyanate compound used (mol %) |
|---|---|
| (27) | 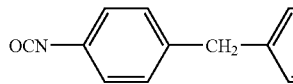 + <br>(60)<br> OCN—(CH₂)₆—NCO <br>(40) |
| (28) | 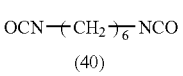 + <br>(70)<br> OCN—(CH₂)₆—NCO <br>(30) |
| (29) | 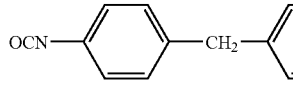 + <br>(40)<br> 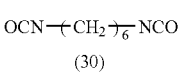 <br>(60) |
| (30) | 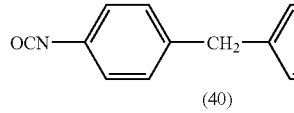 + <br>(70)<br> 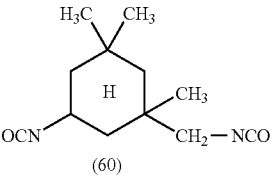 <br>(30) |
| (31) | 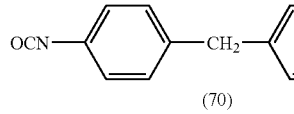 + <br>(60)<br> 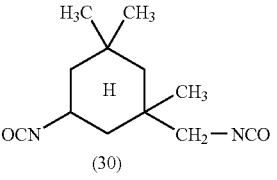 <br>(40) |

-continued
(32) 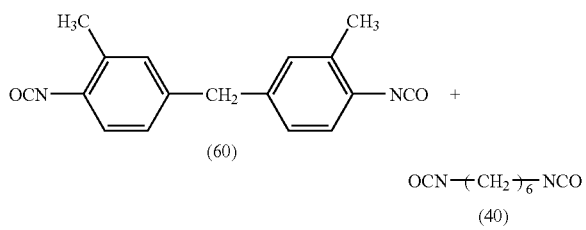
| Polyurethane resin | Diol compound used (mol%) | Residual carboxyl group content (meq/g) |
|---|---|---|
| (27) | 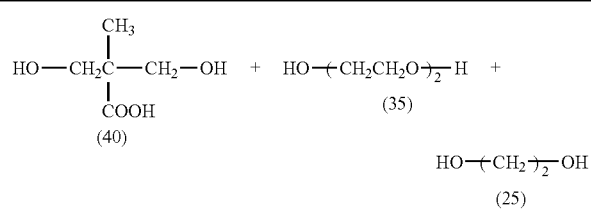 | 1.16 |
| (28) | 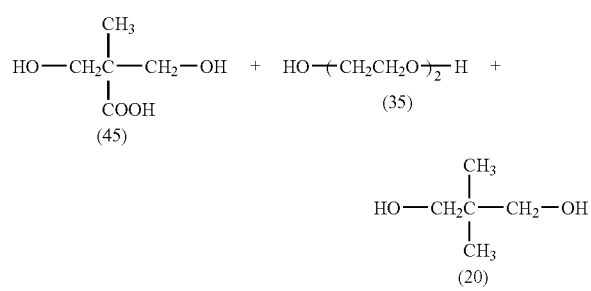 | 1.23 |
| (29) | 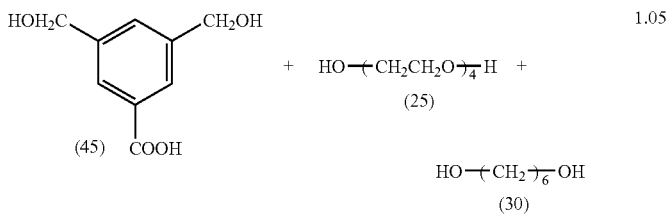 | 1.05 |
| (30) | 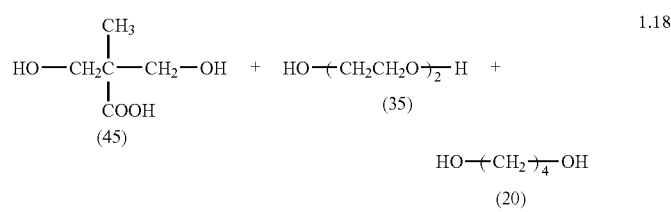 | 1.18 |
27~32 (2nd)

-continued

27~32 (2nd)

| Polyurethane resin | Diol compound used (mol%) | Residual carboxyl group content (meq/g) |
|---|---|---|
| (31) | HO—CH$_2$C(CH$_3$)(COOH)—CH$_2$—OH (40) + HO—(CH$_2$CH$_2$O)$_3$—H (40) + HO—CH$_2$C(CH$_3$)(CH$_3$)—CH$_2$—OH (20) | 1.03 |
| (32) | HO—CH$_2$C(CH$_3$)(COOH)—CH$_2$—OH (40) + HO—(CH$_2$CH$_2$O)$_2$—H (35) + HO—CH$_2$—CH=CH—CH$_2$—OH (25) | 1.10 |

| Polyurethane resin | Diisocyanate compound used (mol %) | Diol compound used (mol %) | Acid value (meq/g) |
|---|---|---|---|
| (33) | OCN—C$_6$H$_4$—CH$_2$—C$_6$H$_4$—NCO (80) + OCN—(CH$_2$)$_6$—NCO (20) | HO—CH$_2$—C(CH$_3$)(CO$_2$H)—CH$_2$—OH (80) + HO—(CH$_2$CHO)n—H with CH$_3$ side, Average molecular weight 1000, n=17 (20) | 1.40 |
| (34) | 2,4-TDI (NCO, NCO, CH$_3$) (80) + OCN—(CH$_2$)$_6$—NCO (20) | HO—CH$_2$—C(CH$_3$)(CO$_2$H)—CH$_2$—OH (80) + HO—(CH$_2$CHO)n—H with CH$_3$ side, Average molecular weight 1000, n=17 (20) | 1.70 |

-continued

| Polyurethane resin | Diisocyanate compound used (mol %) | Diol compound used (mol %) | Acid value (meq/g) |
|---|---|---|---|
| (35) | 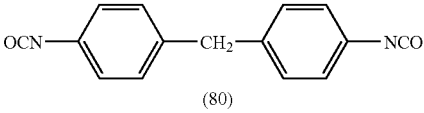 (80) + 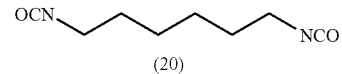 (20) | 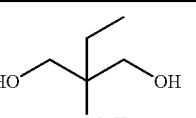 (80) + HO—(CH$_2$CHO)n—H  $\|$  CH$_3$ Average molecular weight 1000 n=17 (20) | 1.40 |
| (36) | 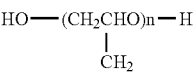 (80) + 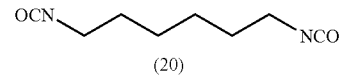 (20) | 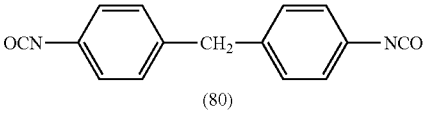 (89) + HO—(CH$_2$CHO)n—H  $\|$  CH$_3$ Average molecular weight 2000 n=34 (11) | 1.40 |

These linear organic polymers may be incorporated in the composition of the invention in an arbitrary amount. However, when the amount of the linear organic polymers is not greater than 90% by weight based on the total weight of the components of the composition, the results are good from the standpoint of strength of image formed. The amount of these linear organic polymers is preferably from 30% to 85%. The weight ratio of the photopolymerizable ethylenically unsaturated compound to the linear organic polymer is preferably from 1/9 to 7/3, more preferably from 3/7 to 5/5.

Polymerization Initiator

The polymerizable composition of the invention preferably comprises a small amount of a heat polymerization inhibitor incorporated therein besides the aforementioned basic components to inhibit unnecessary heat polymerization of polymerizable compounds having ethylenically unsaturated double bonds during the production or storage of the polymerizable composition. Examples of proper heat polymerization inhibitors include hydroquinone, p-methoxy phenol, di-t-butyl-p-cresol, pyrogallol, t-butylcatechol, benzoquinone, 4,4'-thiobis(3-methyl-6-t-butylphenol), 2,2'-methylenebis(4-methyl-6-t-butylphenol), and N-nitrosophenylhydroxyamine cerous salts. The amount of the heat polymerization initiator to be added is preferably from about 0.01 to 5% by weight based on the total weight of the composition. If necessary, a higher aliphatic acid derivative such as behenic acid and behenic acid amide or the like may be added so that it is maldistributed on the surface of the photosensitive layer during the drying procedure after coating to prevent polymerization inhibition due to oxygen. The amount of the higher aliphatic acid derivative to be added is preferably from about 0.5 to 10% by weight based on the total weight of the composition.

Coloring Material, etc.

The polymerizable composition of the invention may further comprise a dye or pigment incorporated therein for the purpose of coloring the photosensitive layer. In this arrangement, the resulting printing plate can be provided with improvements in so-called detectability such as viewability after plate making and adaptability to image density measuring instrument. As a coloring material there is preferably used a pigment in particular because most dyes cause the drop of sensitivity of photopolymerizable photosensitive layer. Specific examples of the coloring material employable herein include pigments such as phthalocyanine-based pigment, azo-based pigment, carbon black and titanium oxide, and dyes such as ethyl violet, crystal violet, azo-based dye, anthraquinone-based dye and cyanine-based dye. The amount of the dye or pigment to be added is preferably from about 0.5 to 5% by weight based on the total weight of the composition.

Other Additives

The photopolymerizable composition of the invention may further comprise known additives incorporated therein such as inorganic filler and plasticizer for improving the physical properties of cured layer and desensitizer for improving the ink affinity of the surface of the photosensitive layer.

Examples of the plasticizer employable herein include dioctyl phthalate, didodecyl phthalate, triethylene glycol dicaprylate, dimethyl glycol phthalate, tricresyl diphosphate, dioctyl adipate, dibutyl sebacate, and triacetyl glycerin. In the case where the binder is used, the plasticizer may be added in an amount of not greater than 10% by weight based on the total weight of the compound having ethylenically unsaturated double bonds and the binder.

The polymerizable composition of the invention may further comprise an ultraviolet initiator or heat crosslinking agent incorporated therein for enhancing the effect of heating/exposure after development to enhance the layer strength (press life) as described later.

The polymerizable composition of the invention may further comprise additives incorporated therein or there may be provided an interlayer for enhancing the adhesion between the photosensitive layer and the support or the removability of the unexposed photosensitive layer by development. For example, the addition or undercoating of a compound having a relatively strong interaction with substrate such as compound having a diazonium structure and phosphonic compound makes it possible to enhance adhesion and prolong press life. On the other hand, the addition or undercoating of a hydrophilic polymer such as polyacrylic acid and polysulfonic acid makes it possible to enhance the developability of non-image area and enhance the stain resistance.

The polymerizable composition of the invention is spread over a support in the form of solution in various organic solvents. Examples of the solvent employable herein include acetone, methyl ethyl ketone, cyclohexane, ethyl acetate, ethylene dichloride, tetrahydrofurane, toluene, ethylene glycol monomethyl ether, ethylene glycol monoethyl ether, ethylene glycol dimethyl ether, propylene glycol monomethyl ether, propylene glycol monoethyl ether, acetyl acetone, cyclohexanone, diacetone alcohol, ethylene glycol monomethyl ether acetate, ethylene glycol ethyl ether acetate, ethylene glycol monoisopropyl ether, ethylene glycol monobutyl ether acetate, 3-methoxypropanol, methoxymethoxy ethanol, diethylene glycol monomethyl ether, diethylene glycol monoethyl ether, diethylene glycol dimethyl ether, diethylene glycol diethyl ether, propylene glycol monomethyl ether acetate, propylene glycol monoethyl ether acetate, 3-methoxypropyl acetate, N,N-dimethylformamide, dimethyl sulfoxide, γ-butyrolactone, methyl lactate, and ethyl lactate. These solvents may be used singly or in admixture. The concentration of solid content in the coating solution is properly from 2 to 50% by weight.

The spread of the photosensitive layer over the support can mainly affect the sensitivity and developability of the photosensitive layer and the strength and press life of the exposed layer and thus is preferably predetermined properly according to the purpose. When the spread of the photosensitive layer over the support is too small, the resulting lithographic printing plate can leave something to be desired in press life. On the contrary, when the spread of the photosensitive layer over the support is too great, the resulting lithographic printing plate precursor exhibits a reduced sensitivity and thus takes much time to expose and longer time to develop to disadvantage. For the lithographic printing plate precursor for scanning exposure, which is a main aim of the invention, the spread of the photosensitive layer over the support is preferably from about 0.1 g/m$^2$ to 10 g/m$^2$, more preferably from 0.5 g/m$^2$ to 5 g/m$^2$ as calculated in terms of dried amount.

Support

In order to obtain the lithographic printing plate precursor, which is one of the main aims of the invention, the aforementioned photosensitive layer is preferably provided on a support having a hydrophilic surface. As such a hydrophilic support there may be used any known hydrophilic support for use in lithographic printing plate without limitation. The support to be used is preferably a dimensionally stable tabular material. Examples of such a material include paper, paper laminated with a plastic (e.g., polyethylene, polypropylene, polystyrene), metal sheet (e.g., aluminum, zinc, copper), plastic film (e.g., cellulose diacetate, cellulose triacetate, cellulose propionate, cellulose butyrate, cellulose acetobutyrate, cellulose nitrate, polyethylene terephthalate, polyethylene, polystyrene, polypropylene, polycarbonate, polyvinyl acetal), and paper or plastic film laminated or vacuum-coated with the aforementioned metal. The surface of the aforementioned support may be subjected to any proper physical or chemical treatment for the purpose of providing hydrophilicity or enhancing strength as necessary.

Particularly preferred examples of the support include paper, polyester film, and aluminum sheet. Particularly preferred among these support materials is aluminum sheet because it exhibits a good dimensional stability, is available at a relatively low cost and can provide a surface having an excellent hydrophilicity and strength when subjected to surface treatment as necessary. Further, a composite sheet comprising an aluminum sheet bonded to a polyethylene terephthalate film as disclosed in JP-B-48-18327 is preferred.

A preferred aluminum sheet is a pure aluminum sheet or an alloy sheet mainly composed of aluminum containing a slight amount of foreign elements. A plastic film laminated or vacuum-coated with aluminum may be used. Examples of foreign elements contained in the aluminum alloy include silicon, iron, manganese, copper, magnesium, chromium, zinc, bismuth, nickel, and titanium. The content of foreign elements in the alloy is 10% by weight at maximum. A particularly preferred aluminum material in the invention is pure aluminum. However, since perfectly pure aluminum can be difficultly produced from the standpoint of refining technique, aluminum containing trace amounts of foreign elements may be used. Thus, the aluminum sheet to be applied to the invention is not limited in its composition. Any known general-purpose aluminum sheet may be properly used. The thickness of the aluminum sheet to be used in the invention is from about 0.1 mm to 0.6 mm, preferably from about 0.15 mm to 0.4 mm, particularly from about 0.2 mm to 0.3 mm.

The support the surface of which is a metal, particularly aluminum, if used, is preferably subjected to roughening (graining), dipping in an aqueous solution of sodium silicate, zirconium potassium fluoride, phosphate or the like or surface treatment such as anodization before use.

The roughening of the surface of the aluminum sheet can be accomplished by various methods such as method involving the mechanical roughening of aluminum sheet, method involving the electrochemical dissolution and roughening of aluminum sheet and method involving the chemical selective dissolution of aluminum sheet. As the mechanical method there may be used any known method such as ball polishing, brushing, blasting method and buffing. As the electrochemical roughening method there may be used a method using alternating or direct current in a hydrochloric acid or nitric acid electrolyte. Alternatively, a method involving the combined use of alternating current and direct current may be used as disclosed in JP-A-54-63902. Prior to roughening the aluminum sheet, the aluminum sheet is subjected to treatment for removing the rolling oil from the surface thereof, e.g., degreasing with a surface active agent, organic solvent or alkaline aqueous solution.

The aluminum sheet thus roughened is preferably dipped in an aqueous solution of sodium silicate before use. As described in JP-B-47-5125, an aluminum sheet which has been anodized and then dipped in an aqueous solution of alkaline metal silicate is preferably used. The anodization of the aluminum sheet can be accomplished by passing electric current through the aluminum sheet as an anode in an electrolyte comprising, singly or in combination, aqueous or non-aqueous solutions of an inorganic acid such as phosphoric acid, chromic acid, sulfuric acid and boric acid or an organic acid such as oxalic acid and sulfamic acid or salt thereof.

Silicate electrodeposition as disclosed in U.S. Pat. No. 3,658,662 is useful as well.

A surface treatment involving the aforementioned anodization and sodium silicate treatment of an electrolytically grained support as disclosed in JP-B-46-27481, JP-A-52-58602 and JP-A-52-30503 is useful as well.

Further, an aluminum sheet which has been sequentially subjected to mechanical roughening, chemical etching, electrolytic graining, anodization and sodium silicate treatment as disclosed in JP-A-56-28893 is preferably used.

The aluminum sheet thus treated is preferably coated with a water-soluble resin such as polymer or copolymer having a polyvinylphosphonic acid or sulfonic acid group in its side chain, a polyacrylic acid, a water-soluble metal salt (e.g., zinc borate), a yellow dye, an amine salt or the like.

Moreover, a sol-gel-treated substrate having a functional group covalently bonded thereto which can cause addition reaction by radicals as disclosed in JP-A-7-159983 is preferably used.

Another preferred example of the support is one obtained by providing a water-resistant hydrophilic layer on an arbitrary support as a surface layer. Examples of such a surface layer include layer made of an inorganic pigment and a binder as disclosed in US Patent 3, 055,295 and JP-A-56-13168, hydrophilic swelling layer as disclosed in JP-A-9-80744, and sol-gel layer made of titanium oxide, polyvinyl alcohol and silicic acids as disclosed in JP-T-8-507727.

The aforementioned hydrophilicization treatment is effected not only for the purpose of rendering the surface of the support hydrophilic but also for the purpose of preventing harmful reaction of the polymerizable composition disposed on the support and enhancing the adhesion of the support to the photosensitive layer.

Protective Layer

In the case where the invention is applied to the lithographic printing plate precursor for scanning exposure, a protective layer may be further provided on the polymerizable composition layer because the lithographic printing plate precursor for scanning exposure is normally subjected to exposure in the atmosphere. The protective layer acts to prevent the entrance of a low molecular compound present in the atmosphere which inhibits the image formation reaction in the photosensitive layer caused by exposure such as basic material in the photosensitive layer, making it possible to expose the lithographic printing plate precursor for scanning exposure to light in the atmosphere. Accordingly, the protective layer is required to have a low permeability to low molecular compounds. The protective layer is also required to give substantially no inhibition to transmission of light for exposure. The protective layer is further required to have an excellent adhesion to the photosensitive layer. The protective layer preferably can be easily removed at the development step after exposure. Designs concerning protective layer have been heretofore proposed. For the details of these designs, reference can be made to U.S. Pat. No. 3,458,311 and JP-A-55-49729. As the material of the protective layer there may be used, e.g., a water-soluble polymer compound having a relatively good crystallinity. Specific examples of such a water-soluble polymer compound include water-soluble polymers such as polyvinyl alcohol, polyvinyl pyrrolidone, acidic cellulose, gelatin, gum arabic and polyacrylic acid. Among these water-soluble polymers, the polyvinyl alcohol can be used as a main component to give best results in basic properties such as oxygen barrier properties and removability by development. The polyvinyl alcohol to be used in the protective layer may be partly substituted by ester, ether and acetal so far as it contains an unsubstituted vinyl alcohol unit for providing necessary oxygen barrier properties and water solubility. Similarly, the polyvinyl alcohol may partly have other copolymer components. Specific examples of the polyvinyl alcohol include one which has been hydrolyzed by from 71 to 100 mol-% to have a molecular weight of from 300 to 2,400 as calculated in terms of weight-average molecular weight. Specific examples of these polyvinyl alcohols include PVA-105, PVA-110, PVA-117, PVA-117H, PVA-120, PVA-124, PVA-124H, PVA-CS, PVA-CST, PVA-HC, PVA-203, PVA-204, PVA-205, PVA-210, PVA-217, PVA-220, PVA-224, PVA-217EE, PVA-217E, PVA-220E, PVA-224E, PVA-405, PVA-420, PVA-613 and L-8 (produced by Kuraray Co., Ltd.).

The components of the protective layer (selection of PVA, use of additives), the spread of the protective layer, etc. are predetermined taking into account permeability to low molecular materials and removability by development as well as foggability, adhesion and scratch resistance. In general, the higher the percent hydrolysis of PVA used is (the higher the content of unsubstituted vinyl alcohol unit in the protective layer is) and the greater the thickness of the protective layer is, the higher is the permeability to low molecular compounds. This is advantageous in sensitivity. However, when the permeability to low molecular compounds is extremely raised, unnecessary polymerization reaction can occur during production or storage. Further, unnecessary fogging or image thickening can occur during imagewise exposure. Adhesion to image area and scratch resistance are extremely important from the standpoint of handle ability. In other words, when a hydrophilic layer made of a water-soluble polymer is laminated on a lipophilic polymer layer, layer exfoliation can easily occur due to lack of adhesion. In an attempt to enhance the adhesion between the two layers, various proposals have been made. For example, U.S. Pat. Nos. 2,925,501 and 44,563 disclose that the lamination of a mixture of a hydrophilic polymer mainly composed of a polyvinyl alcohol and an acrylic emulsion, water-soluble vinyl pyrrolidone-vinyl acetate copolymer or the like in an amount of from 20 to 60% by weight on a polymer layer makes it possible to give a sufficient adhesion. For the protective layer of the invention, all these known techniques can be employed. For the details of the method for spreading such a protective layer, reference can be made to U.S. Pat. No. 3,458,311 and JP-A-55-49729.

The protective layer may be provided with other functions. For example, the photosensitive composition to be used in the case where laser beam is used as a light source is required to have an excellent sensitivity to wavelength of the laser beam but have no sensitivity to other wavelength ranges. For example, when the light source emits light having an infrared wavelength range of not lower than 750 nm, the photosensitive composition can be used substantially in daylight but can be actually sensitive to light having a short wavelength range such as light from fluorescent lamp. In this case, a coloring material (water-soluble dye, etc.) which exhibits an excellent transmission of light from light source and can efficiently absorb light having a wavelength range of less than 700 nm is preferably added.

Referring to another example, the photosensitive composition can be used substantially under safelight so far as the light source emits light having an ultraviolet wavelength range of not higher than 450 nm. In actuality, however, the photosensitive composition can be sensitive to visible light having a wavelength range of not lower than 500 nm. In this case, the addition of a coloring material (water-soluble dye, etc.) which exhibits an excellent transmission of light from light source and can efficiently absorb light having a wavelength range of not lower than 500 nm makes it possible to further enhance adaptability to safelight without dropping sensitivity.

In order to use a photographic material comprising the polymerizable composition of the invention as an image-forming material, the photographic material is normally imagewise exposed to light, and then freed of the unexposed photosensitive layer with a developer to obtain an image. As a desirable developer with which the polymerizable composition is used to prepare a lithographic printing plate precursor there may be used a developer as disclosed in JP-B-57-7427. An inorganic alkaline agent such as sodium silicate, potassium silicate, sodium hydroxide, potassium hydroxide, lithium hydroxide, tribasic sodium phosphate, dibasic sodium phosphate, tribasic ammonium phosphate, dibasic ammonium phosphate, sodium metasilicate, sodium bicarbonate and aqueous ammonia or an organic alkaline agent such as monoethanolamine and diethanolamine is preferably used. Such an alkaline solution is added in a concentration of from 0.1 to 10% by weight, preferably from 0.5 to 5% by weight.

Such an aqueous alkaline solution may contain a small amount of a surface active agent or an organic solvent such as benzyl alcohol, 2-phenoxy ethanol and 2-butoxy ethanol as necessary as described in U.S. Pat. Nos. 3,375,171 and 3,615,480.

Developers as disclosed in JP-A-50-26601, JP-A-58-54341, JP-B-56-39464 and JP-B-56-42860 are excellent as well.

Referring to the process for the preparation of printing plate from the lithographic printing plate precursor, which is a suitable usage of the polymerizable composition of the invention, the lithographic printing plate precursor may be entirely heated before or during exposure or during the period between exposure and development.

As the method for exposure of the lithographic printing plate precursor for scanning exposure of the invention there may be used any known method without limitation. As a light source there is preferably used laser beam. As an available laser beam source which emits laser beam having a wavelength range of from 350 to 450 nm there may be used any of the following lasers.

Examples of gas lasers include Ar ion lasers (364 nm, 351 nm; 10 mW–1 W), Kr ion lasers (356 nm, 351 nm; 10 mW–1 W), and He—Cd lasers (441 nm, 325 nm; 1 mW–100 m).

Examples of solid lasers include combination of Nd: YAG ($YVO_4$) and SHG crystal (x2) (355 mm; 5 mW–1 W), and combination of Cr: LiSAF and SHG crystal (430 nm; 10 mW).

Examples of semiconductor lasers include $KNbO_3$, ring resonator (430 nm; 30 mW), combination of waveguide type wavelength conversion element and AlGaAs or InGaAs semiconductor (380 nm–450 bm; 5 mW–100 mW), combination of waveguide type wavelength conversion element and AlGaInP or AlGaAs semiconductor (300 nm–350 bm; 5 mW–100 mW), and GaInN (350 nm–450 nm; 5 mW–30 mW).

Examples of pulse lasers include $N_2$ laser (337 nm; pulse: 0.1 to 10 mJ), and XeF (351 nm; pulse: 10–250 mJ).

Particularly preferred among these lasers is AlGaInN semiconductor laser (commercially available InGaN-based semiconductor laser: 400–410 nm; 5–30 mW) from the standpoint of wavelength properties and cost.

Other examples of available light sources having a wavelength range of from 450 nm to 700 nm which can be preferably used include Ar+ laser (488 nm), YAG-SHG laser (532 nm), He—Ne laser (633 nm), He—Cd laser, and red semiconductor laser (650–690 nm). Examples of available light sources having a wavelength range of from 700 nm to 1,200 nm which can be preferably used include semiconductor laser (800–850 nm), and Nd-YAG laser (1,064 nm).

Further examples of light sources which can be used herein include ultrahigh, high, middle and low voltage mercury vapor lamps, chemical lamps, carbon arc lamp, xenon lamp, metal halide lamp, and ultraviolet laser lamps (ArF excima laser, KrF excima laser). Examples of radiation which can be used herein include electron ray, X ray, ion beam, and far infrared ray. Particularly preferred among these light sources is the aforementioned laser beam source having a wavelength range of not lower than 350 nm from the standpoint of cost.

As the exposing mechanism there may be used inner drum process, external drum process, and flat bed process. The photosensitive layer of the invention can be made of a component having a high water solubility so that it can be dissolved in neutral water or weakly alkaline aqueous solution. The lithographic printing plate precursor having such an arrangement can be mounted on the printing machine so that it is subjected to on-the-machine exposure and development process.

The polymerizable composition of the invention can be widely used for purposes known for photo-setting resin without limitation besides for lithographic printing plate precursor for scanning exposure. For example, by applying the invention to a liquid polymerizable composition optionally combined with a cationically polymerizable composition, a high sensitivity optical imaging material can be obtained. By utilizing the change of refractivity accompanying photopolymerization, a hologram material can be provided. By utilizing the change of surface viscosity accompanying photopolymerization, the invention can be applied to various transferring materials (release photographic material, toner development photographic material, etc.). The invention can be applied to photo-setting of microcapsule. The invention can be applied also to the production of electronic materials such as photoresist. The invention can be applied further to ink and photo-setting resin material such as coating compound and adhesive.

The invention will be further described in the following examples, but the invention should not be construed as being limited thereto.

[Synthesis of Compounds of the Invention Having Structures Represented By the General Formulae (I) and (II)]

<General Synthesis Methods>

The synthesis of the aforementioned compounds of the invention (crosslinking agents having structures represented by the general formulae (I) and (II)) can be easily accomplished by the following methods 1 and 2.

(Method 1)

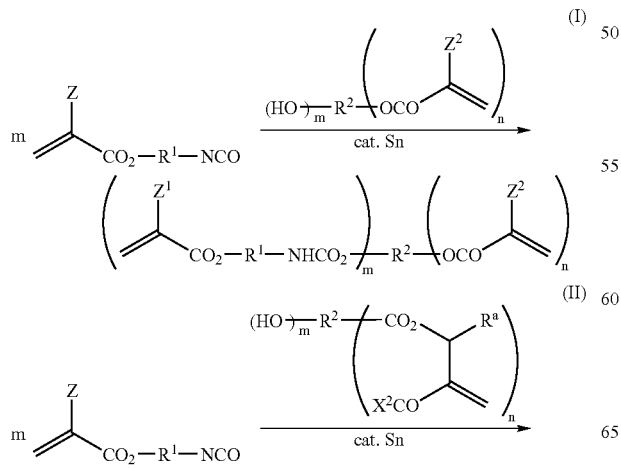

(Method 2)

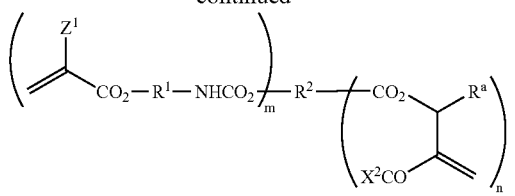

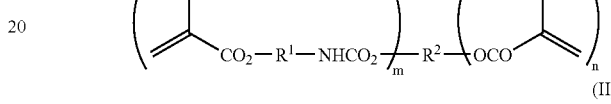

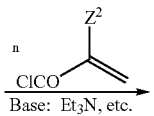

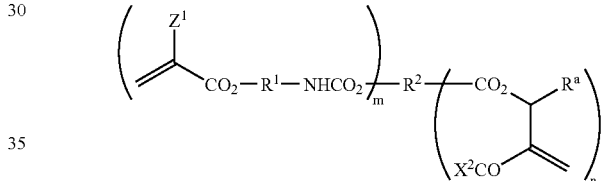

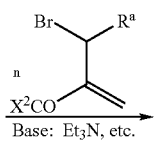

SYNTHESIS EXAMPLE 1

Synthesis of I-10: (Example of Method 1)

In a flask were charged 0.2 mols of glycerol dimethacrylate, 0.2 mols of 2-methacrtyloylethyl isocyanate, 0.002 mols of dibutyltin dilaurate and 300 ml of tetrahydrofurane. The mixture was then stirred at 50° C. for 5 hours. Thereafter, the temperature of the mixture was returned to room temperature. The solvent was then removed under reduced pressure. The residue was washed with hexane, and then dried to obtain a desired compound I-10 in a yield of 95%.

The structure of the compound was identified by NMR, MASS and IR.

<NMR data>: $^1$H NMR (300 MHz, CDCl$_3$): δ6.11 (3H, s), 5.59 (3H, s), 5.40–5.25 (1H, m), 5.08–4.98 (1H, m), 4.43–4.15 (6H, m), 3.55–3.43 (2H, m), 1.87 (9H, s).

SYNTHESIS EXAMPLE 2

Synthesis of I-15: (Example of Method 1)

In a flask were charged 0.2 mols of glycerol monomethacrylate, 0.2 mols of 2-methacrtyloylethyl isocyanate, 0.002 mols of dibutyltin dilaurate and 300 ml of tetrahydrofurane. The mixture was then stirred at 50° C. for 5 hours. Thereafter, the temperature of the mixture was returned to room temperature. The solvent was then removed under reduced pressure. The residue was washed with hexane, and then dried to obtain a desired compound I-15 in a yield of 90%.

The structure of the compound was identified by NMR, MASS and IR.

<NMR data>: $^1$H NMR (300 MHz, CDCl$_3$): δ6.13 (3H, s), 5.59 (3H, s), 5.38–5.0 (3H, m), 4.40–4.08 (8H, m), 3.55–3.38 (2H, m), 1.95 (9H, s).

SYNTHESIS EXAMPLE 2

Synthesis of II-2: (Example of Method 2)

In a flask were charged 0.2 mols of 2-methacrtyloylethyl isocyanate, 0.2 mols of sodium 4-hydroxybutanoate, 0.002 mols of dibutyltin dilaurate and 300 ml of N,N'-dimethylacetamide. The mixture was then stirred at 50° C. for 5 hours. Thereafter, the temperature of the mixture was returned to room temperature. To the mixture were then added 0.2 mols of methyl 2-bromomethacrylate. To the mixture were then added dropwise 0.2 mols of triethylamine with stirring in 1 hour. After dropwise addition, the mixture was stirred at 50° C. for 5 hours. The temperature of the mixture was returned to room temperature. To the mixture was then added 300 ml of water. The mixture was extracted with ethyl acetate, dried over sodium sulfate, and then filtered. The solvent was then removed from the filtrate under reduced pressure to obtain a desired compound II-2 in a yield of 70%.

The structure of the compound was identified by NMR, MASS and IR.

Thus, all the exemplified compounds can be synthesized.

[Example 1 of Photopolymerizable Composition (Preparation of Support)

An aluminum sheet having a thickness of 0.3 mm was dipped in a 10 wt-% sodium hydroxide solution at 60° C. for 25 seconds so that it was etched. The aluminum sheet thus etched was washed with flowing water, neutralized and washed with a 20 wt-% nitric acid solution, and then washed with water. The aluminum sheet thus process was then subjected to electrolytic roughening with a sinusoidal AC current at an anodization current density of 300 coulomb/dm$^2$ in a 1 wt-% aqueous solution of nitric acid. Subsequently, the aluminum sheet thus roughened was dipped in a 1 wt-% aqueous solution of sodium hydroxide at 40° C. for 5 seconds, dipped in a 30 wt-% aqueous solution of sulfuric acid at 60° C. for 40 seconds so that it was desmutted, and then subjected to anodization at a density current of 2 A/cm$^2$ in a 20 wt-% aqueous solution of sulfuric acid for 2 minutes to form an anodized film to a thickness of 2.7 g/m$^2$. The aluminum sheet thus anodized was then measured for surface roughness. The result was 0.3 μm as calculated in terms of Ra according to JIS B0601.

The following sol-gel reaction solution was spread over the back surface of the substrate thus processed using a bar coater, and then dried at 100° C. for 1 minute to prepare a support having a back coat layer in a dried spread of 70 mg/m$^2$.

Sol-gel Reaction Solution

| Tetraethyl silicate | 50 parts by weight |
| Water | 20 parts by weight |
| Methanol | 15 parts by weight |
| Phosphoric acid | 0.05 parts by weight |

When the aforementioned components were mixed with stirring, heat generation began in about 5 minutes. The reaction was then allowed to proceed for 60 minutes. Thereafter, to the reaction solution was added the following solution to prepare a back coat layer coating solution.

| Pyrogallol-formaldehyde condensation resin (molecular weight: 2,000) | 4 parts by weight |
| Dimethyl phthalate | 5 parts by weight |
| Fluorine-based surface active agent (N-butylperfluorooctane sulfonamide ethyl acrylate/polyoxyethylene acrylate copolymer: molecular weight: 20,000) | 0.7 parts by weight |
| Methanol silica sol (produced by NISSAN CHEMICAL INDUSTRIES, LTD.; methanol content: 30% by weight) | 50 parts by weight |
| Methanol | 800 parts by weight |

(Preparation of Photosensitive Layer)

A photopolymerizable composition having the following formulation (photosensitive layer-forming solution) was spread over the aluminum sheet thus processed to a dried thickness of 1.5 g/m$^2$, and then dried at 100° C. for 1 minute to form a photosensitive layer.

(Photosensitive Layer-forming Solution)

| Inventive or comparative compound [X] set forth in Table 1 below | 1.1 g |
| Photopolymerization initiator [Y] set forth in Table 1 below | 0.2 g |
| Polymer binder [Z] set forth in Table 1 below | 0.9 g |
| Additive [S] set forth in Table 1 | 0.2 g |
| Heat polymerization inhibitor (N-nitrosophenyl hydroxylamine aluminum salt) | 0.01 g |
| Pigment dispersion | 2.0 g |

| Formulation of pigment dispersion | |
| --- | --- |
| Pigment Blue 15:6 | 15 parts by weight |
| Allyl methacrylate/methacrylic acid copolymer (copolymerization molar ratio 83/17) | 10 parts by weight |
| Cyclohexanone | 15 parts by weight |
| Methoxypropyl acetate | 20 parts by weight |
| Propylene glycol monomethyl ether | 40 parts by weight |
| Methyl ethyl ketone | 20 g |
| Propylene glycol monomethyl ether | 20 g |

(Preparation of Protective Layer)

A 3 wt-% aqueous solution of a polyvinyl alcohol (saponification degree: 98 mol-%; polymerization degree: 550) was spread over the aforementioned photosensitive layer in a dried amount of 2 g/m², and then dried at 100° C. for 2 minutes.

(Evaluation of Sensitivity)

The photographic materials thus obtained were each evaluated for sensitivity using different light sources depending on their own exposing wavelength.

For example, these photographic materials were exposed to light from a semiconductor laser having a wavelength of 410 nm, an FD-YAG laser having a wavelength of 532 nm or a semiconductor laser having a wavelength of 830 nm in the atmosphere. These photographic materials thus exposed were each dipped in a developer having the following formulation at 25° C. for 10 seconds so that they were developed. The sensitivity under the respective exposing condition was then calculated in mJ/cm² from the minimum exposure at which an image can be formed. The smaller this value is, the higher is the sensitivity. However, since the energy possessed by one photon differs with wavelength of light source, simple consideration shows that the shorter the wavelength of light source is, the easier can be exposed the photographic material even when the aforementioned exposure is small. In short, as the wavelength of light source is shorter, the photographic material exhibits a higher sensitivity. Accordingly, Table 2 doesn't make sense in the comparison of sensitivity among different exposing conditions but merely shows the comparison of inventive examples with comparative examples under the same exposing conditions. The results are set forth in Table 2.

(Formulation of Developer)

| DV-2 (produced by Fuji Photo Film Co., Ltd.) | 200 g |
| Water | 800 g |

(Evaluation of Temperature Dependence of Sensitivity)

The photographic materials were each exposed to light from the respective laser in the atmosphere in the same manner as in the evaluation of sensitivity, heated to 120° C. for 20 seconds, and then dipped in the developer having the aforementioned formulation at 25° C. for 10 seconds so that they were developed. The minimum exposure at which an image can be formed was then determined. By determining the ratio of the minimum exposure under the heating conditions to the minimum exposure under the aforementioned unheated conditions, an index of temperature dependence of sensitivity was given. As this ratio is closer to 1, the photographic material is less subject to effect of temperature and hence exhibits better properties.

(Evaluation of Storage Stability)

The aforementioned unexposed photographic materials were each allowed to stand under high temperature conditions (60° C.) for 3 days, and then subjected to laser exposure in the same manner as mentioned above. The energy required for recording was then calculated. The energy ratio of before to after storage at high temperature (energy after storage at high temperature/energy before storage at high temperature) was then determined. It is desired from producibility as well as storage stability that this energy ratio is not grater than 1.1. The results of this evaluation, too, are set forth in Table 2 below.

(Press Life)

Using LITHRONE, which is a printing machine produced by Komori Corporation, provided with the unheated development samples which had been evaluated for sensitivity, printing was made with a commercially available ecoink. The number of sheets of paper on which printing can be made using the photoreceptor was then determined to give an index of press life.

The press life was represented relative to the value of the first example exposed at 410 nm, 532 nm and 830 nm as 100 for reference. Accordingly, the greater this value is, the longer is the press life. The results of evaluation, too, are set forth in Table 2 below.

TABLE 1

| | Photographic material | | | | |
|---|---|---|---|---|---|
| | X | Y | Z | S | Light source (nm) |
| Example 1 | I-3 | Y-1 | Z-1 | S-1 | 410 |
| Example 2 | I-7 | Y-1 | Z-1 | S-1 | 410 |
| Example 3 | I-10 | Y-1 | Z-2 | S-1 | 410 |
| Example 4 | I-16 | Y-2 | Z-3 | S-2 | 410 |
| Example 5 | I-20 | Y-1 | Z-2 | S-2 | 410 |
| Example 6 | II-2 | Y-2 | Z-1 | S-2 | 410 |
| Example 7 | II-10 | Y-1 | Z-3 | S-2 | 410 |
| Example 8 | II-20 | Y-2 | Z-3 | S-2 | 410 |
| Comparative Example 1 | X-1 | Y-1 | Z-1 | S-1 | 410 |
| Comparative Example 2 | X-2 | Y-1 | Z-1 | S-1 | 410 |
| Comparative Example 3 | X-3 | Y-1 | Z-2 | S-1 | 410 |
| Comparative Example 4 | X-4 | Y-2 | Z-3 | S-2 | 410 |
| Comparative Example 5 | X-5 | Y-1 | Z-2 | S-2 | 410 |
| Comparative Example 6 | X-6 | Y-2 | Z-1 | S-2 | 410 |
| Comparative Example 7 | X-7 | Y-1 | Z-3 | S-2 | 410 |
| Comparative Example 8 | X-8 | Y-2 | Z-3 | S-2 | 410 |
| Example 9 | I-2 | Y-3 | Z-1 | S-1 | 532 |
| Example 10 | I-6 | Y-3 | Z-3 | S-2 | 532 |
| Example 11 | I-12 | Y-4 | Z-1 | S-1 | 532 |
| Example 12 | I-18 | Y-4 | Z-2 | S-2 | 532 |
| Example 13 | I-25 | Y-3 | Z-2 | S-1 | 532 |
| Example 14 | II-4 | Y-5 | Z-1 | S-2 | 532 |
| Example 15 | II-12 | Y-3 | Z-2 | S-2 | 532 |
| Example 16 | II-23 | Y-5 | Z-3 | S-1 | 532 |
| Comparative Example 9 | X-9 | Y-3 | Z-1 | S-1 | 532 |
| Comparative Example 10 | X-10 | Y-3 | Z-3 | S-2 | 532 |
| Comparative Example 11 | X-11 | Y-4 | Z-1 | S-1 | 532 |
| Comparative Example 12 | X-12 | Y-4 | Z-2 | S-2 | 532 |
| Comparative Example 13 | X-13 | Y-3 | Z-3 | S-1 | 532 |
| Comparative Example 14 | X-14 | Y-5 | Z-1 | S-2 | 532 |
| Comparative Example 15 | X-15 | Y-3 | Z-2 | S-2 | 532 |
| Comparative Example 16 | X-16 | Y-5 | Z-3 | S-1 | 532 |

TABLE 1-continued

| | Photographic material | | | | |
|---|---|---|---|---|---|
| | X | Y | Z | S | Light source (nm) |
| Example 17 | I-5 | Y-6 | Z-4 | S-3 | 830 |
| Example 18 | I-11 | Y-6 | Z-4 | S-4 | 830 |
| Example 19 | I-15 | Y-7 | Z-3 | S-3 | 830 |
| Example 20 | I-19 | Y-7 | Z-3 | S-4 | 830 |
| Example 21 | I-27 | Y-7 | Z-3 | S-1 | 830 |
| Example 22 | II-12 | Y-8 | Z-4 | S-3 | 830 |
| Example 23 | II-24 | Y-7 | Z-3 | S-1 | 830 |
| Example 24 | II-27 | Y-8 | Z-3 | S-1 | 830 |
| Comparative Example 17 | X-17 | Y-6 | Z-4 | S-3 | 830 |
| Comparative Example 18 | X-18 | Y-6 | Z-4 | S-4 | 830 |
| Comparative Example 19 | X-19 | Y-7 | Z-3 | S-3 | 830 |
| Comparative Example 20 | X-20 | Y-7 | Z-3 | S-4 | 830 |
| Comparative Example 21 | X-21 | Y-7 | Z-3 | S-1 | 830 |
| Comparative Example 22 | X-22 | Y-8 | Z-4 | S-3 | 830 |
| Comparative Example 23 | X-23 | Y-7 | Z-3 | S-1 | 830 |
| Comparative Example 24 | X-24 | Y-8 | Z-3 | S-1 | 830 |
| Comparative Example 25 | X-25 | Y-2 | Z-3 | S-2 | 410 |
| Comparative Example 26 | X-26 | Y-2 | Z-3 | S-2 | 410 |
| Comparative Example 27 | X-27 | Y-2 | Z-3 | S-2 | 410 |
| Comparative Example 28 | X-28 | Y-2 | Z-3 | S-2 | 410 |
| Comparative Example 29 | X-25 | Y-7 | Z-3 | S-3 | 830 |
| Comparative Example 30 | X-26 | Y-7 | Z-3 | S-3 | 830 |
| Comparative Example 31 | X-27 | Y-7 | Z-3 | S-3 | 830 |
| Comparative Example 32 | X-28 | Y-7 | Z-3 | S-3 | 830 |

TABLE 2

| | Results of evaluation | | | |
|---|---|---|---|---|
| | Sensitivity (mJ/cm$^2$) | Temperature dependence of sensitivity (ratio) | Storage stability (ratio) | Press life (index) |
| Example 1 | 0.06 | 1.1 | 1.1 | 100 (Reference of 410 nm) |
| Example 2 | 0.06 | 1.1 | 1.1 | 100 |
| Example 3 | 0.05 | 1.1 | 1.1 | 150 |
| Example 4 | 0.05 | 1.1 | 1.1 | 150 |
| Example 5 | 0.05 | 1.1 | 1.1 | 130 |
| Example 6 | 0.07 | 1.1 | 1.1 | 110 |
| Example 7 | 0.05 | 1.1 | 1.1 | 140 |
| Example 8 | 0.07 | 1.1 | 1.1 | 100 |
| Comparative Example 1 | 0.08 | 3.0 | 2.0 | 70 |
| Comparative Example 2 | 0.08 | 4.0 | 2.0 | 70 |
| Comparative Example 3 | 0.08 | 5.0 | 1.5 | 70 |
| Comparative Example 4 | 0.10 | 3.0 | 2.5 | 80 |
| Comparative Example 5 | 0.09 | 4.0 | 2.0 | 80 |
| Comparative Example 6 | 0.10 | 3.0 | 1.5 | 80 |
| Comparative Example 7 | 0.07 | 4.0 | 1.5 | 80 |
| Comparative Example 8 | 0.10 | 3.0 | 2.0 | 80 |
| Example 9 | 0.15 | 1.1 | 1.0 | 100 (Reference of 532 nm) |
| Example 10 | 0.15 | 1.1 | 1.1 | 100 |
| Example 11 | 0.1 | 1.1 | 1.0 | 120 |
| Example 12 | 0.15 | 1.1 | 1.1 | 110 |
| Example 13 | 0.1 | 1.1 | 1.1 | 150 |
| Example 14 | 0.1 | 1.1 | 1.1 | 120 |
| Example 15 | 0.1 | 1.1 | 1.0 | 130 |
| Example 16 | 0.12 | 1.1 | 1.1 | 120 |
| Comparative Example 9 | 0.25 | 3.0 | 1.5 | 70 |
| Comparative Example 10 | 0.25 | 5.0 | 1.5 | 70 |
| Comparative Example 11 | 0.2 | 3.0 | 2.0 | 80 |
| Comparative Example 12 | 0.2 | 4.0 | 1.5 | 70 |
| Comparative Example 13 | 0.2 | 4.0 | 1.2 | 80 |
| Comparative Example 14 | 0.2 | 4.0 | 1.3 | 70 |
| Comparative Example 15 | 0.25 | 4.0 | 1.5 | 60 |
| Comparative Example 16 | 0.2 | 3.0 | 1.5 | 80 |
| Example 17 | 130 | 1.1 | 1.1 | 100 (Reference of 410 nm) |
| Example 18 | 110 | 1.1 | 1.1 | 100 |
| Example 19 | 100 | 1.1 | 1.1 | 150 |
| Example 20 | 100 | 1.1 | 1.1 | 130 |
| Example 21 | 100 | 1.1 | 1.1 | 150 |
| Example 22 | 100 | 1.1 | 1.1 | 110 |
| Example 23 | 110 | 1.1 | 1.1 | 120 |
| Example 24 | 120 | 1.1 | 1.1 | 150 |
| Comparative Example 17 | 200 | 1.1 | 2.0 | 50 |
| Comparative Example 18 | 200 | 1.1 | 2.0 | 50 |
| Comparative Example 19 | 200 | 1.1 | 1.5 | 60 |
| Comparative Example 20 | 180 | 1.1 | 2.0 | 60 |
| Comparative Example 21 | 200 | 1.1 | 1.5 | 60 |
| Comparative Example 22 | 200 | 1.1 | 2.5 | 50 |
| Comparative Example 23 | 180 | 1.1 | 2.0 | 70 |
| Comparative Example 24 | 200 | 1.1 | 1.5 | 70 |
| Comparative Example 25 | 0.3 | 5.0 | 2.0 | 60 |
| Comparative Example 26 | 0.1 | 3.0 | 1.1 | 90 |
| Comparative Example 27 | 0.1 | 3.0 | 1.1 | 80 |
| Comparative Example 28 | 0.3 | 4.0 | 2.5 | 50 |
| Comparative Example 29 | 200 | 4.0 | 2.0 | 50 |
| Comparative Example 30 | 200 | 4.0 | 1.1 | 80 |
| Comparative Example 31 | 150 | 3.0 | 1.1 | 80 |
| Comparative Example 32 | 150 | 4.0 | 1.5 | 60 |

COMPOUNDS IN TABLE 1
Y-1
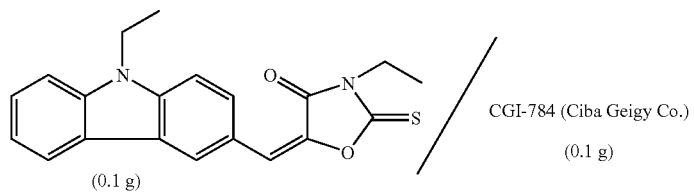
(0.1 g) / CGI-784 (Ciba Geigy Co.) (0.1 g)
Y-2
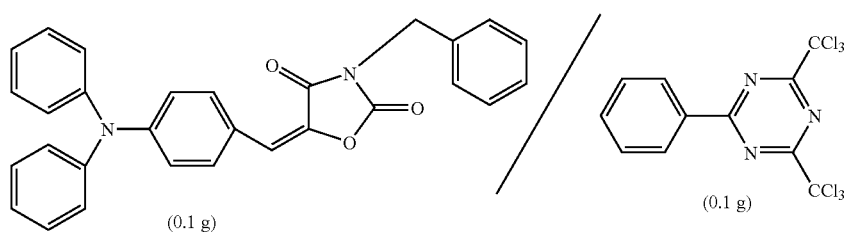
(0.1 g) / (0.1 g)
Y-3
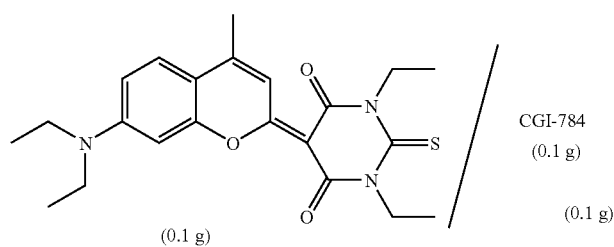
(0.1 g) / CGI-784 (0.1 g)
Y-4
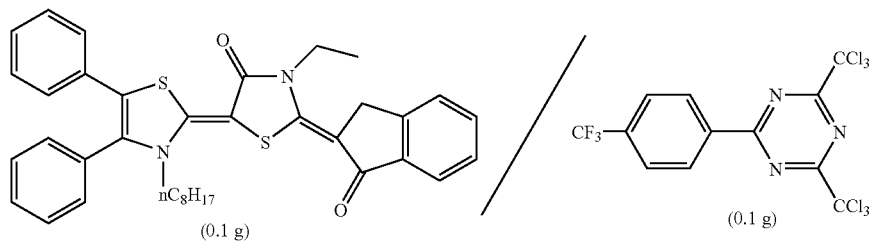
(0.1 g) / (0.1 g)

COMPOUNDS IN TABLE 1-continued
Y-5
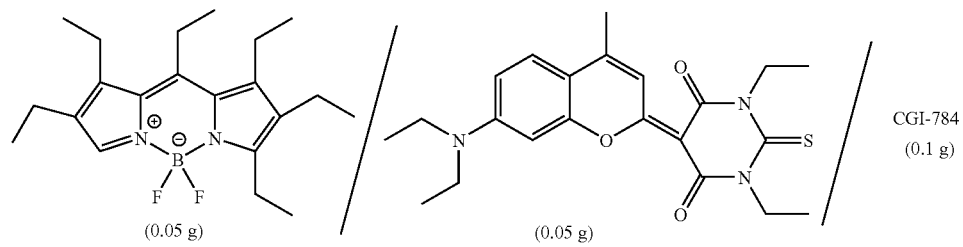
Y-6
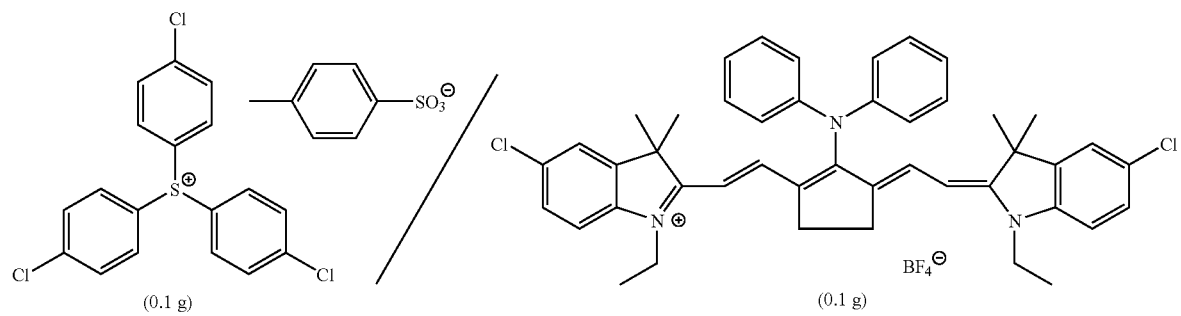
Y-7
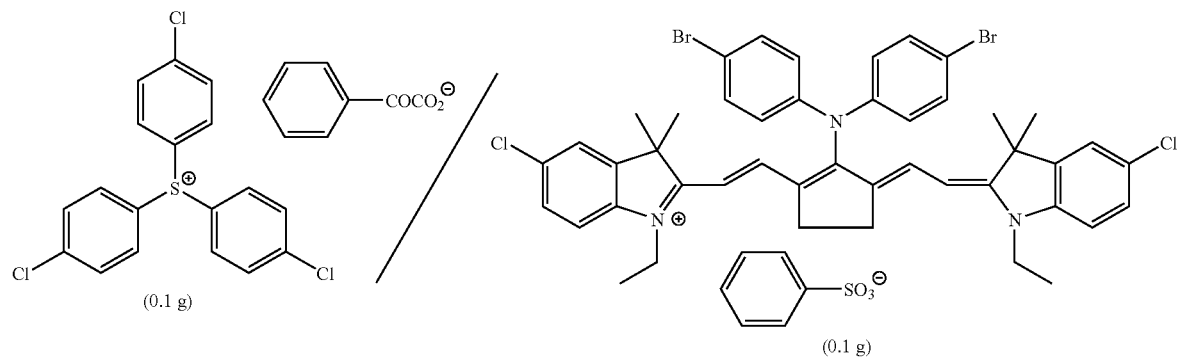
Y-8
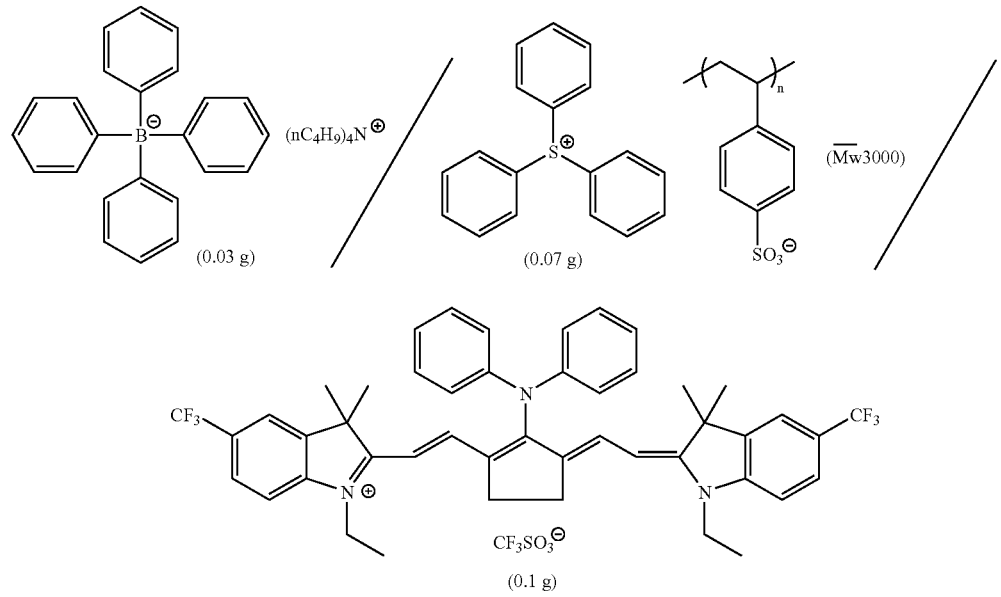

COMPOUNDS IN TABLE 1-continued
S-1
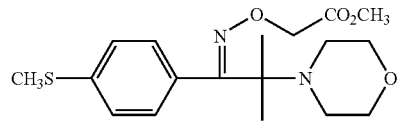
S-2
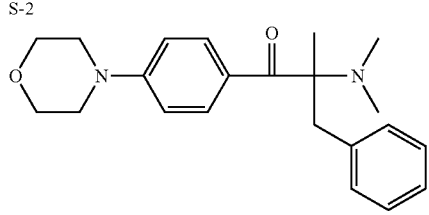
S-3
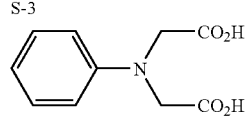
S-4
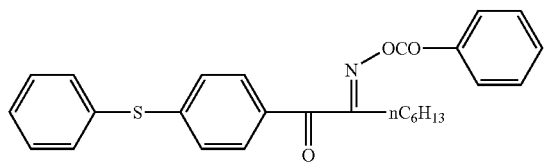
Z-1
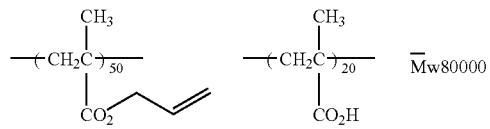
Z-2
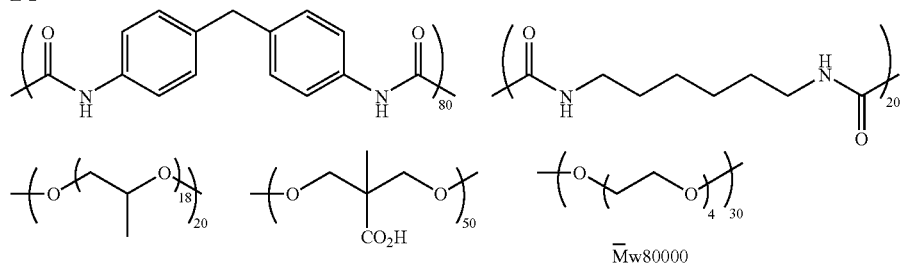
Z-3
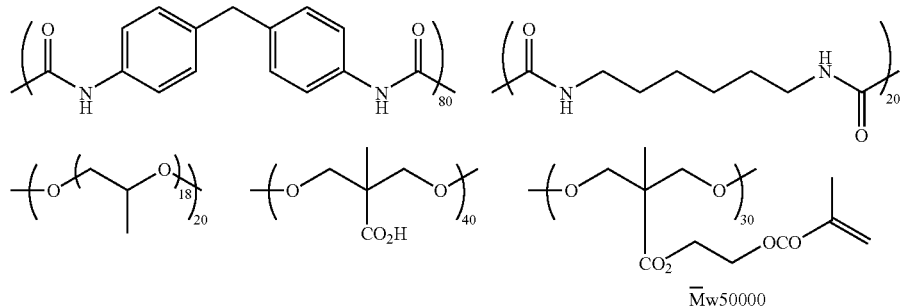
Z-4
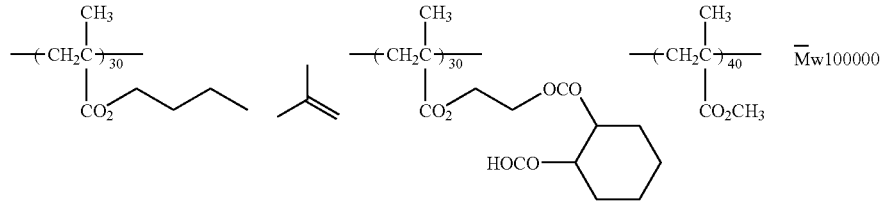
Comparative Compounds

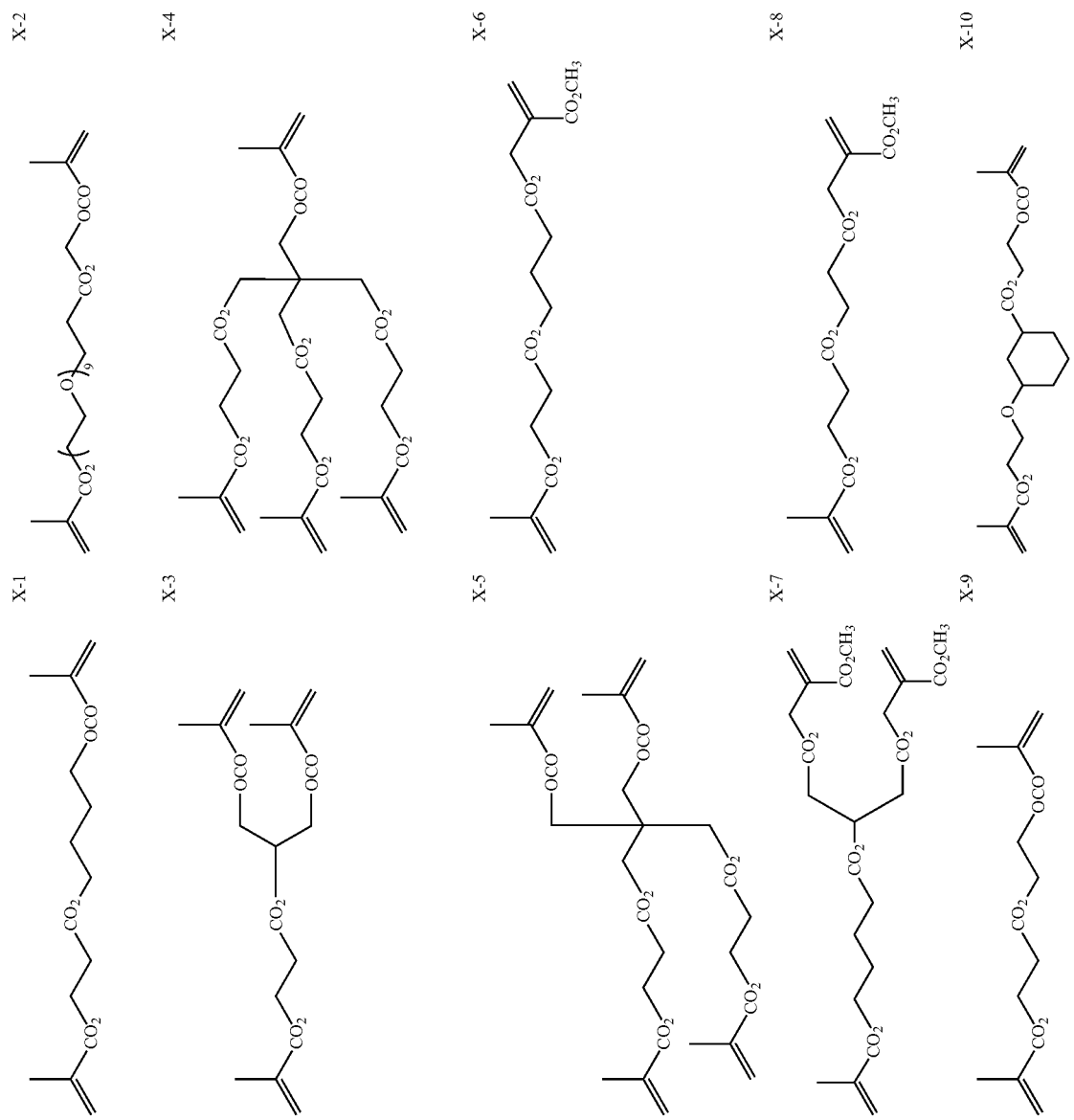

-continued
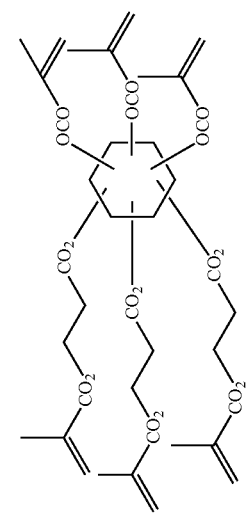
X-11
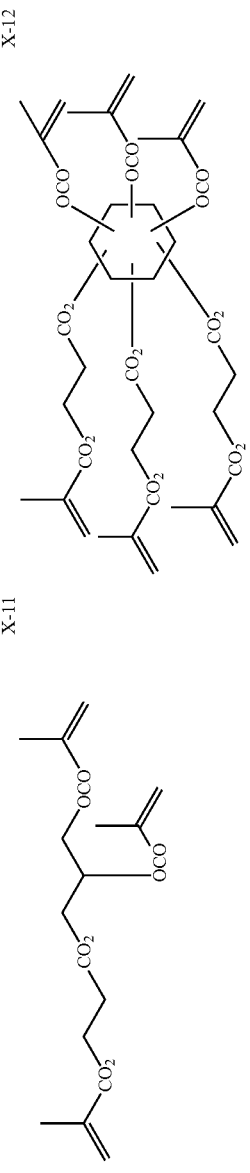
X-12
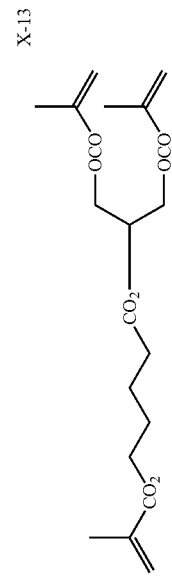
X-13
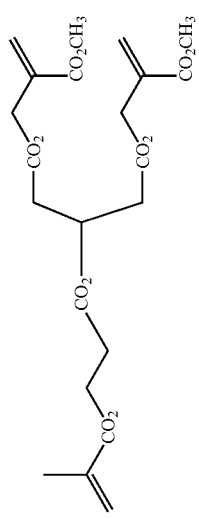
X-14
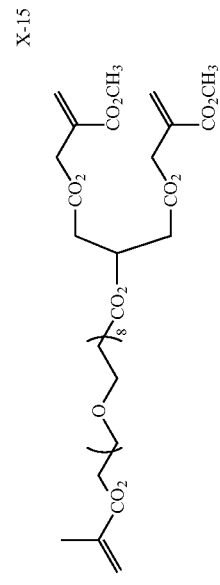
X-15
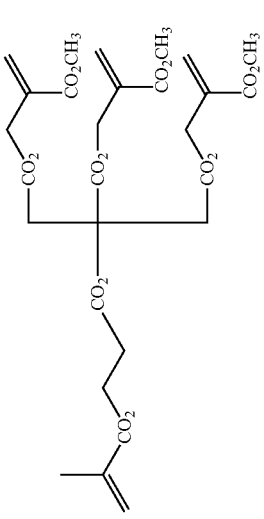
X-16
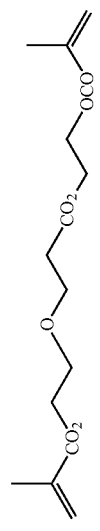
X-17
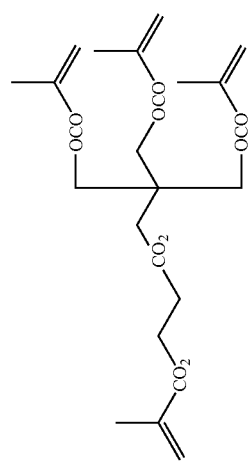
X-18

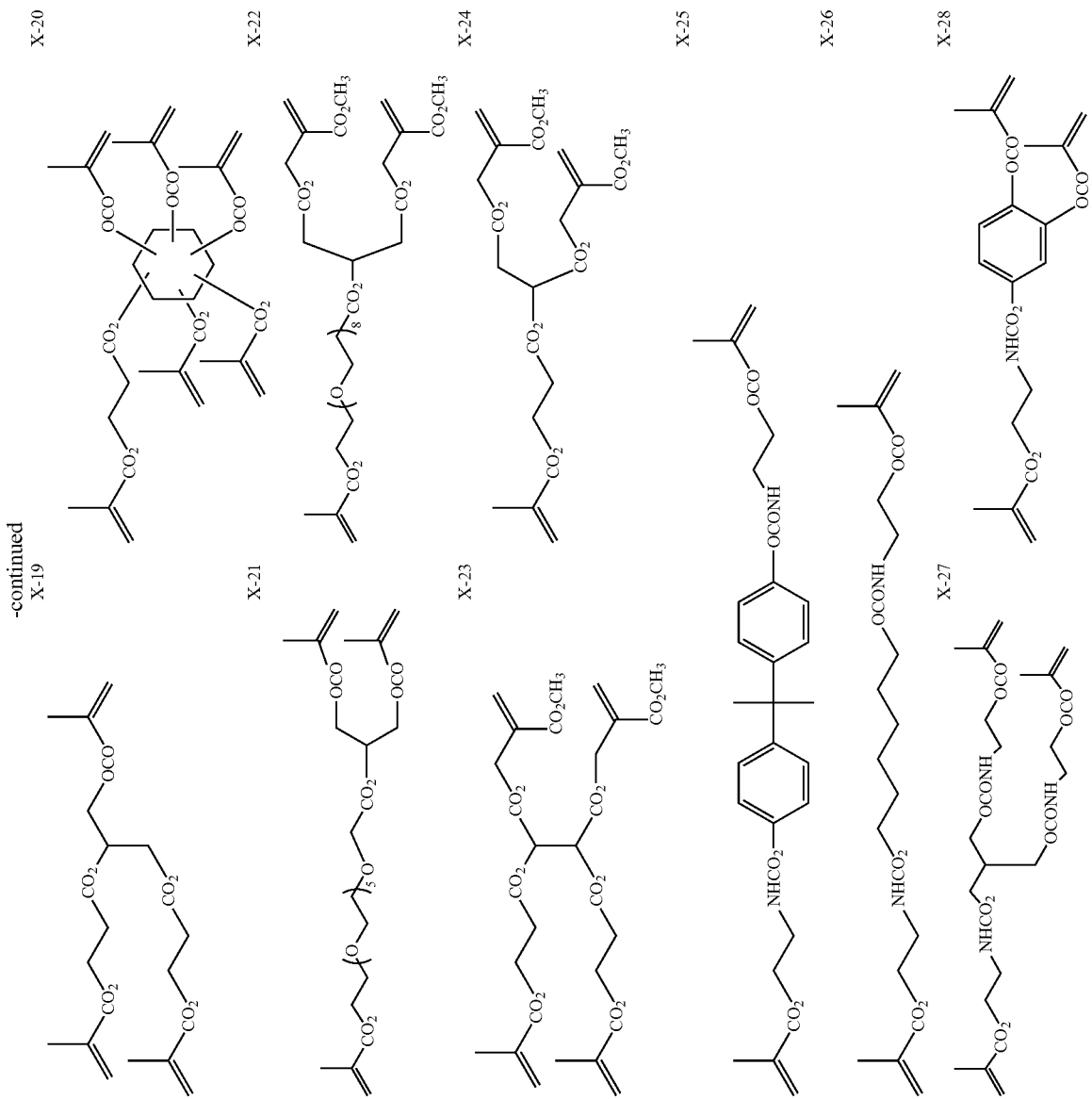

As can be seen in Table 2 above, the printing plate precursor comprising the photopolymerizable composition of the invention exhibits a high sensitivity, a small temperature dependence of sensitivity, an essentially high polymerization rate, a long press life and a good storage stability.

As mentioned above, the polymerizable composition of the invention can satisfy all the requirements of high sensitivity, small temperature dependence of sensitivity, excellent storage stability and long press life when it comprises a polyfunctional crosslinking agent of the invention represented by the general formula (I) or (II) incorporated therein as provided as a photoradical polymerization composition, which has the highest sensitivity and thus is considered promising in the art of image formation. In particular, the invention can provide a polymerizable composition suitable for a lithographic printing plate precursor which enables direct plate making from digital data from computer, etc. when recording is conducted using a solid laser or semiconductor laser emitting visible light or infrared ray.

The present application claims foreign priority based on Japanese Patent Application No. JP2002-58582, filed Mar. 3 of 2003, the content of which is incorporated herein by reference.

What is claimed is:

1. A polymerizable composition comprising a compound represented by the following general formula (I):

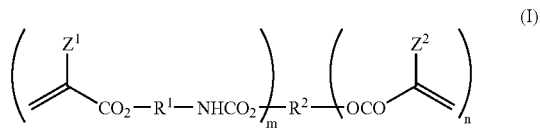

wherein $Z^1$ represents a hydrogen atom or $CH_3$; $Z^2$ represents H, $CH_3$ or $CHR^bX^1$; $X^1$ represents a substituted oxy group, a substituted amino group or a substituted thio group; $R^b$ represents a hydrogen atom or a hydrocarbon group; $R^1$ represents a divalent aliphatic hydrocarbon connecting group, which may include an —O— connecting group; $R^2$ represents an aliphatic hydrocarbon connecting group having a valence of (m+n), which may include an —O— connecting group, and is a connecting group having a valence of 3 to 6; and m and n each independently represents an integer of from 1 to 5, wherein m+n is 3 to 6.

2. The polymerizable composition as claimed in claim 1, further comprising an alkali-soluble polyurethane resin.

3. The polymerizable composition as claimed in claim 1, wherein the divalent aliphatic hydrocarbon connecting group in $R^1$, is a divalent connecting group in which one hydrogen is removed from an alkyl group or a substituted alkyl group.

4. The polymerizable composition as claimed in claim 1, wherein the divalent aliphatic hydrocarbon connecting group in $R^2$, is a connecting group having a valence of (m+n), in which a number of (m+n−1) of hydrogen(s) is removed from an alkyl group or a substituted alkyl group.

5. The polymerizable composition as claimed in claim 1, wherein the hydrocarbon group in $R^b$ is a substituted or unsubstituted hydrocarbon, which may contain an unsaturated bond.

6. The polymerizable composition as claimed in claim 1, wherein the hydrocarbon group in $R^b$ is a substituted or unsubstituted alkyl group, a substituted or unsubstituted aryl group, a substituted or unsubstituted alkenyl group, or a substituted or unsubstituted alkynyl group.

7. The polymerizable composition as claimed in claim 1, wherein the divalent aliphatic hydrocarbon connecting group in $R^2$, is selected from the group consisting of the following structures:

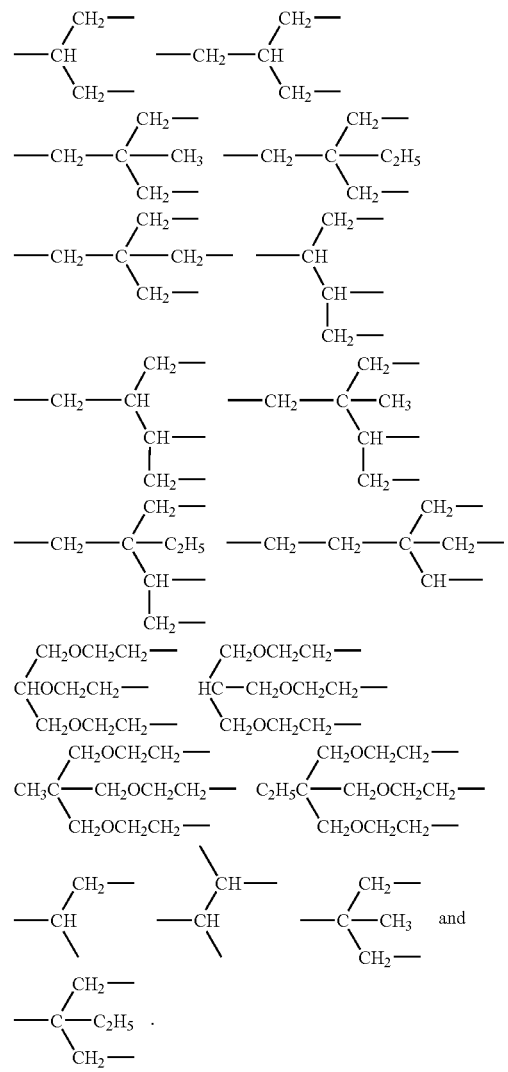

8. The polymerizable composition as claimed in claim 1, wherein each of $Z^1$ and $Z^2$ is $CH_3$.

9. A compound represented by the following general formula (I):

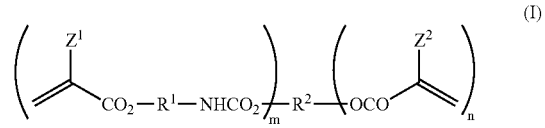

wherein $Z^1$ represents a hydrogen atom or $CH_3$; $Z^2$ represents H, $CH_3$ or $CHR^bX^1$; $X^1$ represents a substituted oxy, amino or thio group; $R^b$ represents a hydrogen atom or a hydrocarbon group; $R^1$ represents an aliphatic hydrocarbon connecting group which may have moieties connected to each other via divalent oxygen; R² represents an aliphatic hydrocarbon connecting group having a valence of (m+n), which may have moieties connected to each other via oxygen, and is a connecting group having a valence of 3 to 6; and m and n each independently represents an integer of from 1 to 5, wherein m+n is 3 to 6.

10. A compound represented by the following general formula (II):

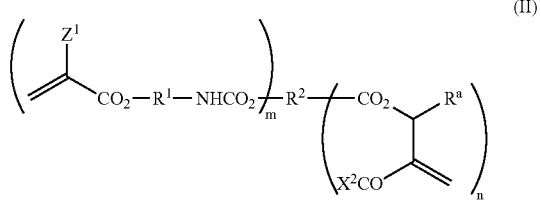

wherein Z¹ represents a hydrogen atom or CH₃; X² represents a substituted oxy, amino or thio group; Rᵃ represents a hydrogen atom or a hydrocarbon group; R¹ represents an aliphatic hydrocarbon connecting group which may have moieties connected to each other via divalent oxygen; R² represents an aliphatic hydrocarbon connecting group which may have moieties connected to each other via oxygen having a valence of (m+n); and m and n each independently represents an integer of from 1 to 5.

11. An image recording material comprising a recording layer, the recording layer comprising a polymerizable composition according to claim 1.

12. A polymerizable composition comprising a compound represented by the following general formula (II):

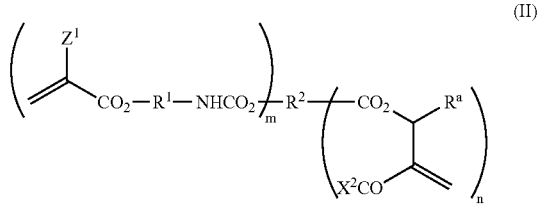

wherein Z¹ represents a hydrogen atom or CH₃; X² represents a substituted oxy group, a substituted amino group or a substituted thio group; Rᵃ represents a hydrogen atom or a hydrocarbon group; R¹ represents a divalent aliphatic hydrocarbon connecting group, which may include an —O— connecting group; R² represents an aliphatic hydrocarbon connecting group having a valence of (m+n), which may include an —O— connecting group; and m and n each independently represents an integer of from 1 to 5.

13. The polymerizable composition as claimed in claim 15, further comprising an alkali-soluble polyurethane resin.

14. The polymerizable composition as claimed in claim 12, wherein the divalent aliphatic hydrocarbon connecting group in R¹, is a divalent connecting group in which one hydrogen is removed from an alkyl group or a substituted alkyl group.

15. The polymerizable composition as claimed in claim 12, wherein the divalent aliphatic hydrocarbon connecting group in R², is a connecting group having a valence of (m+n), in which a number of (m+n−1) of hydrogen(s) is removed from an alkyl group or a substituted alkyl group.

16. The polymerizable composition as claimed in claim 12, wherein the hydrocarbon group in Rᵃ is a substituted or unsubstituted hydrocarbon, which may contain an unsaturated bond.

17. The polymerizable composition as claimed in claim 12, wherein the hydrocarbon group in Rᵃ is a substituted or unsubstituted alkyl group, a substituted or unsubstituted aryl group, a substituted or unsubstituted alkenyl group, or a substituted or unsubstituted alkynyl group.

18. The polymerizable composition as claimed in claim 12, wherein the divalent aliphatic hydrocarbon connecting group in R², is a connecting group having a valence of 3 to 6.

19. The polymerizable composition as claimed in claim 12, wherein the divalent aliphatic hydrocarbon connecting group in R², is selected from the group consisting of the following structures:

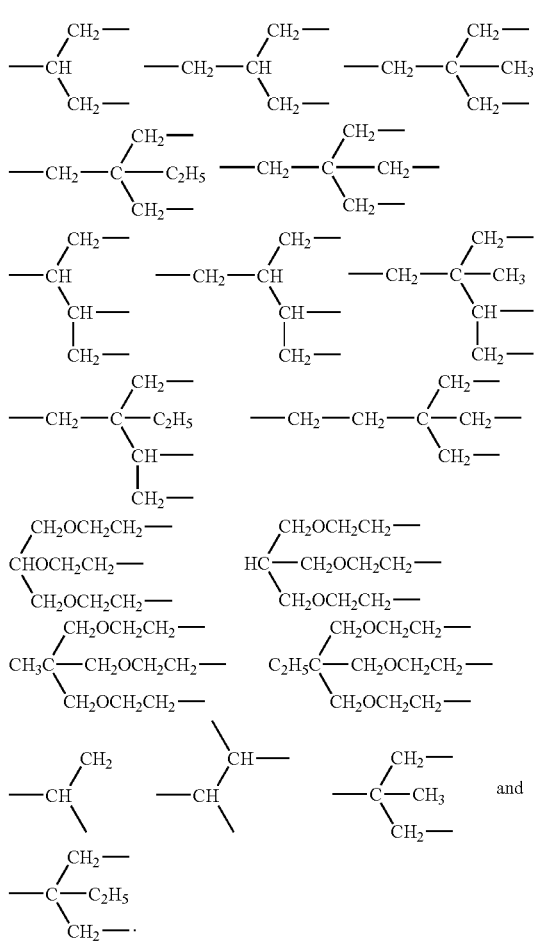

20. The polymerizable composition as claimed in claim 12, wherein m+n is 3 to 6.

21. The polymerizable composition as claimed in claim 20, wherein each of Z¹ and Z² is CH₃.

22. An image recording material comprising a recording layer, the recording layer comprising a polymerizable composition according to claim 12.

23. A polymerizable composition comprising at least one of compounds represented by the following general formulae (I) and (II), and an alkali-soluble polyurethane resin:

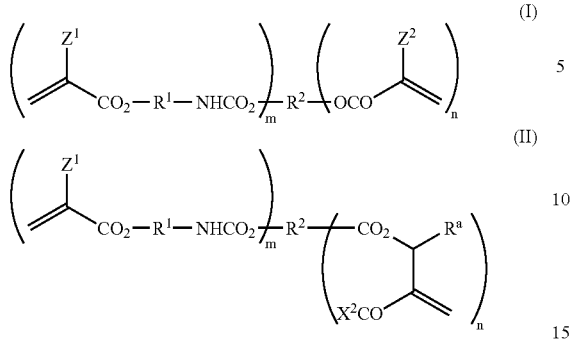

(I)

(II)

wherein $Z^1$ represents a hydrogen atom or $CH_3$; $Z^2$ represents H, $CH_3$ or $CHR^bX^1$; $X^1$ and $X^2$ each independently represents a substituted oxy group, a substituted amino group or a substituted thio group; $R^a$ and $R^b$ each independently represents a hydrogen atom or a hydrocarbon group; $R^1$ represents a divalent aliphatic hydrocarbon connecting group, which may include an —O— connecting group; $R^2$ represents an aliphatic hydrocarbon connecting group having a valence of (m+n), which may include an —O— connecting group; and m and n each independently represents an integer of from 1 to 5.

24. The polymerizable composition as claimed in claim 23, wherein the divalent aliphatic hydrocarbon connecting group in $R^1$, is a divalent connecting group in which one hydrogen is removed from an alkyl group or a substituted alkyl group.

25. The polymerizable composition as claimed in claim 23, wherein the divalent aliphatic hydrocarbon connecting group in $R^2$, is a connecting group having a valence of (m+n), in which a number of (m+n−1) of hydrogen(s) is removed from an alkyl group or a substituted alkyl group.

26. The polymerizable composition as claimed in claim 23, wherein the hydrocarbon group in $R^a$ and $R^b$ is a substituted or unsubstituted hydrocarbon, which may contain an unsaturated bond.

27. The polymerizable composition as claimed in claim 23, wherein the hydrocarbon group in $R^a$ and $R^b$ is a substituted or unsubstituted alkyl group, a substituted or unsubstituted aryl group, a substituted or unsubstituted alkenyl group, or a substituted or unsubstituted alkynyl group.

28. The polymerizable composition as claimed in claim 23, wherein the divalent aliphatic hydrocarbon connecting group in $R^2$, is a connecting group having a valence of 3 to 6.

29. The polymerizable composition as claimed in claim 23, wherein the divalent aliphatic hydrocarbon connecting group in $R^2$, is selected from the group consisting of the following structures:

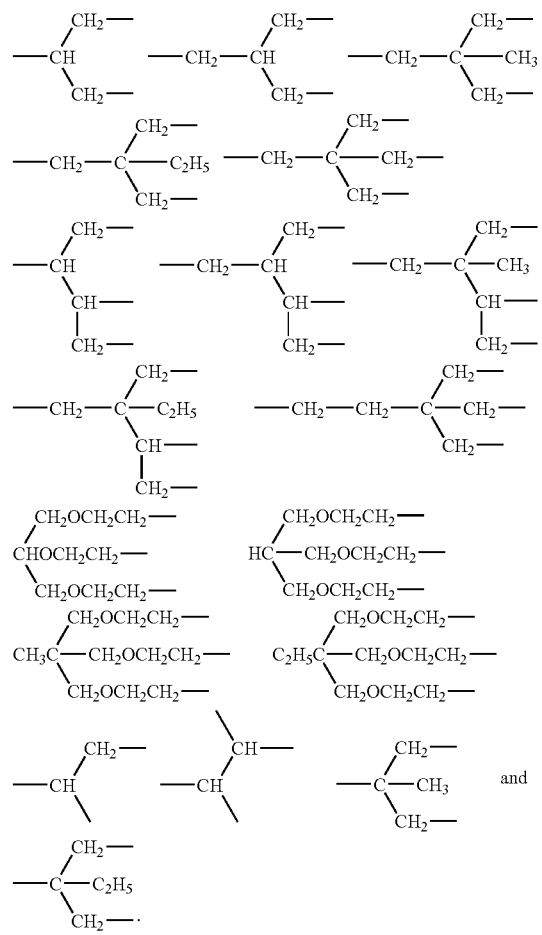

30. The polymerizable composition as claimed in claim 23, wherein m+n is 3 to 6.

31. The polymerizable composition as claimed in claim 30, wherein each of $Z^1$ and $Z^2$ is $CH_3$.

32. An image recording material comprising a recording layer, the recording layer comprising a polymerizable composition according to claim 23.

* * * * *